United States Patent
Burioni et al.

(10) Patent No.: US 10,626,167 B2
(45) Date of Patent: Apr. 21, 2020

(54) HUMAN MONOCLONAL ANTIBODIES ENDOWED WITH STRONG NEUTRALIZING ACTIVITY AGAINST HSV-1 AND HSV-2

(71) Applicant: Polichem S.A., Luxembourg (LU)

(72) Inventors: Roberto Burioni, Segrate (IT);
Massimo Clementi, Milan (IT);
Daniela Concas, Zurich (CH)

(73) Assignee: POLICHEM S.A., Luxembourg (LU)

(*) Notice: Subject to any disclaimer, the term of this patent is extended or adjusted under 35 U.S.C. 154(b) by 0 days.

(21) Appl. No.: 15/546,422

(22) PCT Filed: Jan. 28, 2016

(86) PCT No.: PCT/EP2016/051844
§ 371 (c)(1),
(2) Date: Jul. 26, 2017

(87) PCT Pub. No.: WO2016/120410
PCT Pub. Date: Aug. 4, 2016

(65) Prior Publication Data
US 2018/0009879 A1 Jan. 11, 2018

(30) Foreign Application Priority Data
Jan. 28, 2015 (EP) .................................... 15152909

(51) Int. Cl.
*C07K 16/08* (2006.01)
*A61K 39/42* (2006.01)
*A61K 45/06* (2006.01)
*A61K 39/00* (2006.01)

(52) U.S. Cl.
CPC ............ *C07K 16/087* (2013.01); *A61K 39/42* (2013.01); *A61K 45/06* (2013.01); *A61K 2039/505* (2013.01); *C07K 2317/21* (2013.01); *C07K 2317/33* (2013.01); *C07K 2317/55* (2013.01); *C07K 2317/76* (2013.01)

(58) Field of Classification Search
CPC .............. A61K 2039/505; A61K 39/12; A61K 39/395; A61K 39/00; A61K 39/42; A61K 35/763
See application file for complete search history.

(56) References Cited

U.S. PATENT DOCUMENTS 6,156,313 A 12/2000 Burton et al.
2010/0172906 A1 7/2010 Lai et al.

FOREIGN PATENT DOCUMENTS

| EP | 2 308 895 A1 | 4/2011 |
| JP | 2001-501101 A | 1/2001 |
| JP | 2012-526075 A | 10/2012 |
| JP | 2013-506403 A | 2/2013 |
| WO | WO 97/26329 | 7/1997 |

OTHER PUBLICATIONS

Clementi N, Criscuolo E, Cappelletti F, Quaranta P, Pistello M, Diotti RA, Sautto GA, Tarr AW, Mailland F, Concas D, Burioni R, Clementi M, Mancini N. Entry inhibition of HSV-1 and -2 protects mice from viral lethal challenge. Antiviral Res. Jul. 2017;143:48-61. Epub Apr. 8, 2017.*
Kimberlin DM. Immunotherapy of HSV infections—antibody delivery. In: Arvin A, Campadelli-Fiume G, Mocarski E, et al., editors. Human Herpesviruses: Biology, Therapy, and Immunoprophylaxis. Cambridge: Cambridge University Press; 2007. Chapter 75. Available from: https://www.ncbi.nlm.nih.gov/books/NBK47389/.*
Balachandran N, Oba DE, Hutt-Fletcher LM. Antigenic cross-reactions among herpes simplex virus types 1 and 2, Epstein-Barr virus, and cytomegalovirus. J Virol. Apr. 1987;61(4):1125-35.*
Simmonds P, Smith IW, Peutherer JF. Detection of antibody to viral proteins following primary infection with herpes simplex virus. J Med Virol. Oct. 1987;23(2):191-205.*
World Health Organization (WHO). Status of Vaccine Research and Development of Vaccines for Herpes Simplex Virus, Prepared for WHO PD-VAC. Sep. 2014.*
Zabetakis D, Anderson GP, Bayya N, Goldman ER. Contributions of the complementarity determining regions to the thermal stability of a single-domain antibody. PLoS One. Oct. 15, 2013;8(10):e77678. doi: 10.1371/journal.pone.0077678. eCollection 2013.*
Sela-Culang I, Kunik V, Ofran Y. The structural basis of antibody-antigen recognition. Front Immunol. Oct. 8, 2013;4:302.*
Bowie JU, Reidhaar-Olson JF, Lim WA, Sauer RT. Deciphering the message in protein sequences: tolerance to amino acid substitutions. Science. Mar. 16, 1990;247(4948):1306-10.*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14.*
Kussie PH, Parhami-Seren B, Wysocki LJ, Margolies MN. A single engineered amino acid substitution changes antibody fine specificity. J Immunol. Jan. 1, 1994;152(1):146-52.*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714.*
Chen, Jianmin et al., "Prevention of genital herpes in a guinea pig model using a glycoprotein D-specific single chain antibody as a microbicide," Virology Journal, vol. 1, No. 11, pp. 1-10 (2004).

(Continued)

*Primary Examiner* — Rachel B Gill
(74) *Attorney, Agent, or Firm* — Finnegan, Henderson, Farabow, Garrett & Dunner, LLP

(57) ABSTRACT

The present invention is in the field of monoclonal antibodies suitable for passive immunotherapy of Herpes Simplex Virus infections and relates to human monoclonal antibodies or fragments of said antibodies, which bind and neutralize HSV-1 and HSV-2, and their use in the prophylaxis or treatment of HSV-1 or HSV-2-associated diseases.

13 Claims, 33 Drawing Sheets
Specification includes a Sequence Listing.

(56) References Cited

OTHER PUBLICATIONS

International Search Report for International Application No. PCT/EP2016/051844, dated May 6, 2016.
Written Opinion of the International Searching Authority for International Application No. PCT/EP2016/051844.
Berman, et al., "Protection from Genital Herpes Simplex Virus Type 2 Infection by Vaccination with Cloned Type 1 Glycoprotein D," Science, vol. 227, pp. 1490-1492 (1985).
Chen, et al., "Prevention of genital herpes in a guinea pig model using a glycoprotein D-specific single chain antibody as a microbicide," Virology Journal, vol. 1, No. 1, pp. 1-10 (2004).

* cited by examiner

HSV1

HSV2

Fab A = Fab Ex2

SEQUENCE LISTING

<160> NUMBER OF SEQ ID NOS: 13

<210> SEQ ID NO 1
<211> LENGTH: 113
<212> TYPE: PRT
<213> ORGANISM: Homo sapiens
<220> FEATURE:
<221> NAME/KEY: VARIANT
<222> LOCATION: (1)..(113)
<223> OTHER INFORMATION: VH1: Fab A heavy chain (VH) variable region

<400> SEQUENCE: 1

```
Leu Glu Ser Gly Gly Gly Val Val Gln Pro Gly Arg Ser Leu Arg Leu
1               5                   10                  15

Ser Cys Ala Ala Ser Gly Phe Thr Phe Thr Thr Phe Ala Met His Trp
            20                  25                  30

Val Arg Gln Ala Pro Gly Lys Gly Leu Glu Trp Leu Ala Phe Ile Ser
        35                  40                  45

Tyr Asp Gly Ser Asn Lys Tyr Tyr Ala Asp Ser Val Lys Gly Arg Phe
    50                  55                  60

Thr Ile Ser Arg Asp Asn Ser Lys Asn Thr Leu Tyr Leu Gln Met Asn
65                  70                  75                  80

Ser Leu Arg Ala Glu Asp Thr Ser Ile Tyr Tyr Cys Ala Arg Glu Val
                85                  90                  95

Trp Asn Tyr Ala Asp Tyr Trp Gly Gln Gly Ala Leu Val Thr Val Ser
            100                 105                 110

Ser
```

<210> SEQ ID NO 2
<211> LENGTH: 106
<212> TYPE: PRT
<213> ORGANISM: Homo sapiens
<220> FEATURE:
<221> NAME/KEY: VARIANT
<222> LOCATION: (1)..(106)
<223> OTHER INFORMATION: VL1 Fab A light chain (VL) variable region

<400> SEQUENCE: 2

Glu Leu Thr Gln Ser Pro Gly Thr Leu Ser Ser Pro Gly His Arg
1               5                   10                  15

Ala Thr Leu Ser Cys Lys Ala Ser Ala Pro Leu Gly Ser Asn His Met
            20                  25                  30

Ala Trp Tyr Gln Gln Lys Pro Gly Gln Ala Pro Arg Leu Leu Ile Tyr
        35                  40                  45

Gly Ala Ser Thr Arg Ala Thr Gly Val Pro Ala Arg Phe Thr Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ala Asn Ser Phe Pro Arg Thr
                85                  90                  95

Phe Gly Gln Gly Thr Lys Val Glu Ile Lys
            100                 105

<210> SEQ ID NO 3
<211> LENGTH: 8
<212> TYPE: PRT
<213> ORGANISM: Homo sapiens
<220> FEATURE:
<221> NAME/KEY: VARIANT
<222> LOCATION: (1)..(8)
<223> OTHER INFORMATION: VH1CDR Fab A complementary determining region

<400> SEQUENCE: 3

Glu Val Trp Asn Tyr Ala Asp Tyr
1               5

<210> SEQ ID NO 4
<211> LENGTH: 118
<212> TYPE: PRT
<213> ORGANISM: Homo sapiens
<220> FEATURE:
<221> NAME/KEY: VARIANT
<222> LOCATION: (1)..(118)
<223> OTHER INFORMATION: VH3: Fab B heavy chain (VH) variable region
<220> FEATURE:
<221> NAME/KEY: VARIANT
<222> LOCATION: (1)..(118)
<223> OTHER INFORMATION: VH51 Fab I heavy chain (VH) variable region

<400> SEQUENCE: 4

Leu Glu Gln Ser Gly Ala Glu Val Lys Lys Pro Gly Ala Ser Val Arg
1               5                   10                  15

Val Ser Cys Gln Ala Ser Gly Tyr Thr Phe Thr Asn Tyr Tyr Ile His
            20                  25                  30

Trp Val Arg Gln Ala Pro Gly Gln Gly Leu Glu Trp Met Gly Ile Ile
        35                  40                  45

Asn Pro Thr Gly Gly Ser Thr Arg Ile Ala Gln Lys Phe Gln Gly Arg
    50                  55                  60

Val Thr Met Thr Ser Asp Thr Ser Thr Ile Phe Met Glu Val
65                  70                  75                  80

Ser Ser Leu Arg Ser Glu Asp Thr Ala Ile Tyr Tyr Cys Ala Arg Asp
            85                  90                  95

Glu Tyr Lys Ser His His Tyr Gly Met Asp Val Trp Gly Gln Gly Thr
        100                 105                 110

Thr Val Thr Val Ser Ser
        115

<210> SEQ ID NO 5
<211> LENGTH: 107
<212> TYPE: PRT
<213> ORGANISM: Homo sapiens
<220> FEATURE:
<221> NAME/KEY: VARIANT
<222> LOCATION: (1)..(107)
<223> OTHER INFORMATION: VL3 Fab B light chain (VL) variable region

<400> SEQUENCE: 5

Glu Leu Thr Gln Ser Pro Gly Thr Leu Ser Leu Ser Pro Gly Glu Arg
1               5                   10                  15

Ala Thr Leu Ser Cys Arg Ala Asn Glu Ser Val Ser Arg Ser Tyr Leu
            20                  25                  30

Ala Trp Tyr Gln Gln Arg Pro Gly Gln Ala Pro Arg Leu Leu Ile Tyr
        35                  40                  45

Gly Ala Ser Thr Arg Ala Thr Gly Ile Pro Ala Arg Phe Ser Gly Ser
50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln His Phe Gly Ser Ser Thr Gly Leu
                85                  90                  95

Thr Phe Gly Gly Gly Thr Lys Val Glu Ile Arg
            100                 105

<210> SEQ ID NO 6
<211> LENGTH: 12
<212> TYPE: PRT
<213> ORGANISM: Homo sapiens
<220> FEATURE:
<221> NAME/KEY: VARIANT
<222> LOCATION: (1)..(12)
<223> OTHER INFORMATION: VH3CDR Fab B complementary determining region
<220> FEATURE:
<221> NAME/KEY: VARIANT
<222> LOCATION: (1)..(12)
<223> OTHER INFORMATION: VH51CDR Fab I complementary determining region

<400> SEQUENCE: 6

Asp Glu Tyr Lys Ser His His Tyr Gly Met Asp Val
1               5                   10

<210> SEQ ID NO 7
<211> LENGTH: 120
<212> TYPE: PRT
<213> ORGANISM: Homo sapiens
<220> FEATURE:
<221> NAME/KEY: VARIANT
<222> LOCATION: (1)..(120)
<223> OTHER INFORMATION: VH5 Fab C heavy chain (VH) variable region

<400> SEQUENCE: 7

Leu Glu Ser Gly Gly Gly Leu Val Gln Pro Gly Gly Ser Leu Arg Leu
1               5                   10                  15

Ser Cys Ala Ala Ser Gly Leu Pro Phe Asn Tyr Tyr Ala Met Asn Trp
            20                  25                  30

Val Arg Gln Ala Pro Gly Lys Gly Leu Glu Trp Val Ser Gly Ile Ser
        35                  40                  45

Ala Asn Gly Leu Asn Thr Tyr Tyr Ala Glu Ser Val Lys Gly Arg Phe
    50                  55                  60

Thr Ile Ser Arg Glu Asn Ser Gln Asn Thr Leu Tyr Leu Gln Met Asn
65                  70                  75                  80

Ser Leu Gly Ala Glu Asp Thr Ala Val Tyr Tyr Cys Ala Lys Val Leu
                85                  90                  95

Val Ala Ala Thr His Tyr Tyr Tyr Asn Gly Met Asp Val Trp Gly Gln
            100                 105                 110

Gly Thr Thr Val Thr Val Ser Ser
            115                 120

<210> SEQ ID NO 8
<211> LENGTH: 106
<212> TYPE: PRT
<213> ORGANISM: Homo sapiens
<220> FEATURE:
<221> NAME/KEY: VARIANT
<222> LOCATION: (1)..(106)
<223> OTHER INFORMATION: VL5 Fab C light chain (VL) variable region

<400> SEQUENCE: 8

Glu Leu Thr Gln Ser Pro Val Thr Leu Ser Leu Ser Pro Gly Glu Arg
1               5                   10                  15

Ala Thr Leu Ser Cys Gly Ala Ser Gln Ser Val Ser Ser Ser Asn Leu
            20                  25                  30

Ala Trp Tyr Gln Gln Lys Pro Gly Leu Ala Pro Arg Leu Leu Ile Tyr
        35                  40                  45

Asp Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Ser Ser Leu Ile Thr
                85                  90                  95

Phe Gly Gln Gly Thr Arg Leu Glu Ile Lys
            100                 105

<210> SEQ ID NO 9
<211> LENGTH: 15
<212> TYPE: PRT
<213> ORGANISM: Homo sapiens
<220> FEATURE:
<221> NAME/KEY: VARIANT
<222> LOCATION: (1)..(15)
<223> OTHER INFORMATION: VH5CDR Fab C complementary determining region

<400> SEQUENCE: 9

Val Leu Val Ala Ala Thr His Tyr Tyr Tyr Asn Gly Met Asp Val
1               5                   10                  15

<210> SEQ ID NO 10
<211> LENGTH: 121
<212> TYPE: PRT
<213> ORGANISM: Homo sapiens
<220> FEATURE:
<221> NAME/KEY: VARIANT
<222> LOCATION: (1)..(121)
<223> OTHER INFORMATION: VH47 Fab H heavy chain (VH) variable region

<400> SEQUENCE: 10

Leu Glu Glu Ser Gly Ala Glu Val Lys Lys Pro Gly Ala Ser Val Arg
1               5                   10                  15

Val Ser Cys Lys Ala Ser Gly Tyr Thr Phe Thr Gly Tyr Phe Ile His
            20                  25                  30

Trp Val Arg Gln Ala Pro Gly Gln Gly Leu Glu Trp Met Gly Trp Ile
        35                  40                  45

Asn Pro Lys Ser Gly Gly Thr Asn Tyr Ala Pro Lys Phe Gln Gly Arg
    50                  55                  60

Val Thr Met Thr Arg Asp Thr Ser Ile Ser Thr Ala Tyr Met Gln Leu
65                  70                  75                  80

Ser Ser Val Arg Ser Asp Asp Thr Ala Val Tyr Tyr Cys Ala Arg Glu
                85                  90                  95

Glu Ile Pro Leu Tyr Tyr Asp Ser Gly Tyr Gly Met Asp Val Trp Gly
            100                 105                 110

Pro Gly Thr Thr Val Thr Val Ser Ser
            115                 120

<210> SEQ ID NO 11
<211> LENGTH: 107
<212> TYPE: PRT
<213> ORGANISM: Homo sapiens
<220> FEATURE:
<221> NAME/KEY: VARIANT
<222> LOCATION: (1)..(107)
<223> OTHER INFORMATION: VL47 Fab H light chain (VL) variable region

<400> SEQUENCE: 11

Glu Leu Thr Gln Ser Pro Gly Thr Leu Ser Leu Ser Pro Gly Glu Arg
1               5                   10                  15

Ala Thr Leu Ser Cys Arg Ala Ser Gln Ser Val Ser Ser Ser Tyr Leu
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Ser Ser Pro Arg Leu
                85                  90                  95

Thr Phe Gly Gly Gly Thr Lys Val Glu Ile Lys
            100                 105

<210> SEQ ID NO 12
<211> LENGTH: 15
<212> TYPE: PRT
<213> ORGANISM: Homo sapiens
<220> FEATURE:
<221> NAME/KEY: VARIANT
<222> LOCATION: (1)..(15)
<223> OTHER INFORMATION: VH47CDR Fab H complementary determining region

<400> SEQUENCE: 12

Glu Glu Ile Pro Leu Tyr Tyr Asp Ser Gly Tyr Gly Met Asp Val
1               5                   10                  15

<210> SEQ ID NO 13
<211> LENGTH: 106
<212> TYPE: PRT
<213> ORGANISM: Homo sapiens
<220> FEATURE:
<221> NAME/KEY: VARIANT -continued

```
<222> LOCATION: (1)..(106)
<223> OTHER INFORMATION: VL51 Fab I light chain (VL) variable region

<400> SEQUENCE: 13

Glu Leu Thr Gln Ser Pro Val Thr Leu Ser Leu Ser Pro Gly Glu Arg
1               5                   10                  15

Ala Thr Leu Ser Cys Gly Ala Ser Gln Ser Val Ser Ser Ser Asn Leu
            20                  25                  30

Ala Trp Tyr Gln Gln Lys Pro Gly Leu Ala Pro Arg Leu Leu Ile Tyr
        35                  40                  45

Asp Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Ser Ser Leu Ile Thr
                85                  90                  95

Phe Gly Gln Gly Thr Arg Leu Glu Ile Lys
            100                 105
```

HUMAN MONOCLONAL ANTIBODIES ENDOWED WITH STRONG NEUTRALIZING ACTIVITY AGAINST HSV-1 AND HSV-2

This application is a national stage filing under 35 U.S.C. § 371 of International Application No. PCT/EP2016/051844, filed on Jan. 28, 2016, which claims priority of European Patent Application No. 15152909.6, filed Jan. 28, 2015. The contents of these applications are each incorporated herein by reference.

FIELD OF THE INVENTION

The present invention is in the field of monoclonal antibodies suitable for the passive immunotherapy of Herpes Simplex Virus 1 and 2 (HSV-1 and HSV-2) infections and relates to human monoclonal antibodies or fragments of said antibodies, which bind and neutralize HSV-1 and HSV-2, and their use in the prophylaxis or treatment of HSV-1 or HSV-2 associated diseases.

TECHNOLOGICAL BACKGROUND

Herpes simplex viruses (HSV) infection-related diseases are a global health problem due to the high infection rates of the general population. Clinical manifestations include small, painful, vesicles affecting the skin, mouth, lips, eyes, or genitalia, and systemic symptoms such as fever and malaise.

HSV persists in sensory and autonomic neural ganglions for the life of the host and periodically reactivates. Clinical recurrences are triggered by several stimuli, such as stress, menstrual periods, fever or illness, sun exposure or sunburn.

The clinical course of HSV infection is strongly influenced by the immune status of the host with severe and life-threatening infections occurring in newborns and immune-compromised patients.

Commonly, antiviral agents targeting the viral DNA such as acyclovir, are used for the management of HSV infections. These drugs can give rise to resistant virus mutants unresponsive to treatment, do not eradicate latent virus or prevent transmission of the infection.

The attempts to develop a prophylactic vaccine have so far failed shedding light on the complexities of the immune response to HSV.

Antibody-based therapies for HSV infections are of key interest due to the fact that the antibody response is crucial for preventing many viral infections and can also contribute to the resolution of different viral infections. Upon viral infection, antibodies are produced against many epitopes on multiple virus proteins. A subset of these antibodies can block virus infection by a process called neutralization. It is increasingly felt the need for novel strategies and options in fighting HSV infections. Specific human monoclonal antibodies with HSV neutralizing activity may provide novel, safe and effective agents for HSV prophylaxis or treatment.

SUMMARY OF THE INVENTION

Natural infections with viruses in general, and with HSV in particular, elicit an antibody response which contains less IgG2 isotype than other IgG subclasses. The present inventors considered that this relative paucity/lack of IgG2 may be related to the ability of HSV to escape the immunological pressure. In addition, the inventors considered that the paucity/lack of IgG2 may contribute to the ability of the virus to reactivate despite the presence of an immune response. Therefore the inventors tested the hypothesis that the presence of IgG2 able to bind and neutralize HSV is protective, by assessing the properties of IgG2 fractions purified from the sera of a small cohort of HSV-seropositive subjects. The inventors demonstrated high HSV neutralizing activity in the IgG2 fraction purified from a single subject reporting no reactivation of labial herpes after suffering from very frequent episodes.

Due to these results, the inventors decided to clone the IgG2 repertoire of this subject in a phage display combinatorial vector and select anti-HSV antibodies in order to generate human monoclonal antibodies of the IgG2 subclass. In fact, the inventors considered the possibility that some of these antibodies could be endowed with a strong neutralizing activity against HSV possibly representing the molecular basis of the reported clinical improvement.

The genes coding for human IgG2 monoclonal antibody Fab fragments were cloned and it was demonstrated that some of them were in fact endowed with a remarkably strong neutralizing activity against both HSV-1 and HSV-2.

The present invention thus concerns human monoclonal antibodies for the prophylaxis or treatment of HSV infection which are specific and selective for HSV and are capable of neutralizing HSV infection. These antibodies represent a promising new alternative to the therapeutic agents known in the art.

The present invention thus concerns monoclonal antibodies and fragments of said antibodies which bind to HSV-1 and HSV-2, and can inhibit HSV infection.

In a first aspect, the present invention relates to an HSV-1 and/or HSV-2 binding monoclonal antibody or fragment thereof comprising both a heavy ($V_H$) and a light chain ($V_L$) variable region, said antibody or fragment thereof comprising a complementary determining region (CDR) chosen from the group consisting of SEQ ID NO: 3, SEQ ID NO: 6, SEQ ID NO: 9 and SEQ ID NO: 12.

The CDRs according to the present invention and having a sequence chosen from the group consisting of SEQ ID NO: 3, SEQ ID NO: 6, SEQ ID NO: 9 and SEQ ID NO: 12, are comprised in the heavy chain variable domain ($V_H$).

In a preferred embodiment, the present invention provides an HSV-1 and HSV-2 binding monoclonal antibody or fragment thereof, wherein said antibody has a heavy chain ($V_H$) variable region of SEQ ID NO:1 and a light chain ($V_L$) variable region of SEQ ID NO:2.

In a second aspect thereof, this invention moreover provides a pharmaceutical composition comprising an HSV-1 and/or HSV-2 binding monoclonal antibody or fragment thereof, according to the present invention and a pharmaceutically acceptable carrier.

In a third aspect, this invention provides an HSV-1 and/or HSV-2 binding monoclonal antibody or fragment thereof, as described above, for use in the prophylaxis or treatment of HSV-1 or HSV-2 associated diseases.

As will be further described in the detailed description of the invention, the human monoclonal antibodies of the present invention have the advantages of neutralizing both HSV-1 and HSV-2 infections. Without being bound to any theory, the monoclonal antibodies of the present invention have the advantages of reducing the formation of syncytia by both HSV-1 and HSV-2.

The human monoclonal antibodies according to the present invention are endowed with a remarkably strong neutralizing activity against both HSV-1 and HSV-2.

The unexpected and surprising properties of these antibodies can fulfill unmet medical needs in the field of HSV infection. The HSV-1 and HSV-2 binding and neutralizing monoclonal antibodies or fragments thereof according to the present invention are strongly believed to be of clinical importance. The antibodies or fragments thereof according to the present invention, are potentially able to fill the therapeutic gap peculiar for herpes simplex viruses which are able to evade the activity of currently available antiviral drugs or agents (such as acyclovir, ibacitabine, pencyclovir, famcyclovir, gancyclovir, valacyclovir, foscarnet, cidofovir). In particular, it is well known in medical literature how certain herpes viral variants can escape anti-HSV drug activity by mutating virus proteins such as herpes-timidine kinase (TK) and/or herpes-polymerase. Moreover, acyclovir drug resistance infers cross-resistance to valacyclovir and famciclovir. An antibody able to neutralize HSV by targeting HSV proteins diverse from viral TK and viral polymerase enzymes, is potentially insensitive to the resistance pattern typical of those HSV clinical isolates able to replicate also in the presence of the aforementioned currently available anti-HSV drugs. Moreover, the antibodies or fragments thereof according to the present invention are also a valid alternative to foscarnet and cidofovir, which are currently used to treat acyclovir-resistant viruses but have a poor safety profile. The great importance of antibodies in clinical therapy has been, in fact, extensively demonstrated. In particular, monoclonal antibodies, including the diverse antibody forms derived from engineering technologies, such as Fab fragments, bispecific or trispecific Fabs (Fab$_2$ and Fab$_3$ respectively) single chains (scFv), bispecific scFv (BisscFv), diabodies, triabodies (trivalent scFv), bivalent minibodies, tetravalent scFv (tetrabodies), nanobodies and recombinant immunoglobulins, are used in biological and medical research. Most importantly, monoclonal antibodies have been successfully used also as therapeutic agents for the treatment of a plethora of human diseases such as cancer (i.e. breast cancer and leukaemia), arthritis, asthma, Crohn's disease, psoriasis, transplant rejection. Moreover, the development of new monoclonal antibodies for the treatment of infectious diseases caused by viruses (i.e. palivizumab in Respiratory Syncytial Virus infection), bacteria and fungi, represents a leading topic in the research field and in the development of new strategies aimed at treating infections caused by microorganisms (including those causing chronic diseases). Furthermore, monoclonal antibodies directed against the aforementioned infective agents take on great importance also for the development of new prophylaxis approaches aimed to prevent (and/or circumscribe), infections due to microbial pathogens. In addition, the use of new antibody-based therapies shed light on the possibility to capitalize on the immunomodulatory potentials of the antibodies.

BRIEF DESCRIPTION OF THE FIGURES

—FIG. 3a: positive infection (HSV-1 virus alone); FIG. 3b: effect of IgG2 purified from subject no. 18 sera; FIG. 3c: effect of IgG2 purified from subject no. 2 sera (negative experimental control): FIG. 3d: uninfected cells.

—FIG. 4a: positive infection (HSV-2 virus alone); FIG. 4b: effect of IgG2 purified from subject no. 18 sera; FIG. 4c: effect of IgG2 purified from subject no. 2 sera (negative experimental control); FIG. 4d: uninfected cells.

—FIG. 5a: positive infection (HSV-1 virus alone); FIG. 5b: effect of IgG2 purified from subject no. 18 sera; FIG. 5c: effect of IgG2 purified from subject no. 2 sera; FIG. 5d: uninfected cells. As depicted in FIG. 5, a strong inhibition of virus replication was observed by pre-incubating the virus with subject no. 18 purified IgG2 (as shown in FIG. 5b, the absence of green-fluorescence signal indicates inhibition of viral replication). The arrows indicate the cells infected by HSV-1; the Hoechst nuclear staining is light grey.

—FIG. 6a: positive infection (HSV-2 virus alone); FIG. 6b: effect of IgG2 purified from subject no. 18 sera; FIG. 6c: effect of IgG2 purified from subject no. 2 sera; FIG. 6d: uninfected cells. The arrows indicate the cells infected by HSV-2; the Hoechst nuclear staining is light grey.

FIG. 10b positive infection controls with HSV-1; FIG. 10c positive infection control with HSV-2; effect of purified Fabs on HSV-1 and HSV-2, respectively: Fab Ex2 vs HSV-1 (10d), Fab Ex2 vs HSV-2 (10e); Fab Ex2B vs HSV-1 (10f), Fab Ex2B vs HSV-2 (10g);

Fab Ex2C vs HSV-1 (10h), Fab Ex2C vs HSV-2 (10i); Fab Ex2H vs HSV-1 (10l), Fab Ex2H vs HSV-2 (10m), Ex2I vs HSV-1 (10n), and Fab Ex2I vs HSV-2 (10o).

Figure 11:
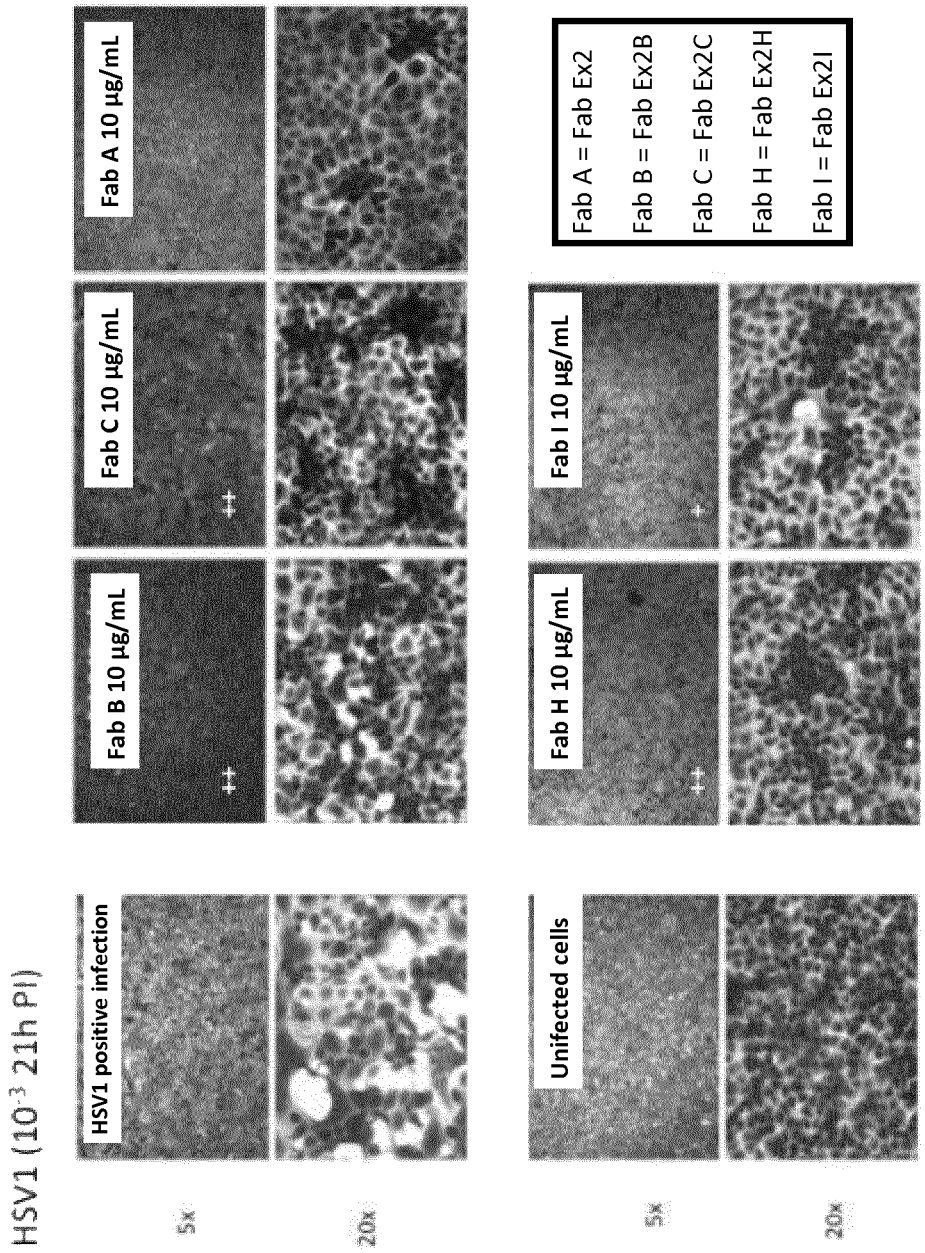
Figure 11:
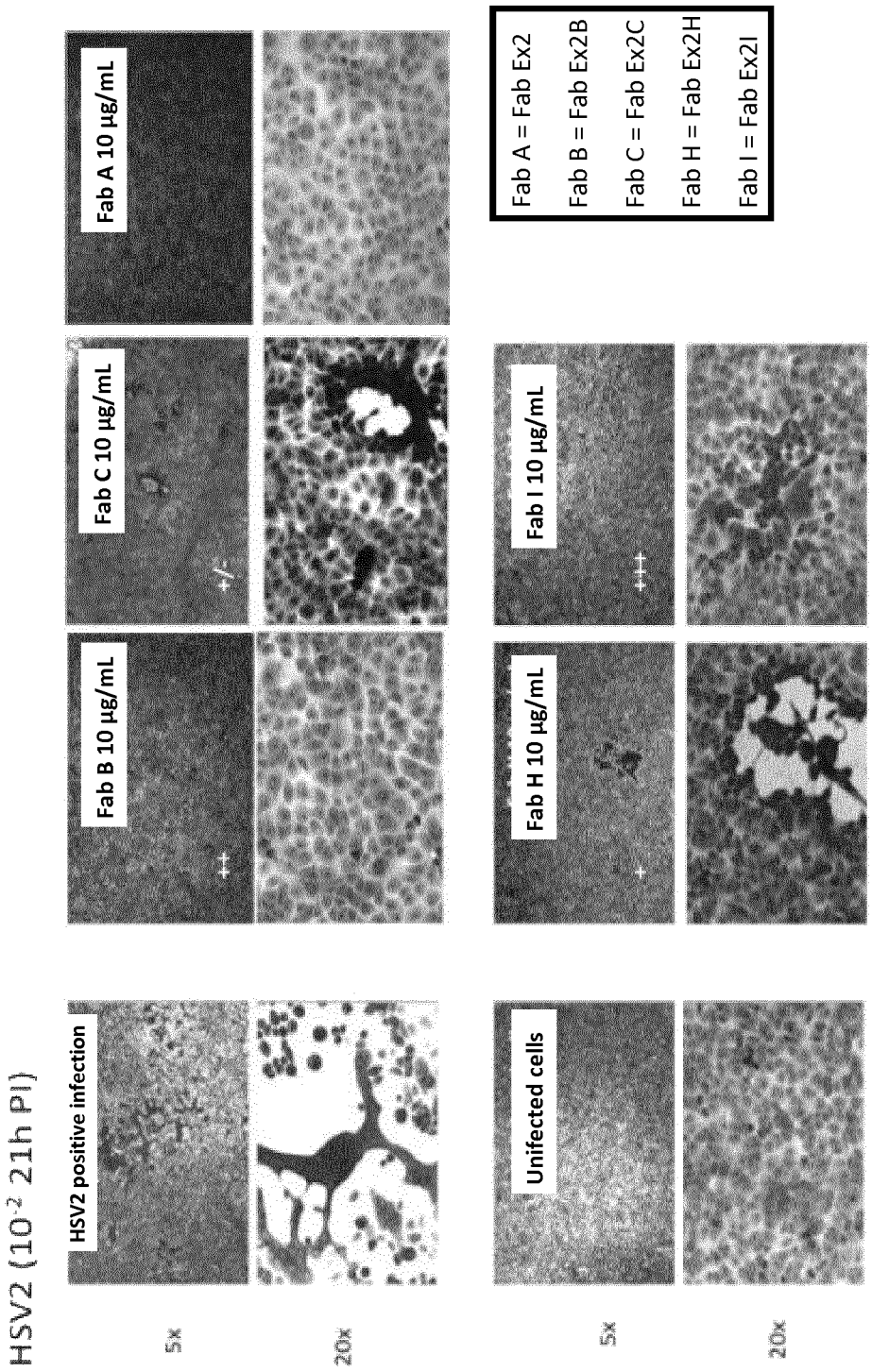

FIG. 11 shows a 5 times (5×) and 20 times (20×) magnification. The qualitative neutralization activity against HSV-1 and HSV-2 was evaluated through the syncytia formation assay (21 h post-infection). The images show—positive infection (HSV-1 virus alone), uninfected cells, effect of Fab Ex2B, Fab Ex2C, Fab Ex2, Fab Ex2H and Fab Ex2I (10 µg/mL).

Figure 12:
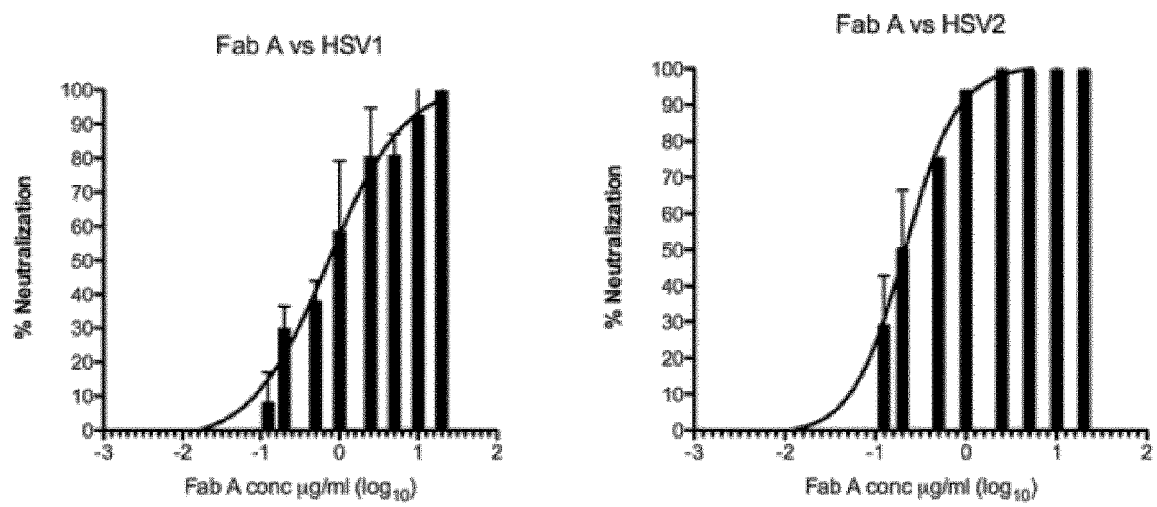

FIG. 12 illustrates the dose-response curves of Fab Ex2 neutralizing activity evaluation against HSV-1 and HSV-2 (IIF assay), as discussed in the experimental section. Fab Ex2 reduced by 50% the HSV cytopathic effect on the infected cell monolayers at very low concentrations (lower than 5 µg/mL for both HSV-1 and HSV-2 tested isolates). The X axis indicates the Fab concentrations expressed as [Log 10*(µg/mL of mAb)]. (CI=confidence interval)

Figure 13:
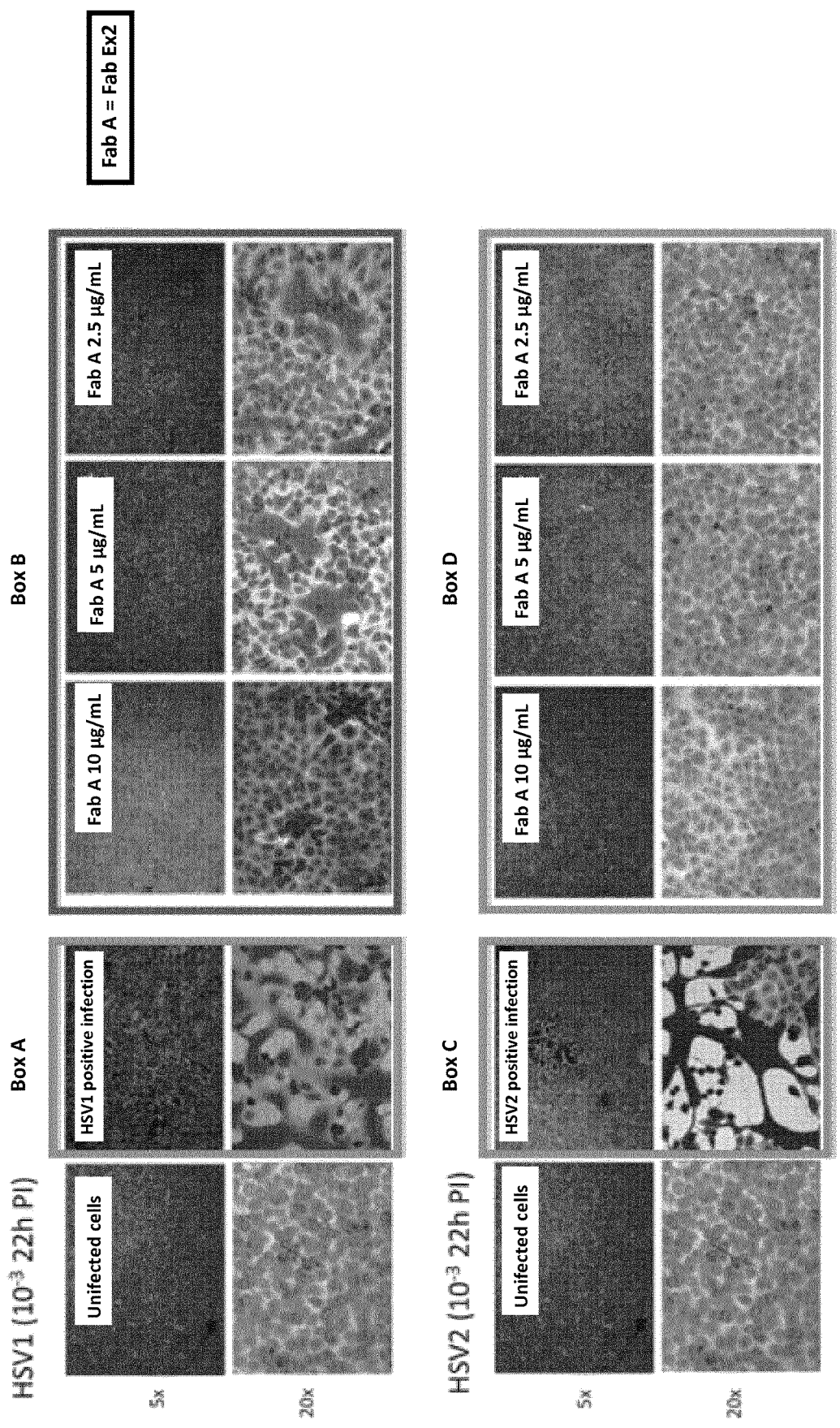

FIG. 13 shows the 5 times (5×) and 20 times (20×) magnification photos of a qualitative dose-response neutralizing activity evaluation through the syncytia formation assay against HSV-1 and HSV-2. The images represent—uninfected cells, positive infection (virus alone), effect of 10 µg/mL Fab Ex2, 5 µg/mL Fab Ex2, 2.5 µg/mL Fab Ex2.

Boxes A and C highlight the total disruption of cell monolayers by a high amount of HSV-1 or HSV-2. The Fab Ex2 dose-dependent strong inhibition of the cytopathic effect in HSV-1 infected cells is highlighted by the B box. The complete inhibition of HSV-2 infection is highlighted by the D box.

Figure 14:
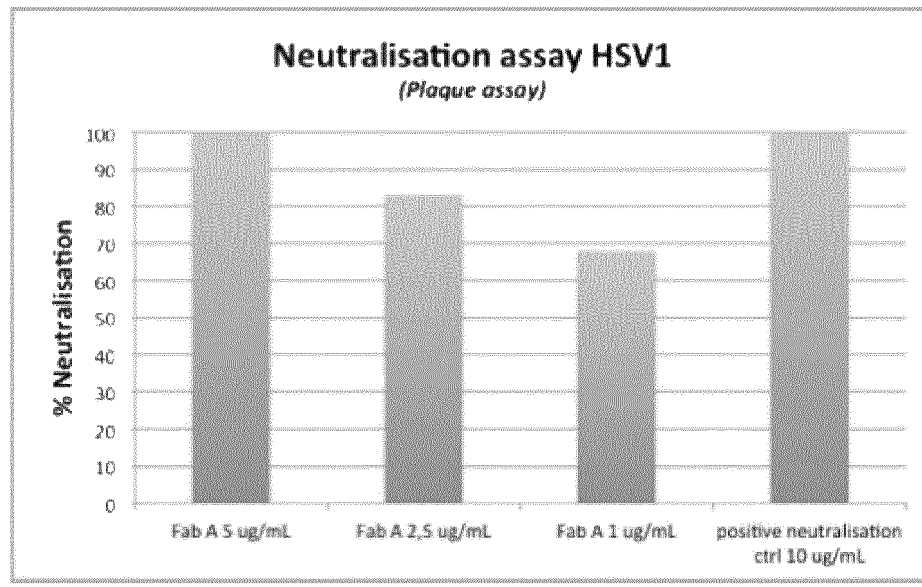
Figure 14:
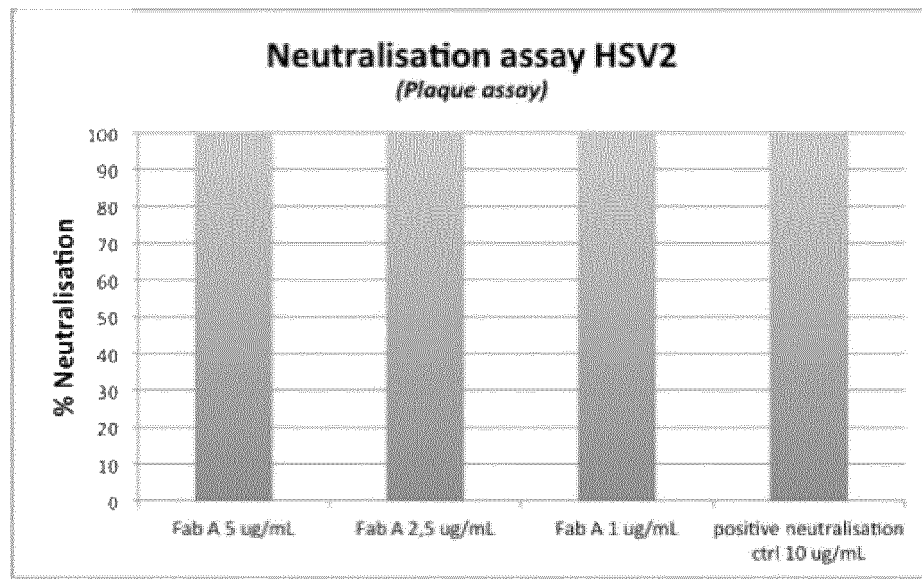

FIG. 14 illustrates the neutralizing activity against both HSV-1 and HSV-2 isolates of Fab Ex2 by plaque reduction assay. Fab Ex2 was tested at the concentrations of 5 µg/mL, 2.5 µg/mL and 1 µg/mL. Fab Ex2 completely prevented HSV-2 infection even at the lowest concentration tested (1 µg/mL).

Figure 15A:
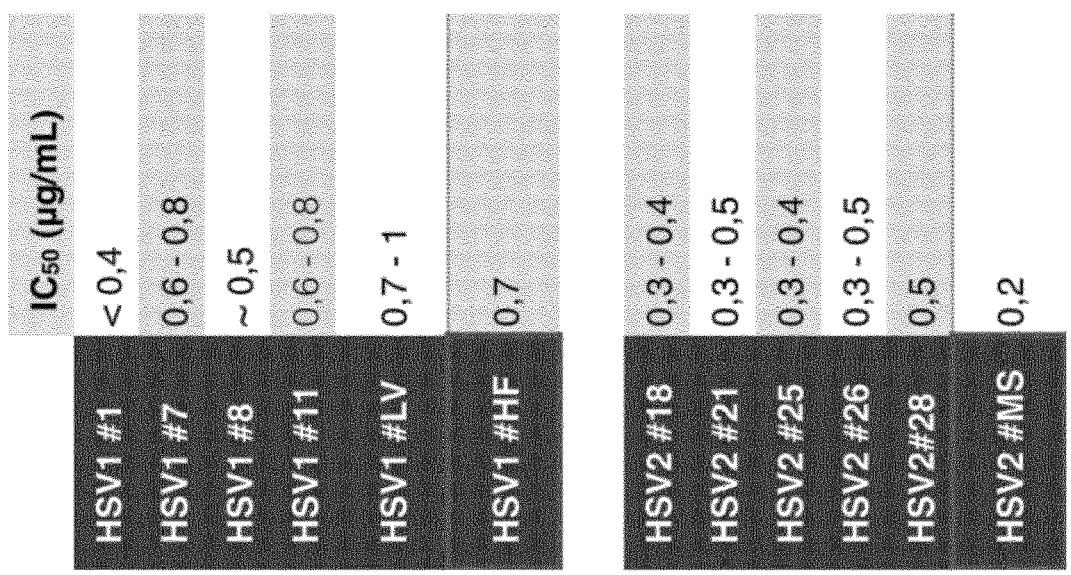
Figure 15A:
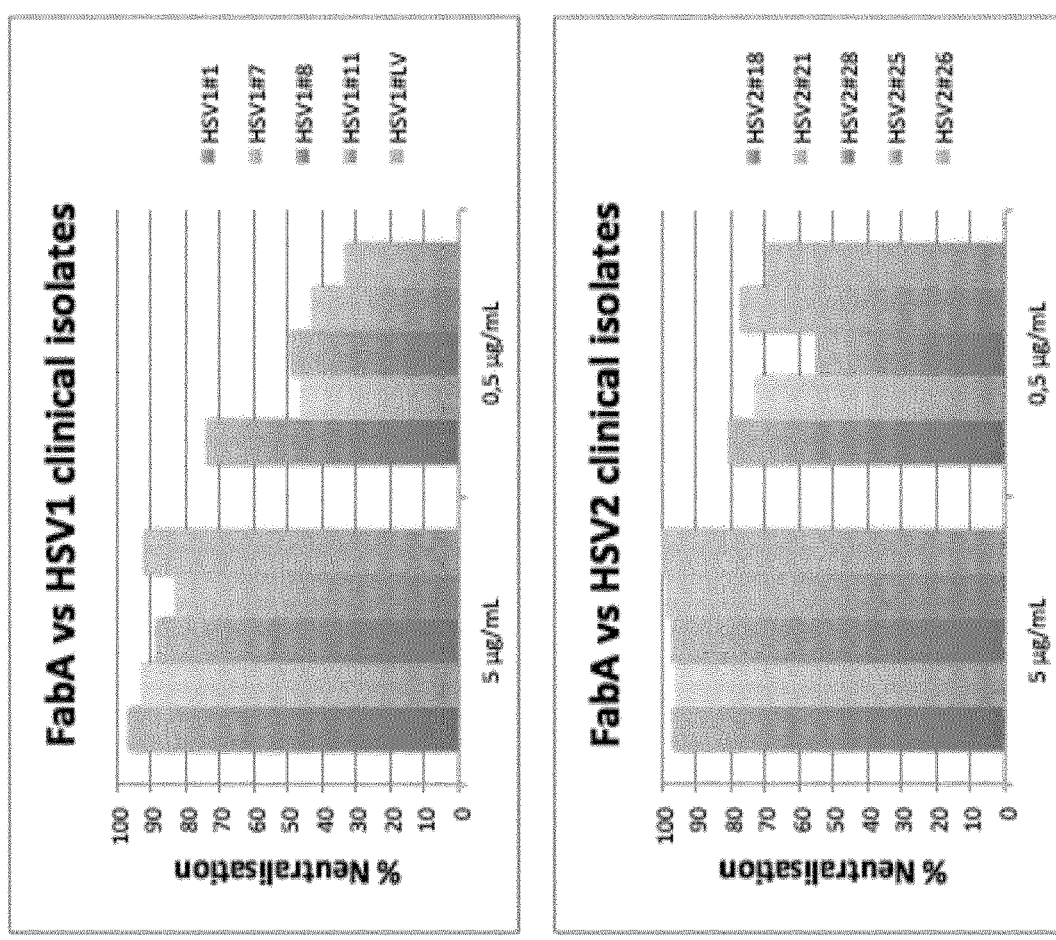
Figure 15A:
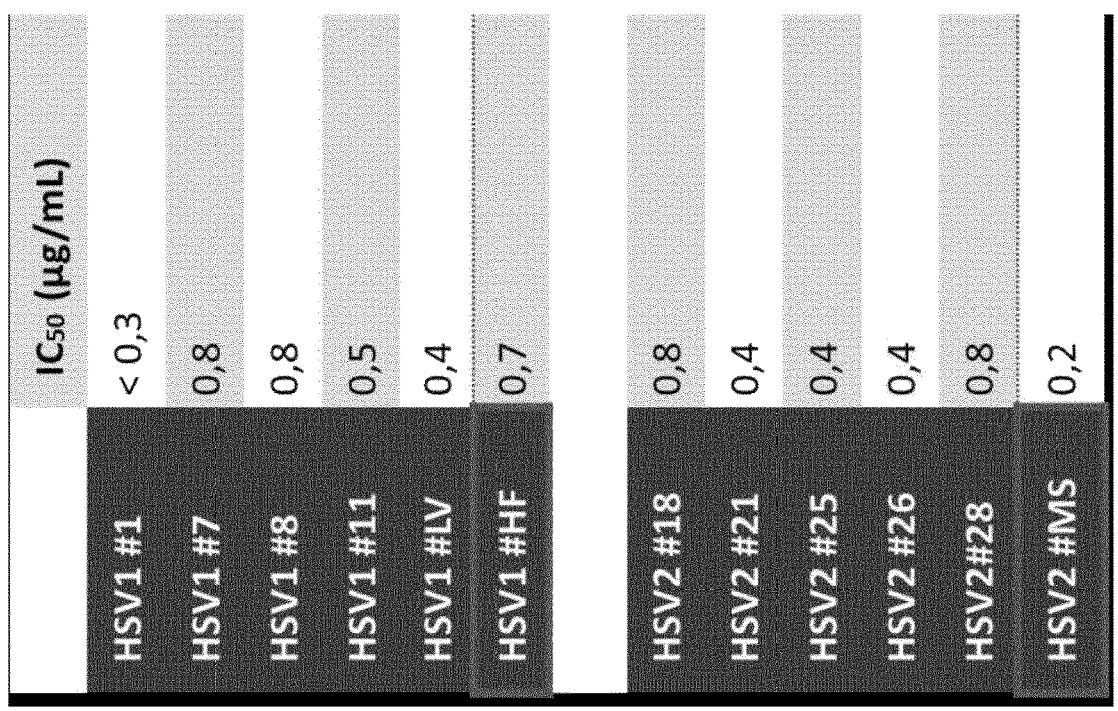
Figure 15A:
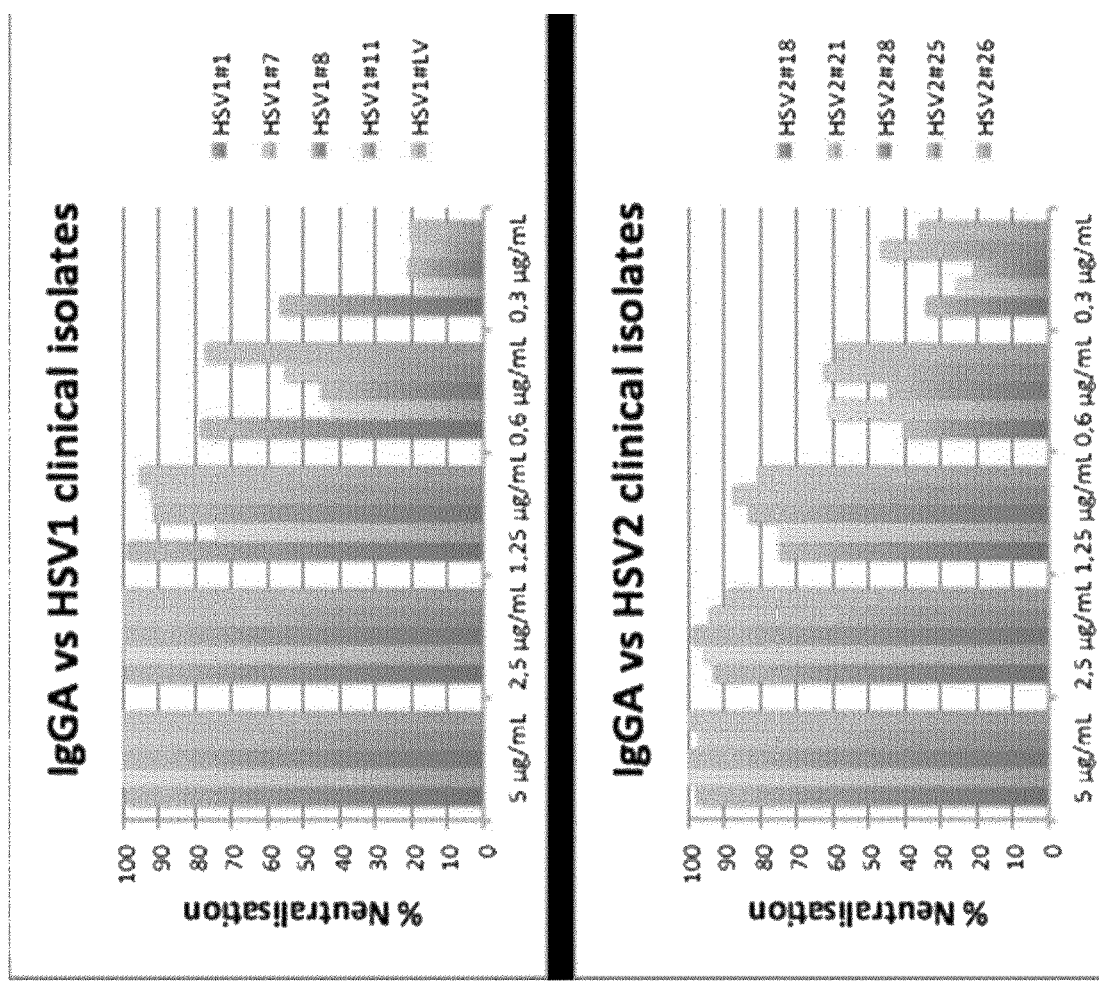

FIG. 15A Neutralising activity of IgG A against HSV1 and HSV2 isolates featuring different susceptibility to Acyclovir. The table on the right shows the $IC_{50}$s of IgG A against clinical isolates of HSV. Red boxes indicate HSV 1 and 2 reference strains.

Figure 15B:
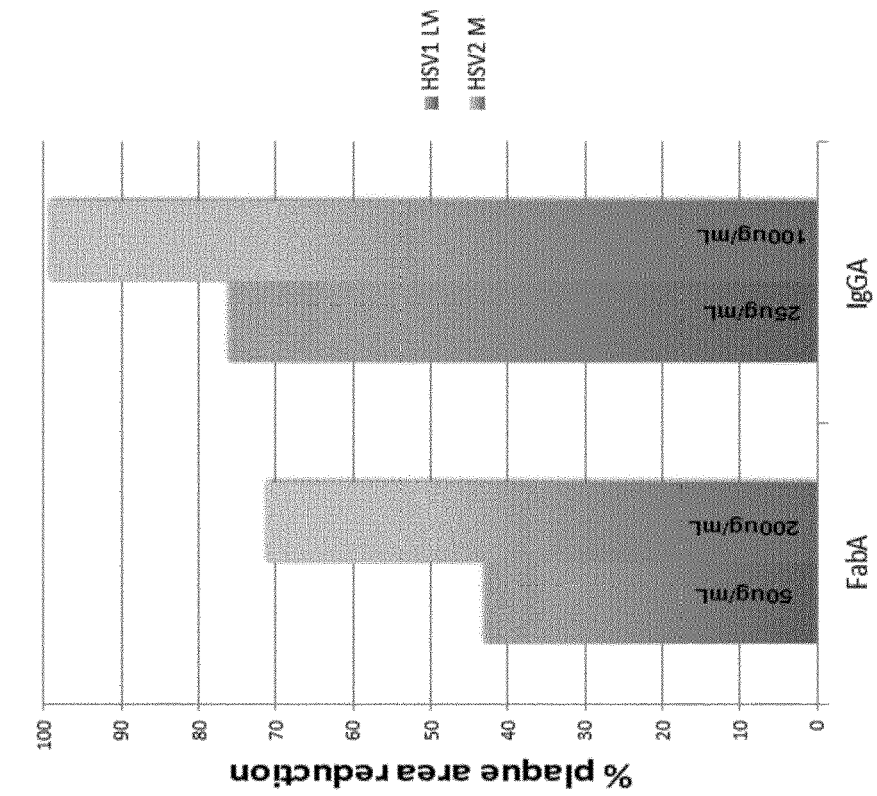
Figure 15B:
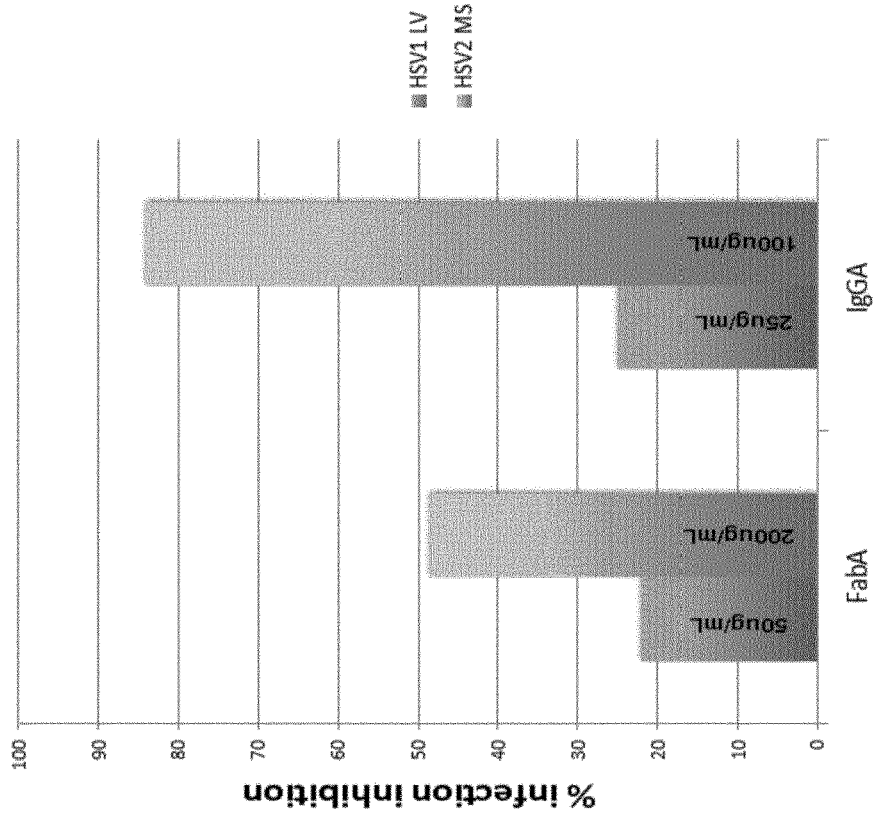

FIG. 15B Comparison of biological activity for Fab A and IgG A used in post adsorption assays (viral progeny neutralization and cell to cell spreading inhibition.

Figure 16A:
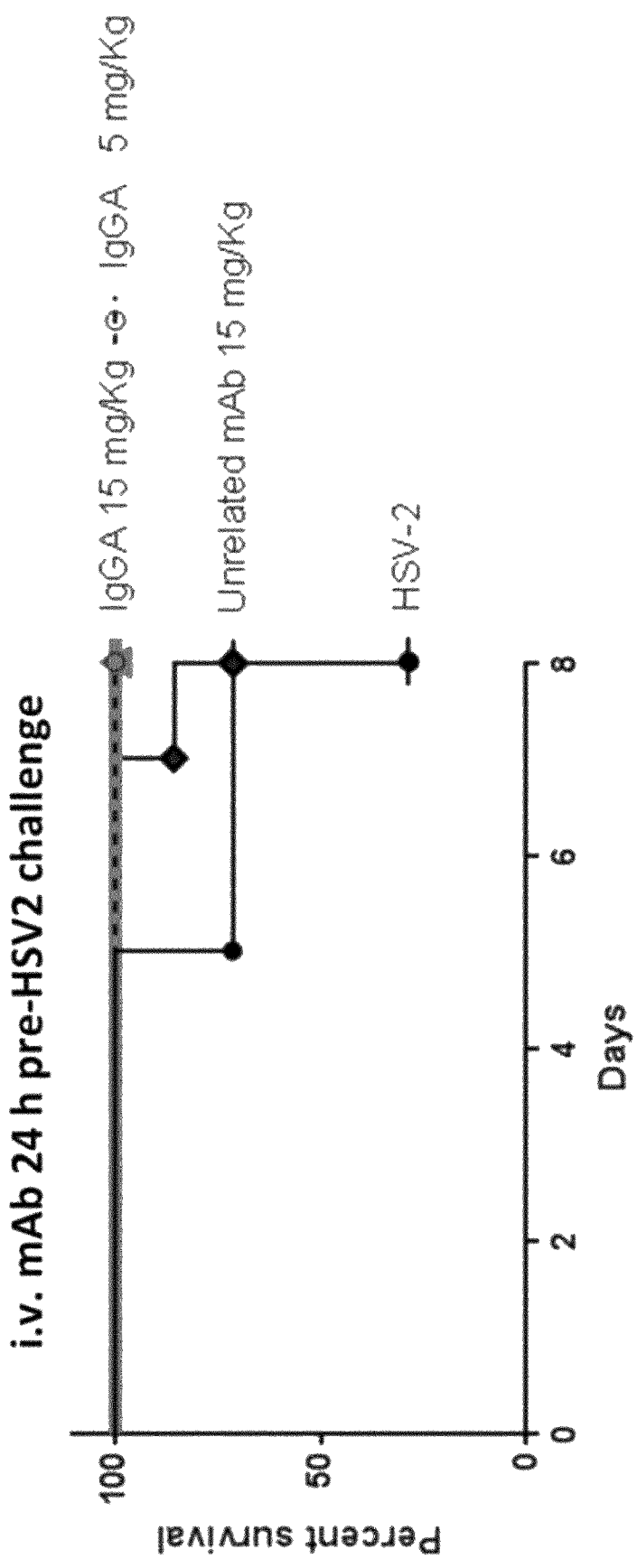

FIG. 16A Kaplan-Meier survival curves. The graph shows the survival rate of mice treated with a single systemic administration of IgGA at two different concentrations (15 mg/kg and 5 mg/kg) against HSV-2 challenge 24 hours before virus lethal challenge (controls included in the graph as well).

Figure 16B:
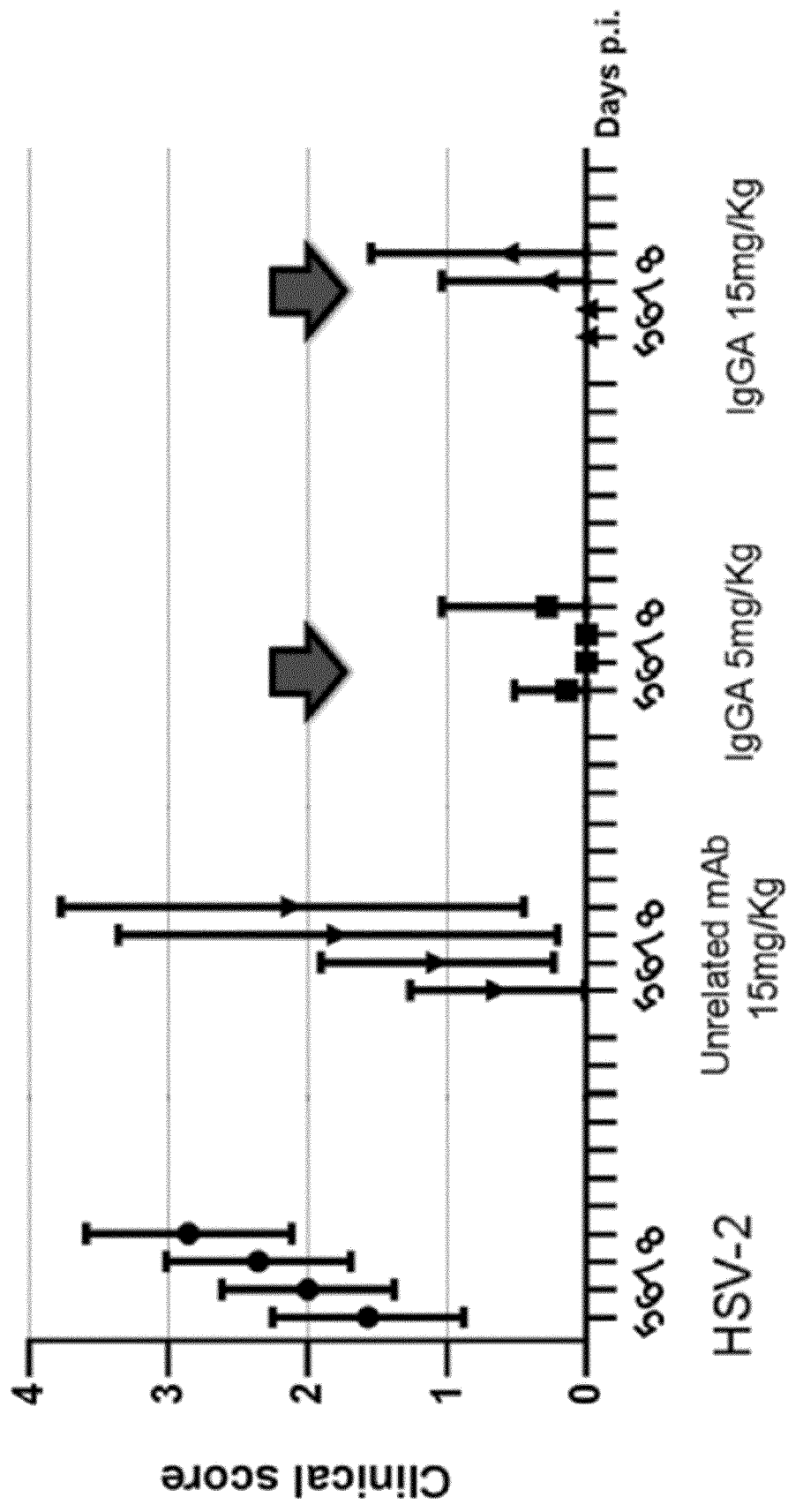

FIG. 16B Clinical scores evaluation of mice treated with a single systemic administration of IgGA at two different concentrations (15 mg/kg and 5 mg/kg) against HSV-2 challenge 24 hours before virus lethal challenge. IgGA FIG. 16C Clinical signs of mice treated with a single systemic administration of IgGA at two different concentrations (15 mg/kg and 5 mg/kg) against HSV-2 challenge 24 hours before virus lethal challenge.

Figure 17A:
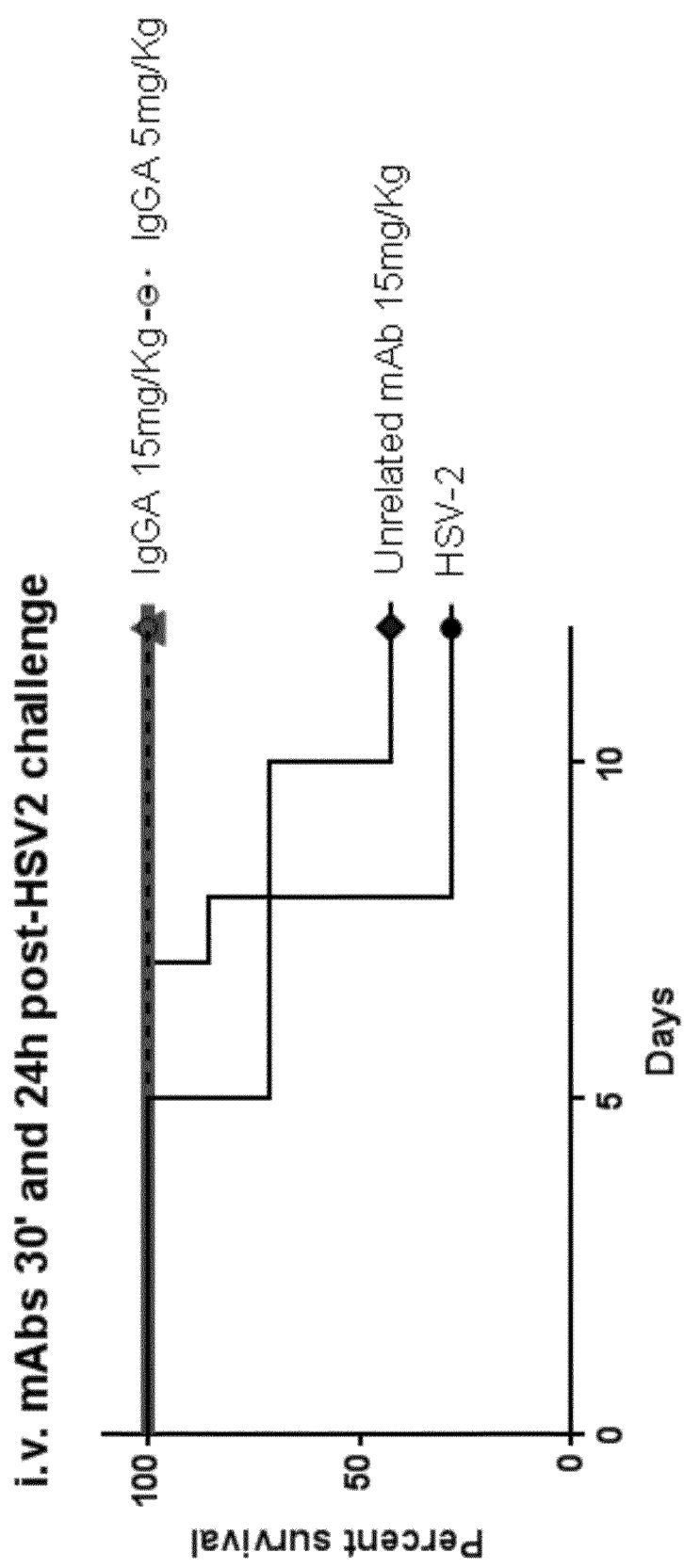

IgGA FIG. 17A Kaplan-Meier survival curves. The graph shows the full protection (in terms of percent survival rate) of mice of both dose groups against HSV-2 challenge (at 30 minutes and 24 h post-infection).

Figure 17B:
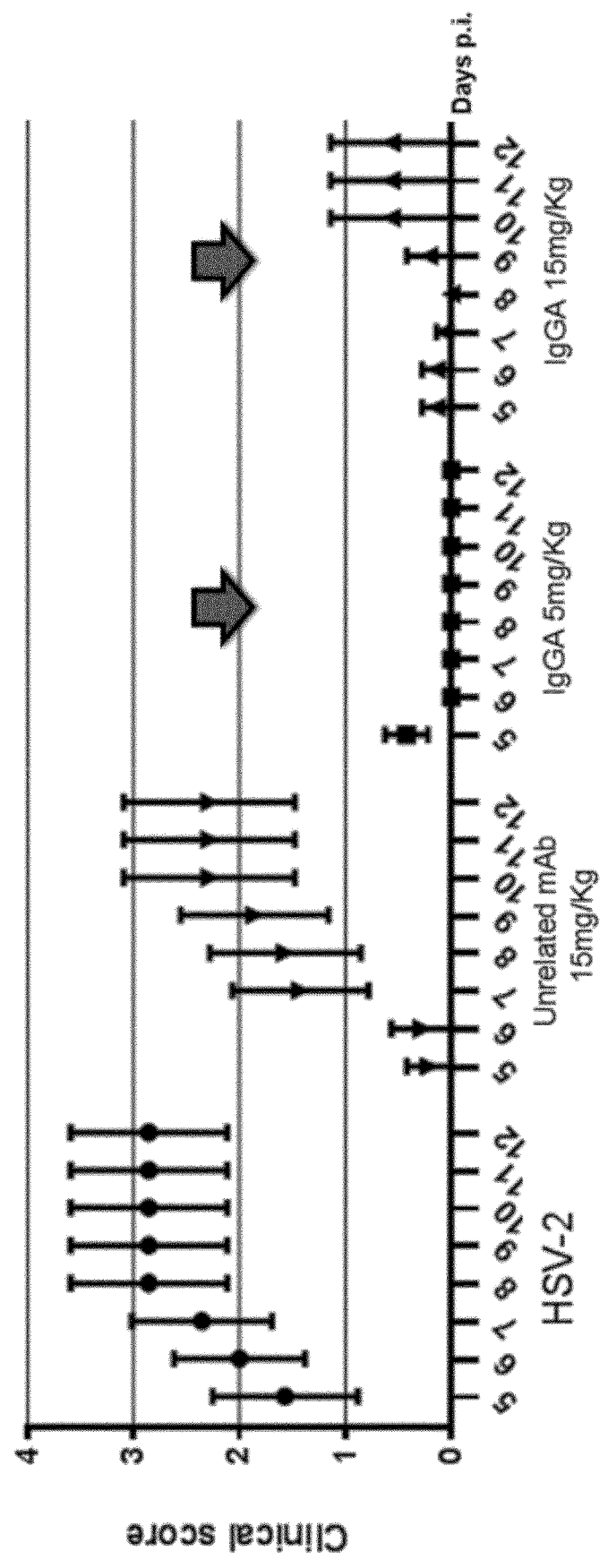

IgGA FIG. 17B Clinical scores evaluation of mice of both dose groups against HSV-2 challenge (at 30 minutes and 24 h post-infection).

Figure 17C:

FIG. 17C Clinical signs of mice of both dose groups against HSV-2 challenge (at 30 minutes and 24 h post-infection).

Figure 18A:
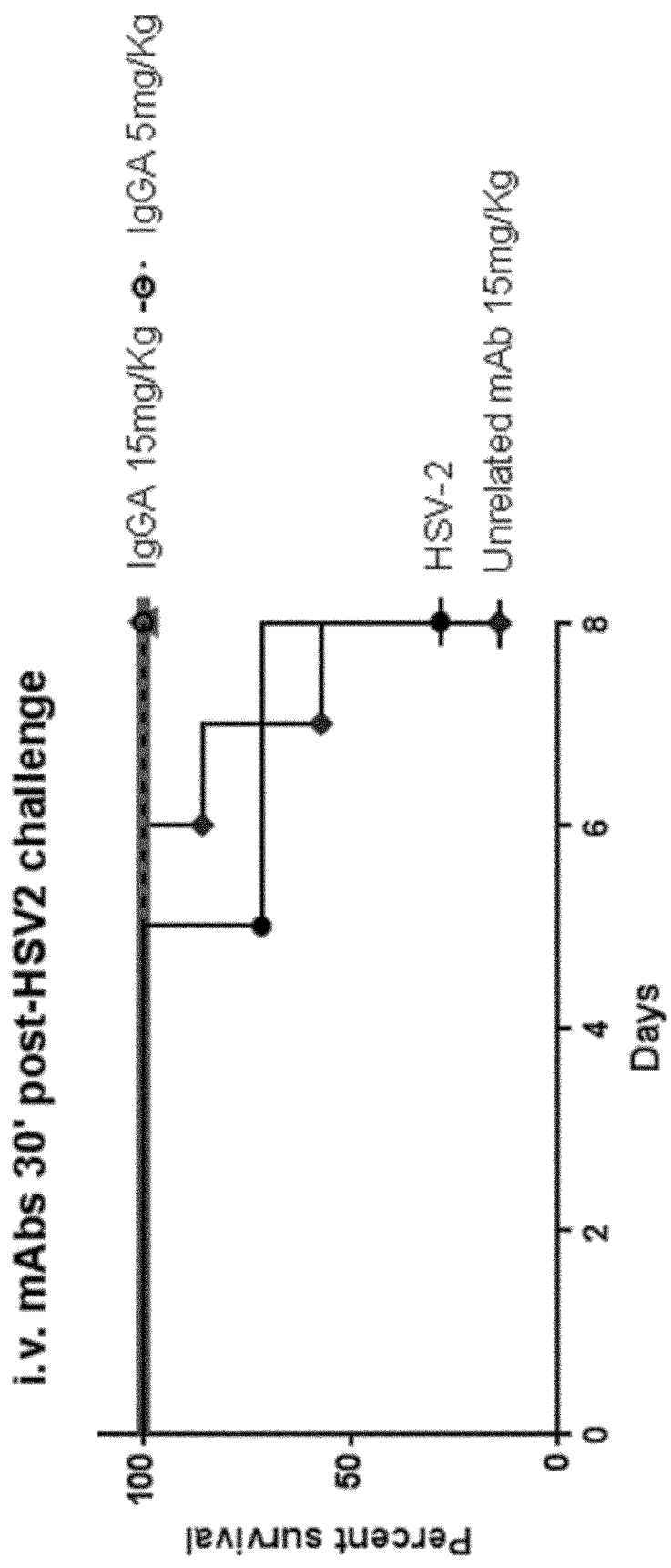

IgGA FIG. 18A Kaplan-Meier curve: Survival rate of murine cohorts treated with IgGA (single injection) 30 minutes after the HSV-2 challenge.

Figure 18B:
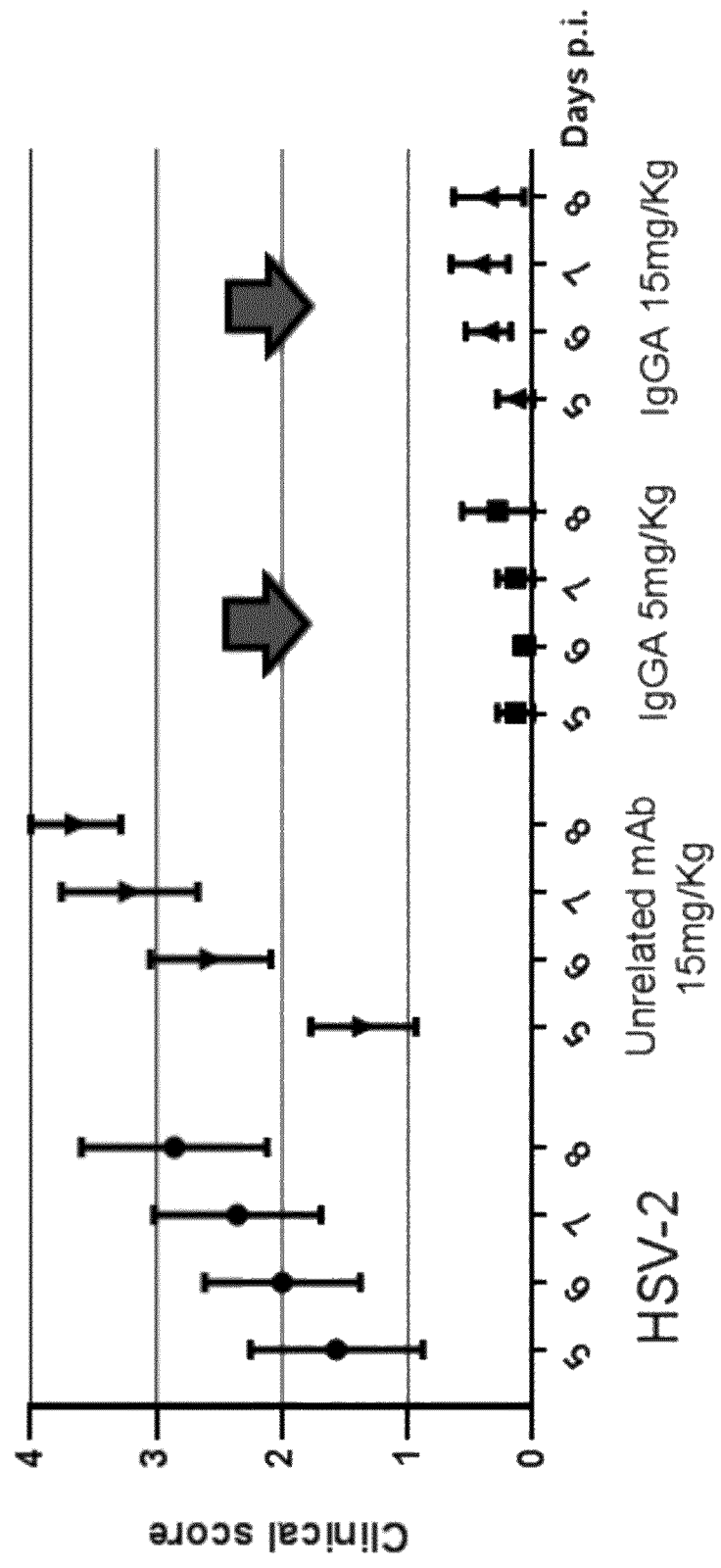

FIG. 18B Clinical score evaluation of murine cohorts treated with IgGA (single injection) 30 minutes after the HSV-2 challenge. Mice receiving either IgGA concentration did not show any HSV clinical sign.

Figure 18C:
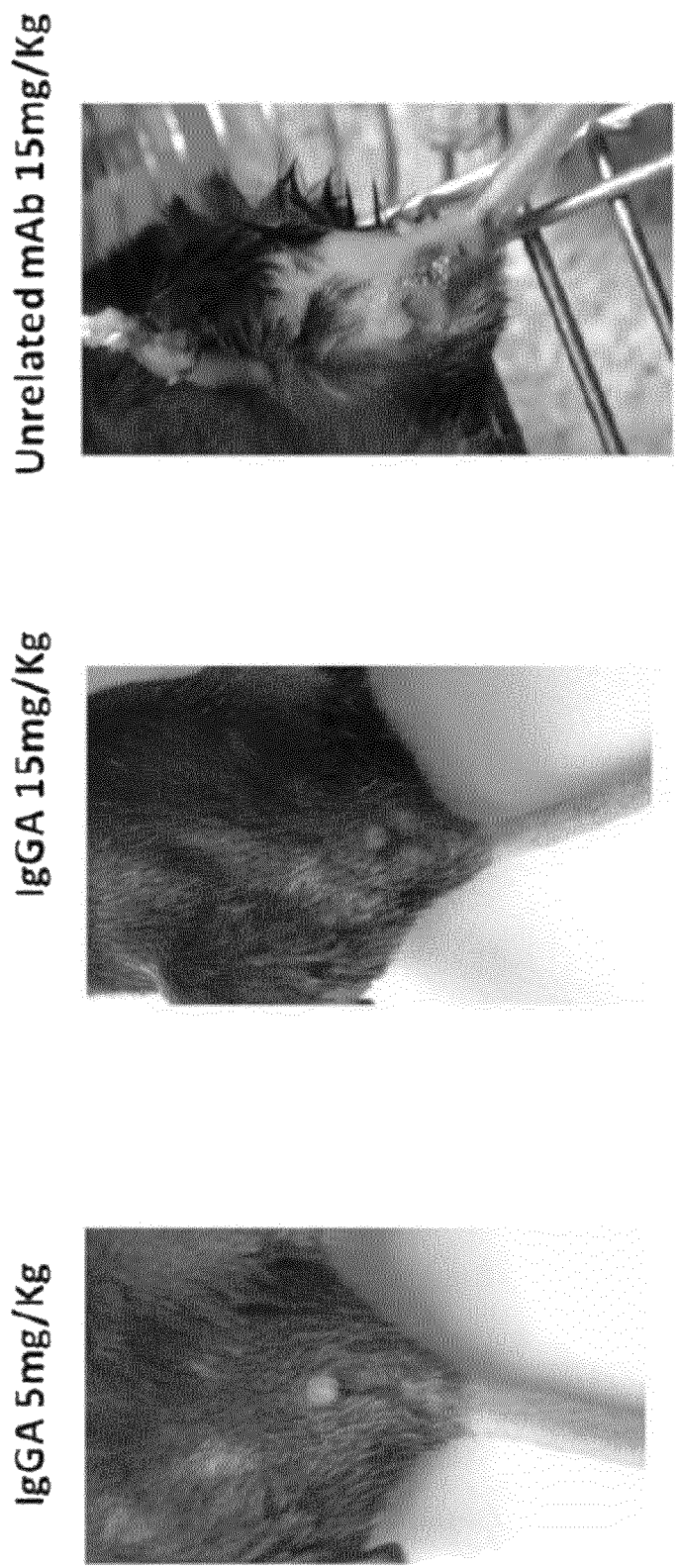

FIG. 18C Clinical signs of murine cohorts treated with IgGA (single injection) 30 minutes after the HSV-2 challenge. Mice receiving either IgGA concentration did not show any HSV clinical sign.

Figure 19A:
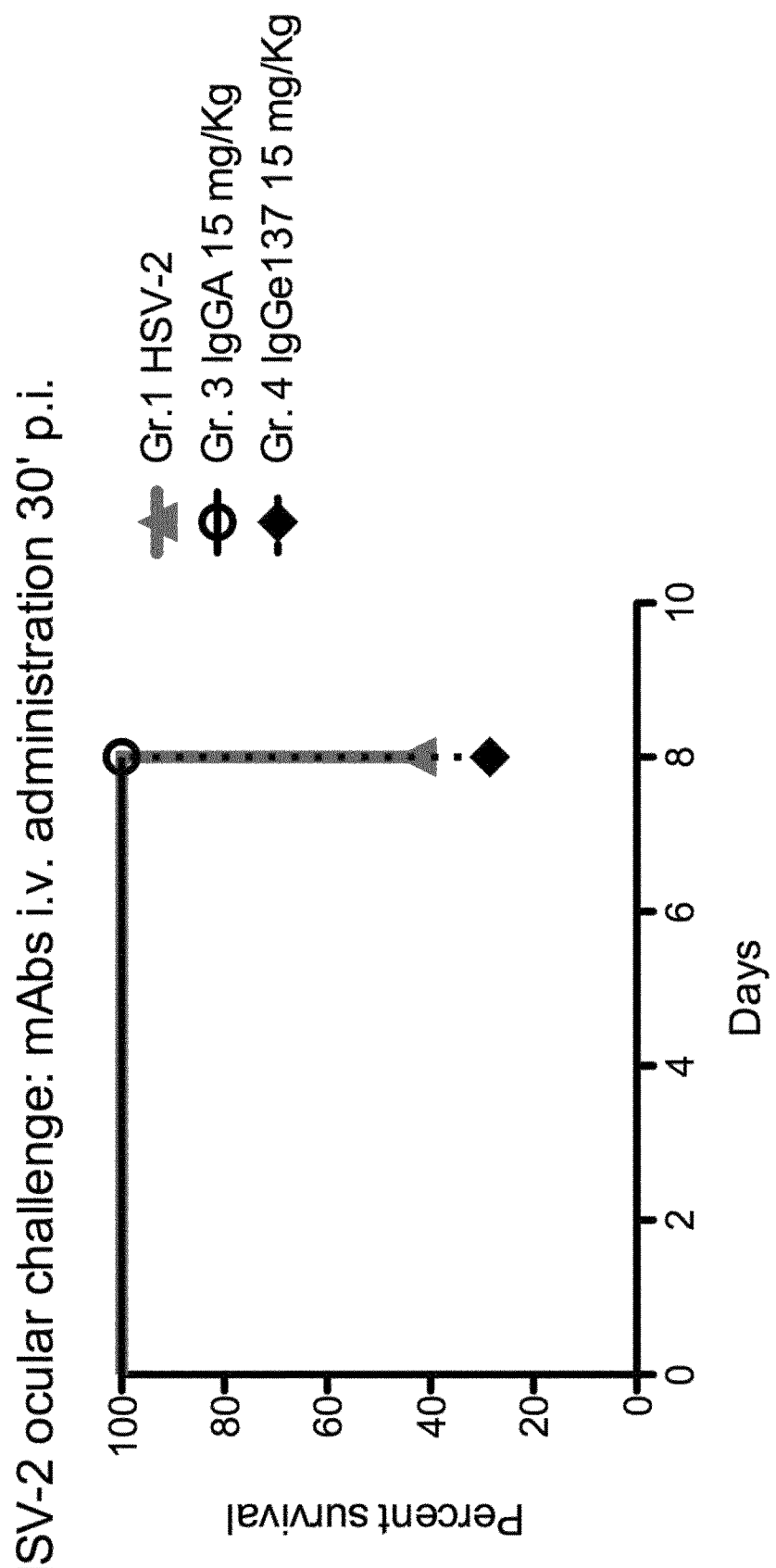

FIG. 19A Kaplan-Meier curve: Survival rate of mice treated with systemic administration (single administration) of IgGA after against HSV-2 ocular lethal challenge.

Figure 19B:
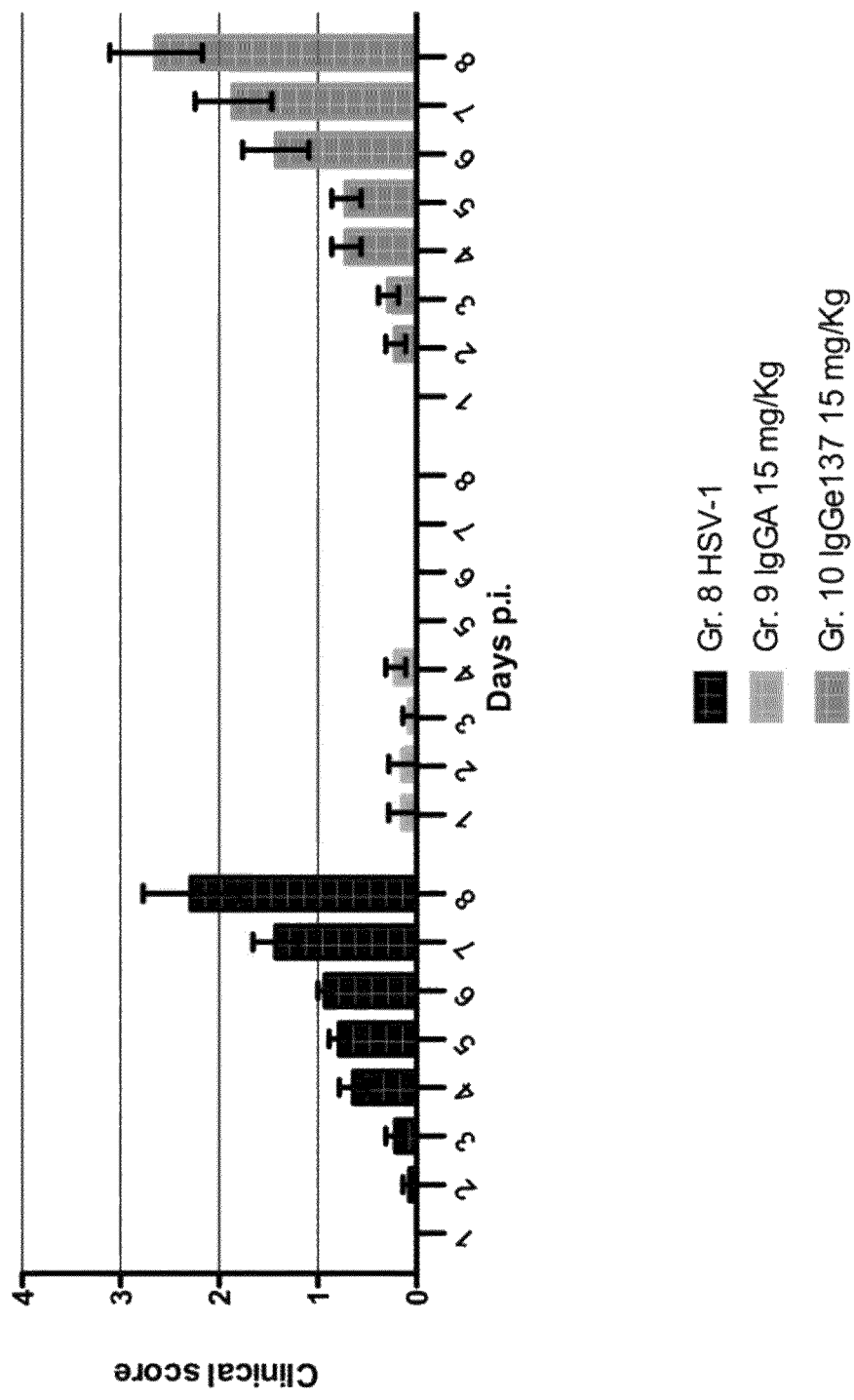
Figure 19B:
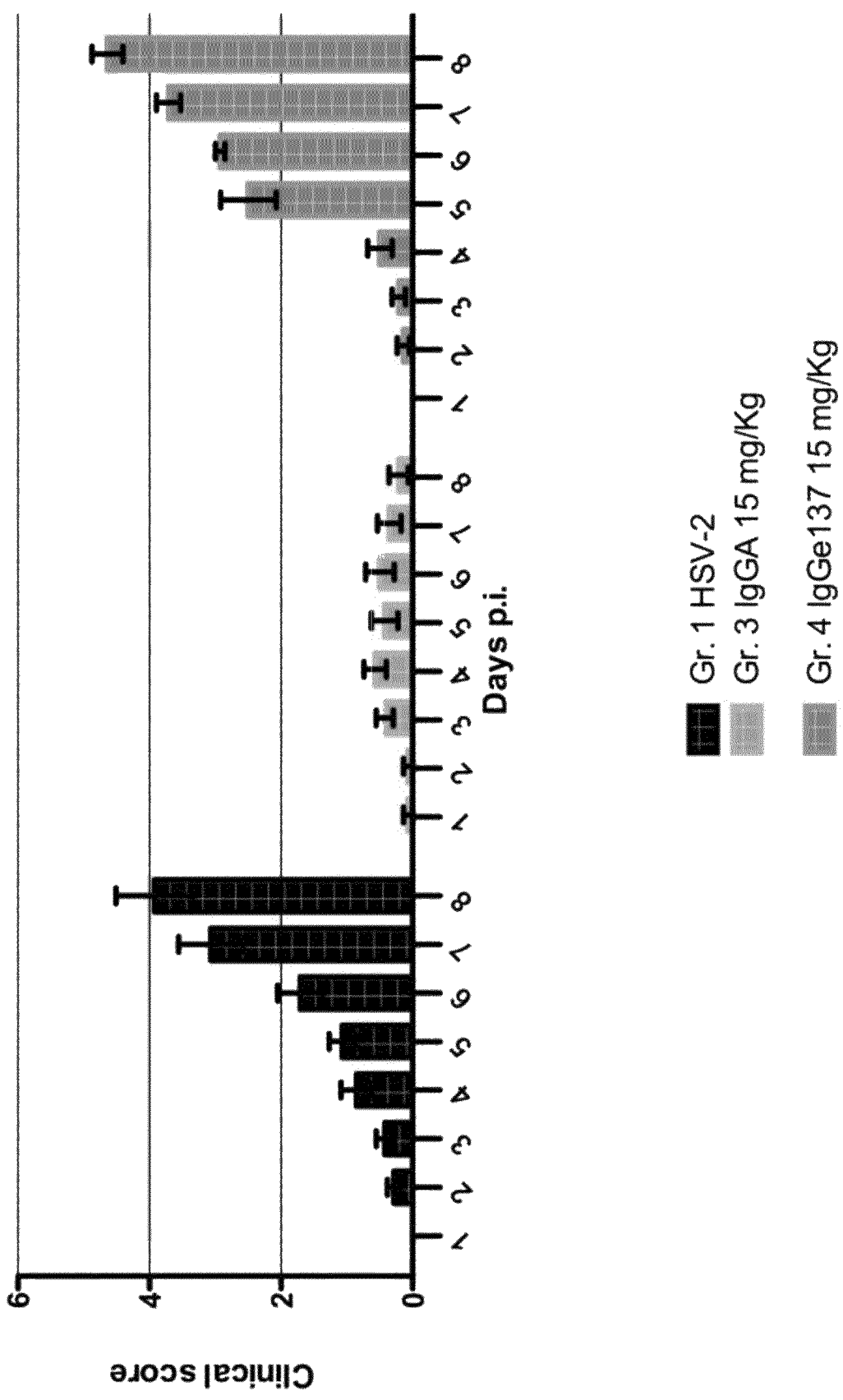

FIG. 19B Clinical scores evaluation of murine cohorts treated with systemic administration of IgGA (single administration) after the HSV-2 or HSV-1 challenge ocular lethal challenge. The "Y" axis shows the clinical scores above described. Each value on the graph represents mean±SEM of the total clinical scoring (0 to 5) for each mice group.

Figure 19C:
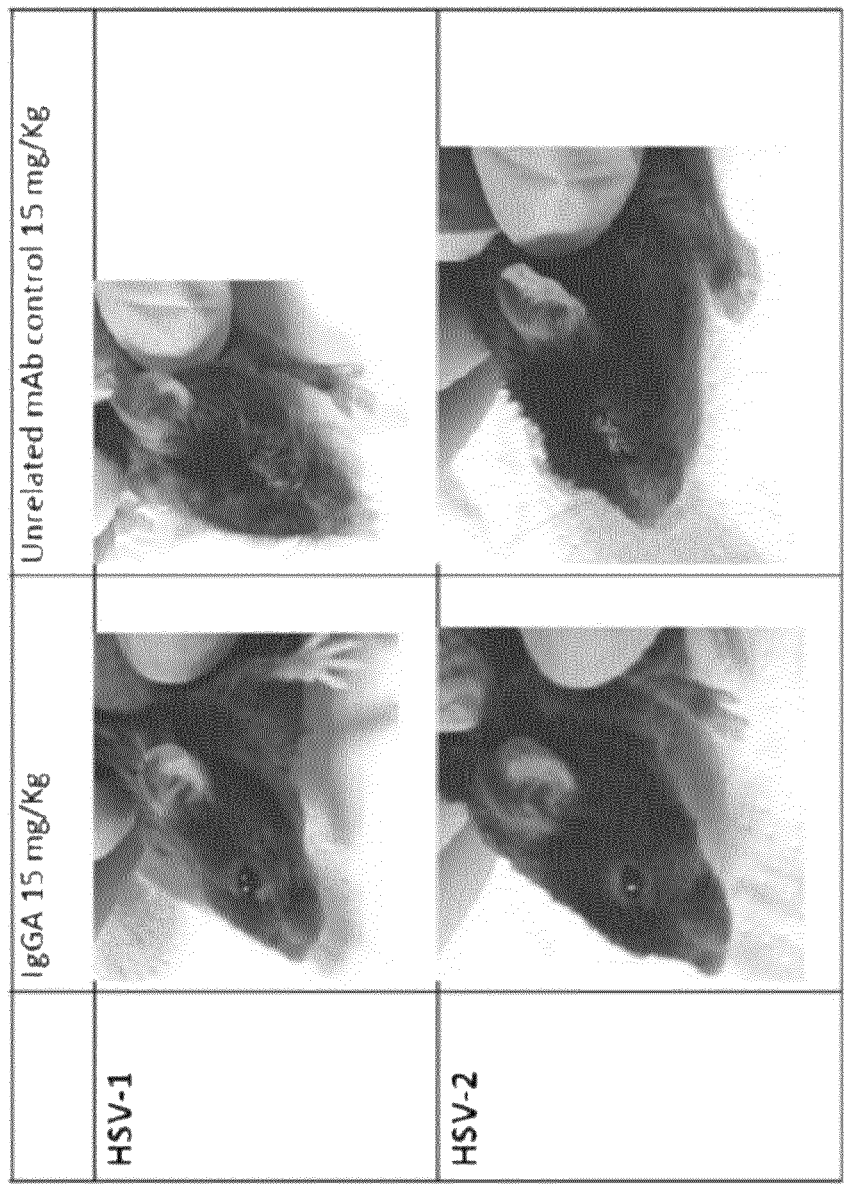

FIG. 19C Clinical signs of murine cohorts treated with IgGA.

DETAILED DESCRIPTION OF THE INVENTION

The present invention concerns monoclonal antibodies and fragments of said antibodies which bind to HSV-1 and HSV-2, and which can inhibit the HSV infectivity.

In a first aspect, the present inventions relates to an HSV-1 and HSV-2 binding monoclonal antibody or an antigen-binding fragment thereof comprising both a heavy ($V_H$) and a light chain ($V_L$) variable region, said antibody or fragment thereof comprising a complementary determining region (CDR) chosen from the group consisting of SEQ ID NO. 3, SEQ ID NO. 6, SEQ ID NO. 9, and SEQ ID NO. 12. The Complementarity Determining Regions (CDRs) are part of the variable chains in immunoglobulins (antibodies), where these molecules bind to their specific antigen. CDRs correspond to the most variable parts of the molecules, and are crucial to the diversity of antigen specificities generated by lymphocytes.

One of the advantages of the CDR sequences according to the present invention is that they allow a very specific binding affinity of the antibodies or fragments of said antibodies to the HSV both of type 1 (HSV-1) and of type 2 (HSV-2).

The monoclonal antibodies according to the present invention in fact show an HSV inhibition capacity of over 50% even at very low concentrations. Without being bound to any theory, this specificity and high viral neutralization capacity can also be attributed to the CDR sequences.

In a further aspect the present invention relates to an HSV-1 and HSV-2 binding monoclonal antibody or fragment thereof, wherein said heavy chain ($V_H$) variable region is chosen from the group consisting of SEQ ID NO.1, SEQ ID N.4, SEQ ID NO.7, and SEQ ID NO.10, or direct equivalents thereof.

Direct equivalents of the heavy chain variable regions, as used herein refer to sequences which preferably have at least 95% overall sequence similarity, homology or identity with said $V_H$ variable regions and are capable of inhibiting by 50% the activity of both HSV-1 and/or HSV-2 at a concentration lower than 5 µg/ml, independently of each other.

The direct equivalents of the $V_H$ variable regions according to the present invention have at least 96%, 97% 98% or 99% overall sequence similarity or homology. In a further aspect the invention relates to an HSV-1 and HSV-2 binding monoclonal antibody or fragment thereof, wherein said light chain ($V_L$) variable region is chosen from the group consisting of SEQ ID NO. 2, SEQ ID NO.5, SEQ ID NO.8, SEQ ID NO.11, and SEQ ID NO.13, or direct equivalents thereof.

Direct equivalents of the light chain variable regions, as used herein refer to sequences which preferably have at least 95% overall sequence similarity, homology or identity with said $V_L$ variable regions and are capable of inhibiting by 50% the activity of both HSV-1 and/or HSV-2 at a concentration of less than 5 μg/ml, independently of each other.

The direct equivalents of the $V_L$ variable regions according to the present invention have at least 96%, 97% 98% or 99% overall sequence similarity or homology. In the present invention:

the term "HSV" as used herein refers to Herpes Simplex Viruses. There are two types of HSV, namely HSV-1 and HSV-2 which show similar characteristics.

the term "fragment" of antibodies which bind to HSV-1 and/or to HSV-2, as used herein refers to Fab, or single chain antibody fragments which have smaller size with respect to the corresponding antibody.

For the purposes of the present invention, each antibody region has a corresponding SEQ ID NO., as follows:

SEQ ID NO.1 corresponds to the amino acidic sequence of the heavy chain ($V_H$) variable region of the VH1 antibody, also identified as Fab Ex2;

SEQ ID NO.2 corresponds to the amino acidic sequence of the light chain ($V_L$) variable region of the VH1 antibody, also identified as Fab Ex2;

SEQ ID NO.3 corresponds to the amino acidic sequence of the complementary determining regions of the VH1 antibody, also identified as Fab Ex2; SEQ ID NO.4 corresponds to the amino acidic sequence of the heavy chain ($V_H$) variable region of the VH3 antibody, also identified as Fab Ex2B and of the VH51, also identified as Fab Ex2I SEQ ID NO.5 corresponds to the amino acidic sequence of the light chain ($V_L$) variable region of the VH3 antibody, also identified as Fab Ex2B;

SEQ ID NO.6 corresponds to the amino acidic sequence of the complementary determining regions of the VH3 antibody, also identified as Fab Ex2B and of the VH51, also identified as Fab Ex2I;

SEQ ID NO.7 corresponds to the amino acidic sequence of the heavy chain ($V_H$) variable region of the VH5 antibody, also identified as Fab Ex2C;

SEQ ID NO.8 corresponds to the amino acidic sequence of the light chain ($V_L$) variable region of the VH5 antibody, also identified as Fab Ex2C;

SEQ ID NO.9 corresponds to the amino acidic sequence of the complementary determining regions of the VH5 antibody, also identified as Fab Ex2C;

SEQ ID NO.10 corresponds to the amino acidic sequence of the heavy chain ($V_H$) variable region of the VH47 antibody, also identified as Fab Ex2H;

SEQ ID NO.11 corresponds to the amino acidic sequence of the light chain ($V_L$) variable region of the VH47 antibody, also identified as Fab Ex2H;

SEQ ID NO.12 corresponds to the amino acidic sequence of the complementary determining regions of the VH47 antibody, also identified as Fab Ex2H;

SEQ ID NO.13 corresponds to the amino acidic sequence of the light chain ($V_L$) variable region of the VH51 antibody, also identified as Fab Ex2I.

The order in which the heavy and light chains are present in each single chain antibody may be inverted, thus a single chain antibody may be formed by a heavy chain—light chain or by a light chain—heavy chain, and the activity cannot be envisaged a priori on the basis of the chain succession.

Advantageously, the monoclonal antibodies according to the present invention can be used and are efficacious in immune-compromised individuals such as cancer patients and transplant recipients, and in immune-deficient patients.

Advantageously, the monoclonal antibodies according to the present invention can be used and are efficacious in newborn infants.

In a preferred embodiment, the present invention provides the HSV-1 and HSV-2 binding monoclonal antibody or fragment thereof, wherein said antibody has a heavy chain ($V_H$) variable region of SEQ ID NO.1 and a light chain ($V_L$) variable region of SEQ ID NO.2.

Presently, acyclovir (acycloguanosine) is used for the treatment of HSV infection. Unfortunately, not in all cases acyclovir is effective in controlling virus replication and infection. Acyclovir, in fact, is ineffective when used to treat infections caused by resistant viral variants or, in the case in which new mutations of viral tyrosine kinase (TK) confer resistance to this drug.

As discussed previously, among the antiviral drugs used to treat acyclovir-resistant HSV infections, of great importance are foscarnet (phosphonoformic acid) and cidofovir, a nucleotide analogue. After undergoing cellular phosphorylation to its diphosphate form, cidofovir competitively inhibits the incorporation of deoxycytidine triphosphate into viral DNA by viral DNA polymerase. Incorporation of the drug disrupts further chain elongation. Cidofovir is not phosphorylated (and hence activated) by a viral kinase unlike nucleoside analogues such as acyclovir or ganciclovir.

More in details, as already discussed and noted above, currently available anti-herpes drugs are burdened by clinical relevant drawbacks. More in details, acyclovir drug resistance infers cross-resistance to other anti-herpes drugs, consequently there are no other oral therapeutic options to treat HSV infection. Alternative intravenous and topical options include formulations of foscarnet and cidofovir which are burdened by side effects. Although vidarabine (a purine analogue that preferentially inhibits viral DNA synthesis) has activity against herpes viruses, it is not effective in patients with acyclovir resistance and it is more toxic and less metabolically stable than many of the other currently used antivirals (such as acyclovir). Vidarabine also is burdened by the presence of resistant viral strains.

Finally, patients showing intolerance to foscarnet have been also described. The therapeutic options for the patients intolerant to foscarnet (used in case of acyclovir-resistant virus infection), or for patients with severe toxicity on therapy, are limited: continuous high-dose acyclovir (30 to 45 mg/kg/day) has been successfully utilized for acyclovir-resistant herpes in immune-compromised patients (ie, hematopoietic stem cell transplant recipients). Unfortunately, there are no data on this approach in HIV-infected patients; topical therapies (eg, cidofovir) may also be considered, although topical cidofovir dosing is not standardized at all.

As it will be evident from the Experimental section, the HSV-1 and HSV-2 binding monoclonal antibodies or fragments thereof, according to the present invention have a strong neutralizing activity against both HSV-1 and HSV-2, advantageously providing an alternative to the drawbacks of currently available antiviral therapies such as antiviral drugs resistance, poor efficacy and safety, contraindications or intolerance.

In a further embodiment, the present invention provides the HSV-1 and HSV-2 binding monoclonal antibody or fragment thereof, said antibody having a heavy chain ($V_H$) variable region of SEQ ID NO.4 and a light chain ($V_L$) variable region of SEQ ID NO.5.

In a still further embodiment, the present invention provides the HSV-1 and HSV-2 binding monoclonal antibody or fragment thereof, said antibody having a heavy chain ($V_H$) variable region of SEQ ID NO.7 and a light chain ($V_L$) variable region of SEQ ID NO.8.

In a still further embodiment, the present invention provides the HSV-1 and HSV-2 binding monoclonal antibody or fragment thereof, said antibody having a heavy chain ($V_H$) variable region of SEQ ID NO.10 and a light chain ($V_L$) variable region of SEQ ID NO.11.

In a still further embodiment, the present invention provides the HSV-1 and HSV-2 binding monoclonal antibody or fragment thereof, said antibody having a heavy chain ($V_H$) variable region of SEQ ID NO.4 (and a light chain ($V_L$) variable region of SEQ ID NO.13.

In a further aspect, the invention provides an HSV-1 and/or HSV-2 binding monoclonal antibody or fragment thereof, wherein said antibody is a human antibody.

Even if mAbs derived from animal models can be optimized (by undergoing chimerization and/or humanization) for the administration in human therapy or prophylaxis, a fully human mAb is certainly preferred to animal derived mAb giving the very low risk that administered human mAb could be recognized as non-self molecule leading to side effects compared to animal derived mAbs. Furthermore an antibody produced by a subject infected by a virus is elicited by the virus in its true and replicating form, while the immunization of an animal usually consists of the injection of a purified protein or of a non-replicating form of the virus. As a consequence, antibodies elicited in the natural host usually have a stronger activity and, being directed against conformational epitopes, are usually less subject to the emergence of viral escape mutants.

In a further aspect, the invention provides an HSV-1 and HSV-2 binding antibody or fragment thereof, wherein said antibody is a monoclonal antibody.

The clinical advantages of using a monoclonal antibody instead of a polyclonal serum are many and well know in the art. ("Monoclonal versus polyclonal antibodies: distinguishing characteristics, applications, and information resources." N. S. Lipman et al. ILAR J (2005) 46 (3): 258-268. and "Passive antibody therapy for infectious diseases." A. Casadevall et al. Nature Reviews Microbiology 2, 695-703 (September 2004)).

In a still further aspect, the HSV-1 and HSV-2 binding monoclonal antibodies or fragment thereof according to the present invention have IgG2 heavy chain constant regions.

In a preferred aspect, the HSV-1 and HSV-2 binding monoclonal antibodies or fragment thereof according to the present invention have IgG1 heavy chain constant regions.

In order to optimize expression rate both in prokaryotic and eukaryotic (whole IgG1) production systems the HSV-1 and HSV-2 binding monoclonal antibodies or fragment thereof according to the present invention were successfully converted into IgG1 antibodies. The variable regions of said antibodies were advantageously cloned into a modified vector containing constant region heavy chains (HCs).

The IgG1 converted HSV-1 and HSV-2 binding monoclonal antibodies or fragments thereof according to the present invention are capable of recognizing and neutralizing both HSV-1 and 2 isolates with high potency.

A still further embodiment of the present invention is a pharmaceutical composition comprising an HSV-1 and HSV-2 binding monoclonal antibody or fragment thereof, according to the present invention and a pharmaceutically acceptable carrier.

The antibodies according to the present invention can ameliorate symptoms of primary, non-primary and recurrent HSV infections.

The antibodies of this invention are suitable for therapy or prophylaxis of HSV-infections in a variety of patients and HSV-associated diseases.

Furthermore, the present antibodies are suitable for topical use, both for prophylaxis and therapy. They are especially suited in instances of low index of suspicion, where drug therapy may be contraindicated or undesirable, since they have lower mechanistic toxicity and are very unlikely to have relevant unexpected toxicity or side effects.

The pharmaceutical composition according to the present invention has the advantages of being a new therapeutic strategy based on passive immunotherapy which makes use of specific monoclonal antibodies with HSV-1 and HSV-2 neutralizing activity, and is useful in the treatment of HSV infections and related diseases.

In a further aspect the pharmaceutical composition according to present invention is for oral, topical, ophthalmic, intramuscular, intravenous infusion, subcutaneous, or inhalation administration routes.

In a further aspect the pharmaceutical composition according to present invention is used or administered in combination with at least one antiviral agent.

In a preferred aspect, the antiviral agent can be chosen from the group consisting of for example acyclovir, ibacitabine, pencyclovir, gancyclovir, famcyclovir, valacyclovir, foscarnet or cidofovir.

In a still further embodiment the present invention relates to an HSV-1 and HSV-2 binding antibody or fragment thereof as described above, for use in the treatment of HSV-1 and/or HSV-2 associated diseases.

In a still further embodiment the present invention relates to an HSV-1 and HSV-2 binding antibody or fragment thereof for use in the treatment of HSV-1 and/or HSV-2 associated diseases as described above, wherein said treatment is of patients which are resistant or intolerant to previous treatment with at least one antiviral agent or wherein the treatment with an antiviral agent should be avoided, or wherein said patients are immunodeficient or immunosuppressed.

In a preferred aspect said HSV-1 or HSV-2 associated disease treatment is a prophylactic or therapeutic.

In a still preferred aspect, said HSV-1 or HSV-2 associated diseases are acute or chronic.

In a further preferred aspect, the HSV-1 and/or HSV-2 associated infection is primary, non-primary or recurrent.

Advantageously the HSV-1 and HSV-2 binding antibodies according to the present invention are thus useful in a variety of clinical manifestations of HSV-1 or HSV-2 infection.

Advantageously the HSV-1 and HSV-2 binding antibody according to the present invention are useful to decrease viral shedding.

Advantageously the HSV-1 and/or HSV-2 binding antibodies according to the present invention are useful to prevent transmission.

In a further aspect, the invention provides the use of an HSV-1 and HSV-2 binding monoclonal antibody or fragment thereof according to the present invention, wherein said HSV-1 and/or HSV-2 associated diseases are chosen from the group consisting of oral herpes, herpes keratitis, herpes whitlow, herpes gladiatorum, eczema herpeticum, neonatal herpes, genital herpes, atypical genital herpes, herpetic cervicitis, herpetic proctitis, herpetic encephalitis, herpetic meningitis, herpetic meningoencephalitis, disseminated herpes simplex infection, alzheimer's disease and dementia.

As indicated in the introduction, the need and importance are increasingly felt for novel therapies for the treatment of HSV infection. The monoclonal antibodies according to the present invention have HSV neutralizing activity and are therefore useful in the treatment of HSV infection.

The present antibodies can be the basis for the treatment of HSV infection and can also significantly contribute to resolution of the infection by inhibiting the virus replication and potentially limiting tissue damages caused by virus reactivations. These activities are very useful in the case of HSV isolates resistant to current antiviral drugs.

Oral herpes also known as cold sores can be the result of an HSV-1 or an HSV-2 infection. Because of the association of HSV-2 with sexual transmission, infections in children are usually the result of HSV-1.

The main diagnosis is herpetic gingivo-stomatitis, where the typical clear lesions first develop followed by ulcers that have a white appearance. The infection, often initially on the lips, spreads to all parts of the mouth and pharynx. Reactivation from the trigeminal ganglia can result in what are known as cold sores. Herpes pharyngitis is often associated with other viral infections of the upper respiratory tract. The disease is more severe in immunosuppressed people such as AIDS patients.

Herpes keratitis is an infection of the eye and is primarily caused by HSV-1. It can be recurrent and may lead to blindness. It is a leading cause of corneal blindness in the United States.

Herpes whitlow affects people who come in manual contact with herpes-infected body secretions and can be caused by either type of HSV. HSV enters the body via small wounds on the hands or wrists. It can also be caused by transfer of HSV-2 from genitals to the hands.

Herpes gladiatorum is often found in wrestlers. It apparently spreads by direct contact from skin lesions on one wrestler to his/her opponent, and usually appears in the head and neck region (which are frequently sites of contact in wrestling holds). Oddly, the lesions are more often on the right side of the body (perhaps because most wrestlers are right handed). It is also seen in other contact sports such as rugby where it is known as scrum pox.

Eczema herpeticum is a pediatric condition found in children with active eczema or preexisting atopic dermatitis. HSV can spread over the skin at the site of eczema lesions. The virus can spread to other organs such as liver.

Neonatal herpes is a severe disease from HSV-2 and is often fatal, although such infection is rare. Infection is especially possible if the mother is shedding virus at the time of delivery. The virus can be contracted either in utero or during birth. Because the neonate has an underdeveloped immune system, the virus can spread rapidly to many peripheral organs (e.g. lungs and liver) and can infect the central nervous system.

Genital herpes and herpetic proctitis are usually the result of an HSV-2 infection with about 10% of cases being the result of HSV-1. Primary infection is often asymptomatic but many painful lesions can develop on the glans or shaft of the penis in men and on the vulva, vagina, cervix and perianal region of women where it may be accompanied by vaginal discharge. A variety of the infections also cause proctitis. Secondary episodes of genital herpes, a result of reactivation of virus in the sacral ganglion, are frequently less severe (and last a shorter time) than the first episode. Recurrent episodes seem usually to result from a primary HSV-2 infection. Whether there is an apparent active disease or not, an infected patient remains infectious without overt symptoms.

HSV encephalitis is the result of an HSV-1 infection and is the most common sporadic viral encephalitis. HSV encephalitis is febrile and may result in damage to one of the temporal lobes, clinically marked by blood in the spinal fluid and seizures. The disease can be fatal and in the US fewer than 1000 cases per year are described.

HSV meningitis is the result of an HSV-2 infection.

Disseminated herpes simplex infection is the spread of the infection throughout the body. This is a serious and life-threatening complication of HSV in patients with an impaired immune system.

HSV-1 has long been suspected to play a role in the pathogenesis of AD because of its neurotropism, high rate of infection in the general population, and life-long persistence in neuronal cells, particularly in the same brain regions that are usually altered in AD.

Recent data ("β-Amyloid peptides display protective activity against the human Alzheimer's disease-associated herpes simplex virus-1." Bourgade K et al. Biogerontology. 2014 Nov. 7) suggests that amyloid plaques, the hallmark of Alzheimer's disease (AD), contain fibrillar β-amyloid (Aβ) 1-40 and 1-42 peptides. HSV-1 has been implicated as a risk factor and found to co-localize within amyloid plaques. Aβ 1-40 and Aβ 1-42 display anti-bacterial, anti-yeast and anti-viral activities.

Other data ("Relationship between herpes simplex virus-1-specific antibody titers and cortical brain damage in Alzheimer's disease and amnestic mild cognitive impairment." Mancuso R, et al. Front Aging Neurosci. 2014 Oct. 15; 6:285) suggests that a strong HSV-1-specific humoral response could be protective toward AD-associated cortical damage.

Furthermore, other artificial forms of miniaturized antibodies may be prepared, such as minibodies and nanobodies. These alternative forms may be successfully prepared and used starting from the antibodies of the present invention.

Various embodiments and aspects of the present invention as delineated hereinabove, and as claimed in the Claims section below, find experimental support in the following Experimental section.

Experimental Section

Reference is now made to the following Experimental section, which together with the above description illustrates some embodiments of the invention.

In particular, as discussed in the following section, the work that conducted to the identification of the monoclonal antibodies which bind and neutralize HSV-1 and HSV-2 can be summarized as follows:

1. Analysis of the subjects' polyclonal sera;
2. Purification of the IgG2 fraction;
3. Evaluation of the quantity of IgG2 purified from the sera;
4. Evaluation of the IgG2 binding and neutralization activity towards HSV;
5. Subject selection;
6. IgG2 library construction from the selected subject;

7. Library validation and biopanning optimization;
8. Preliminary screening of the IgG2 antibody clones selected after the Fab production in Freezing and Thawing;
9. Fab IgG2 clone purification, sequencing and preliminary evaluation of neutralizing activity against HSV;
10. Conversion of the clones into Fab IgG1;
11. Purification and sequencing of the IgG1-transformed clones; exhaustive and quantitative evaluation of their neutralizing activity (the neutralizing activity was evaluated for all the clones, however an exhaustive and fine evaluation of the neutralizing activity was performed only for Fab-Ex2).

Subject Selection: Criteria and Results

IgG2 fractions were collected, detected and purified from peripheral blood samples deriving from a selected cohort of subjects.

The selection criteria were the following:
1) high content of IgG2, 2) capability to recognize HSV-1 and HSV-2 in ELISA assays, and 3) clinical history of HSV reactivation.

Figure 1A:
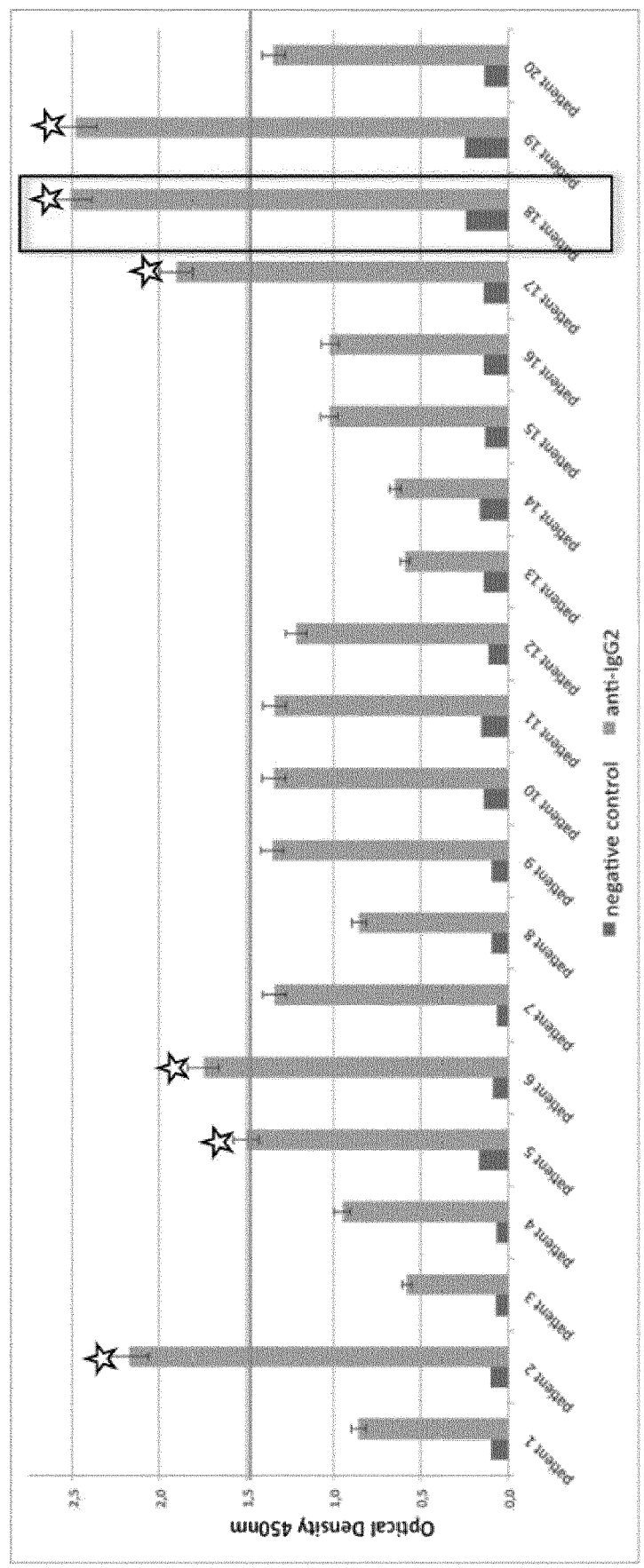
FIG. 1A shows the presence of IgG2 in human sera from twenty different subjects. The stars indicate the sera showing a high ELISA-O.D. (Optical Density) signal. The black box indicates the high ELISA-OD signal of the IgG2 fraction derived from subject no. 18.
Figure 1B:
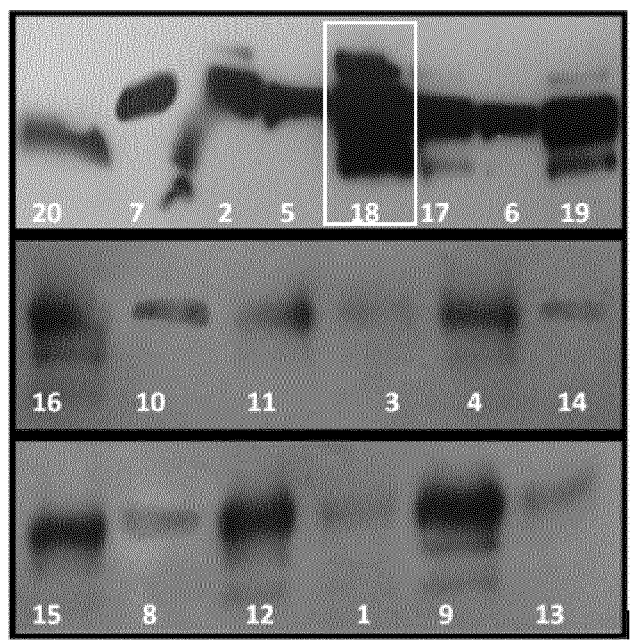
FIG. 1B illustrates the results of a Western Blot (WB) analysis detected with anti-human IgG2 antibody performed on human sera (1:10 dilution). Also in this assay, the serum from donor no. 18 (white box) showed a high IgG2 content. The WB analysis is consistent with the results of the ELISA assay (FIG. 1A).
Figure 2:
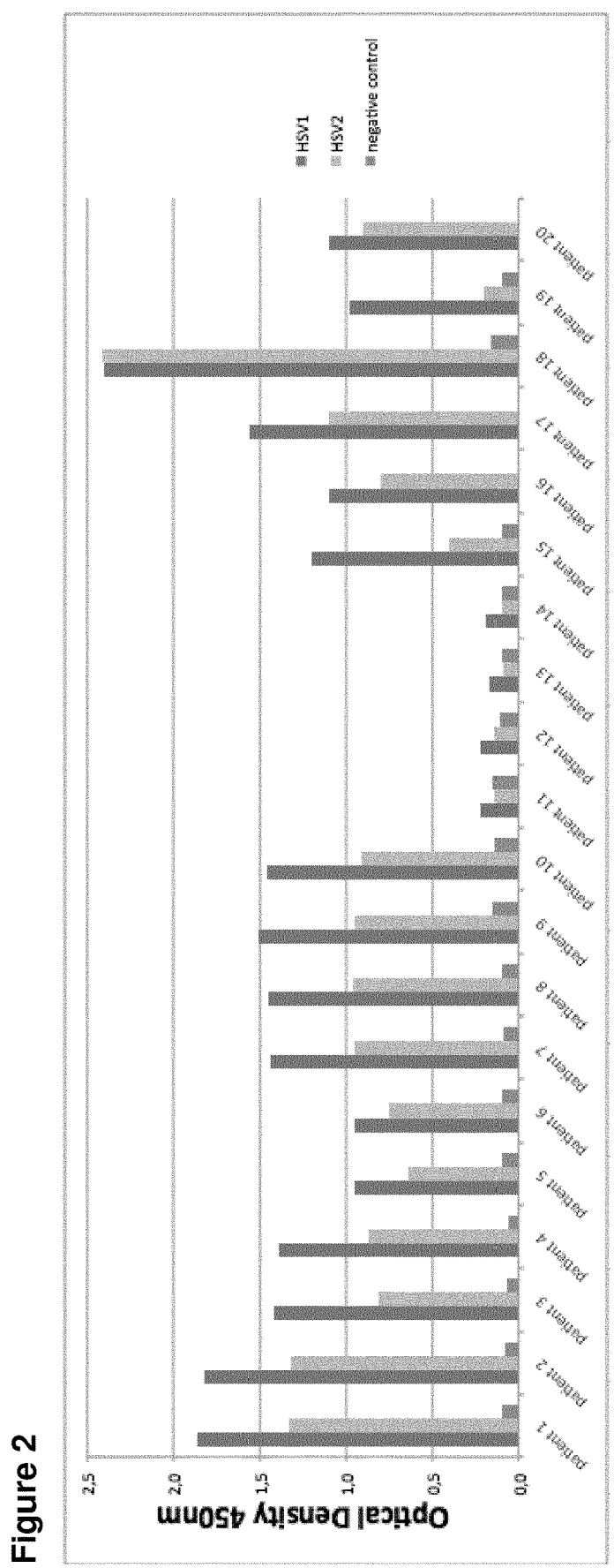
FIG. 2 is a graph illustrating the results of an ELISA assay showing the IgG2 reactivity against HSV-1 and HSV-2 inactivated viruses. The serum from subject no. 18 showed a high binding capability against HSV-1 and HSV-2.

The serum from subject no. 18 was the only sample able to meet all the aforementioned first-selection criteria (FIGS. 1A, 1B and 2). The subject no. 18 reported a previous history of frequent reactivation of labial HSV with a recent and spontaneous clinical improvement.

Purification and Characterization of the IgG2 Fraction from the Selected Subject.

Given the high amount of IgG2 purified from subject no. 18 serum and its capability to recognize both HSV-1 and 2 in ELISA assays, this subject was selected to investigate the ability of his purified IgG2 to neutralize HSV-1 and 2 infections. The IgG2 fraction from donor no. 18 was purified using the protocol described below in the Materials and Methods section (IgG2 Purification and quantitation protocol).

TABLE 1

Clinical features of subject no. 18
Subject no. 18

| | |
|---|---|
| Age (yrs) | 37 |
| Sex | Male |
| Height (m) | 1.90 |
| Weight (Kg) | 95.5 |
| Previous and concomitant conditions | No |
| HSV 1 | Yes—Clinical diagnosis |
| HSV 2 | No—Clinical diagnosis |
| Laboratory diagnosis of HSV | Not performed |
| Antiviral drug/s taken for HSV-1 | Acyclovir (by topical administration) |
| Description of clinical symptoms | Paraesthesia and pain before the onset of clinical manifestations followed by the typical labial symptoms (vesicular lesions followed by ulcers and crusts at the vermillion labial border). The clinical picture spontaneously improved over the last 6 months. |

Figure 7:
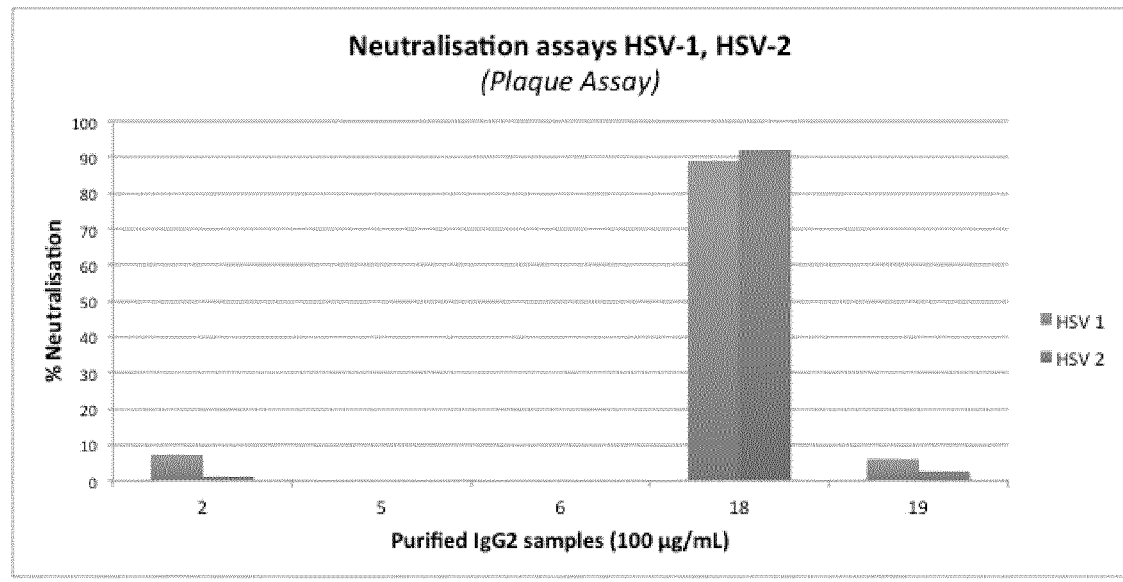
FIG. 7 is a histogram illustrating a quantitative assay performed using the plaque reduction technique. The anti-HSV-1 and anti-HSV-2 neutralizing activity of IgG2 purified from subject no. 18 (pIgG2-18) vs controls (IgG2 purified from other subjects) was assessed in this assay. The IgG2 fraction purified from subject no. 18 sera strongly neutralized both HSV-1 and HSV-2 tested isolates.
Figure 8:
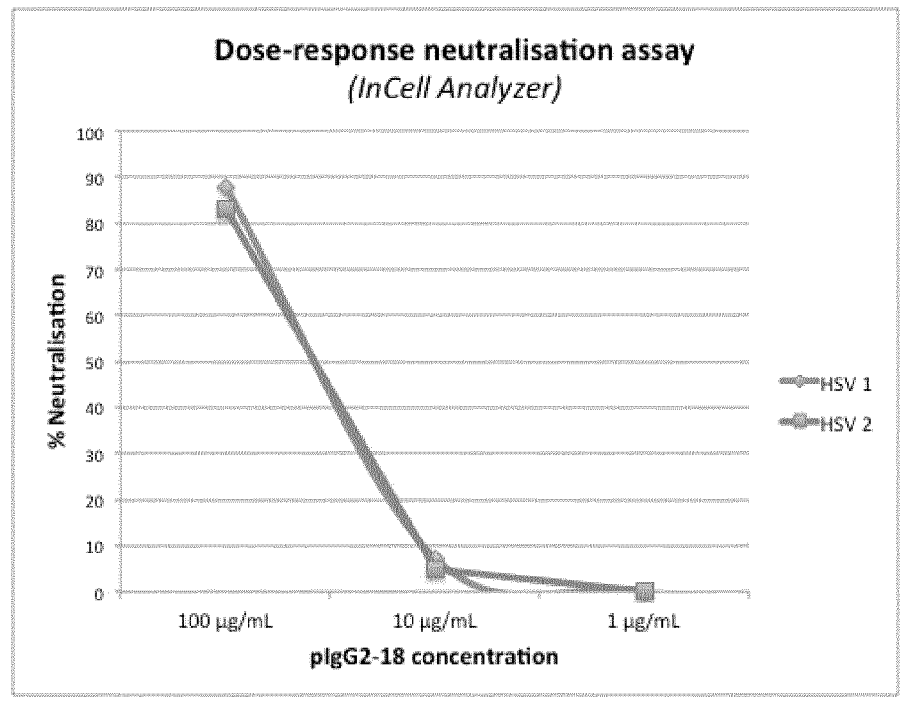
FIG. 8 is a graph illustrating the results of a dose-response neutralization assay. This assay is a quantitative assay performed using the IIF technique (the exact number of HSV infection foci was assessed using the InCell Analyzer automated system). The dose-response HSV-1 and HSV-2 neutralization assay was performed with pIgG2-18 (purified IgG2 from subject no. 18).

The IgG2 fraction derived from subject no. 18 (pIgG2-18) showed an extraordinary neutralizing activity against both HSV-1 and HSV-2. In particular, pIgG2-18 neutralizing activity against HSV-1 and HSV-2 tested viruses was assessed and confirmed using both qualitative assays (syncytia formation evaluation through bright field phase contrast optical microscope and Immunofluorescence assay, FIGS. 3-6) and quantitative assays (plaque reduction assays and quantitative neutralizing activity evaluation through Indirect Immuno-Fluorescence, IIF; FIGS. 7-8)

Figure 3:
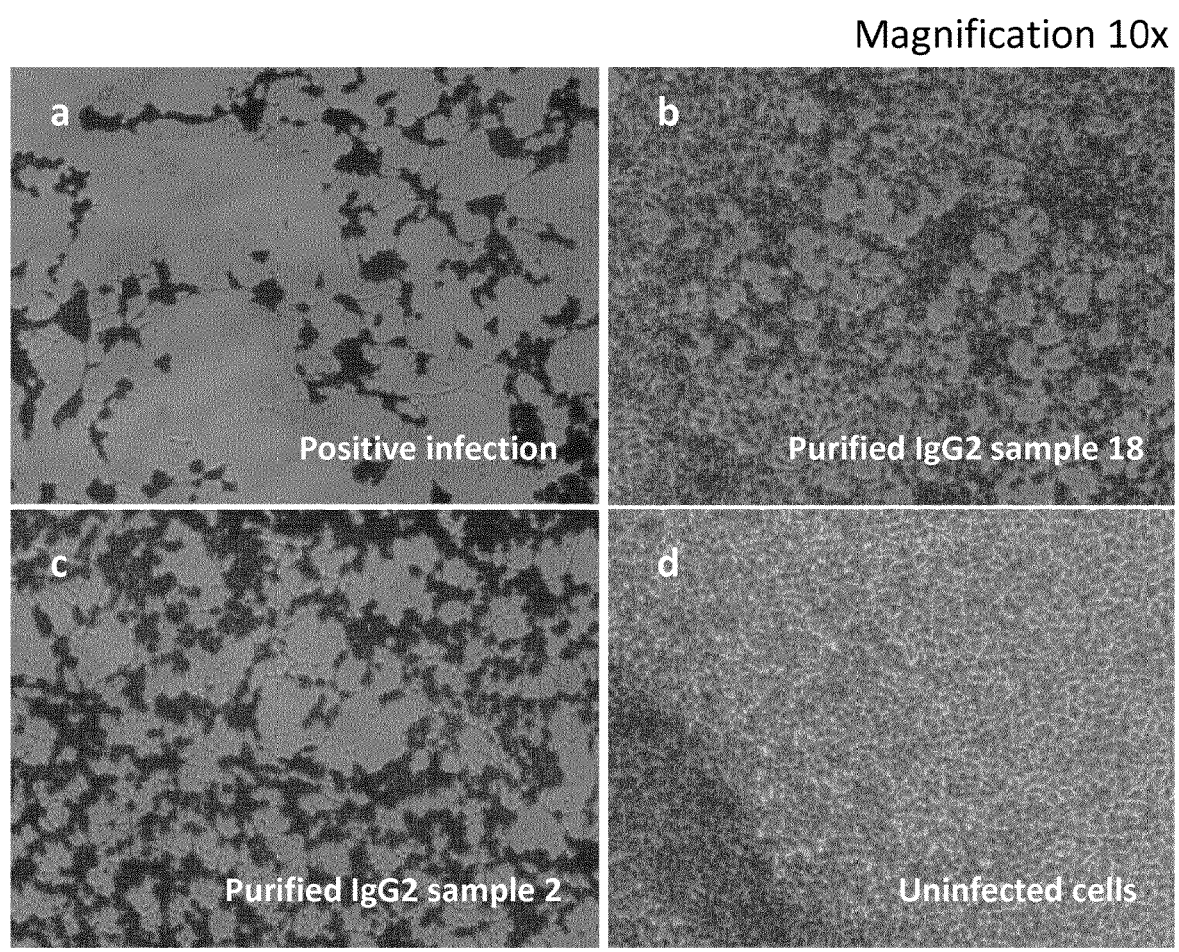
FIG. 3 is a 10 times (10×) and 40 times (40×) magnification of cells infected by HSV-1 showing syncytia formation. The evaluation was carried out through bright field phase contrast optical microscope in qualitative assays. The images show
Figure 3:
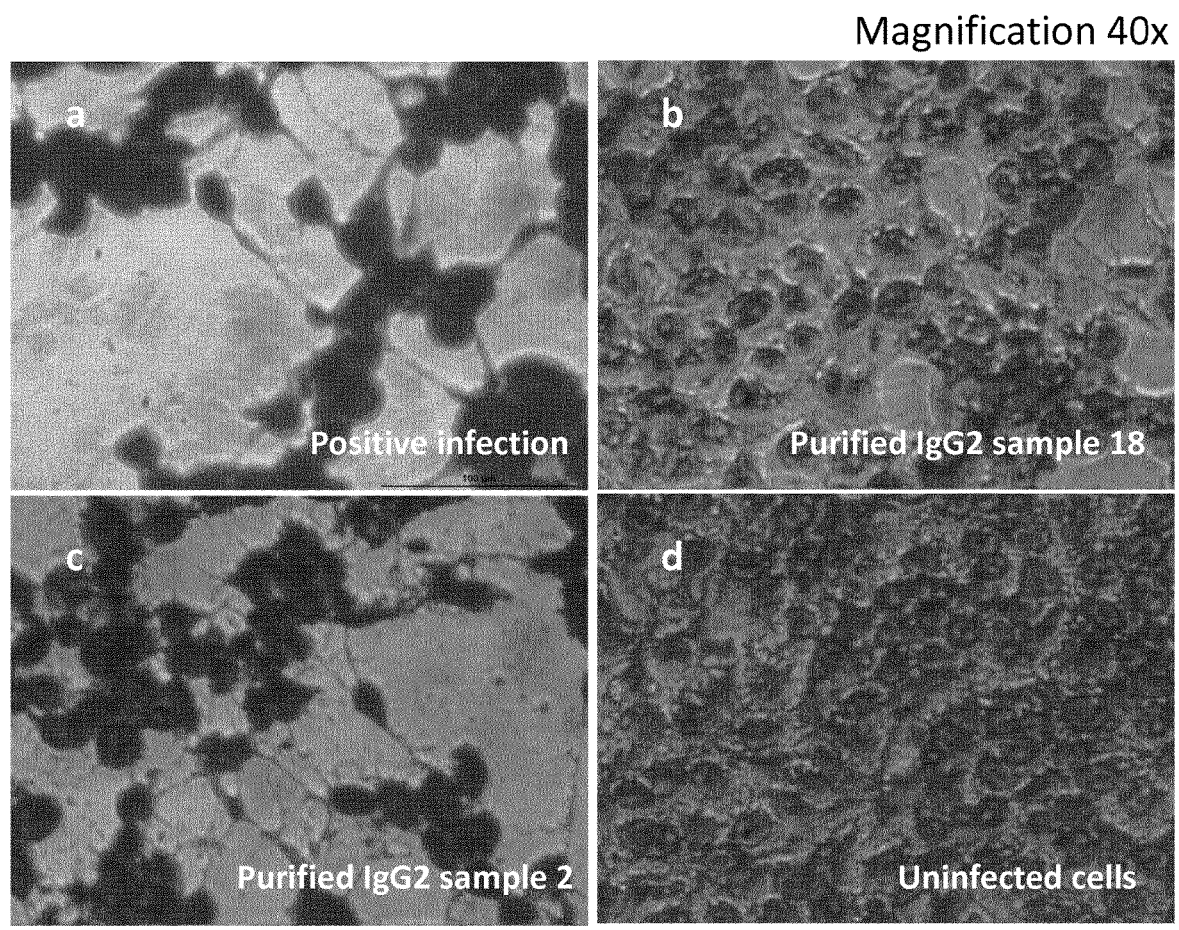

FIG. 3 shows the morphology of HSV-1 infected cells under the different experimental conditions.

In particular:
HSV-1 infected cells (positive infection control) show an evident cell monolayer disruption and the presence of syncytia caused by the virus compared to uninfected cells.
Cells infected with HSV-1 pre-incubated with purified IgG2 from the control subject show cell monolayer disruption and disseminated syncytia caused by the virus.
Cells infected with HSV-1 pre-incubated with purified IgG2 from subject no. 18 maintain the normal cellular morphology and show a significant reduction of syncytia formation, indicating a strong inhibition of HSV-1 infection.

Figure 4:
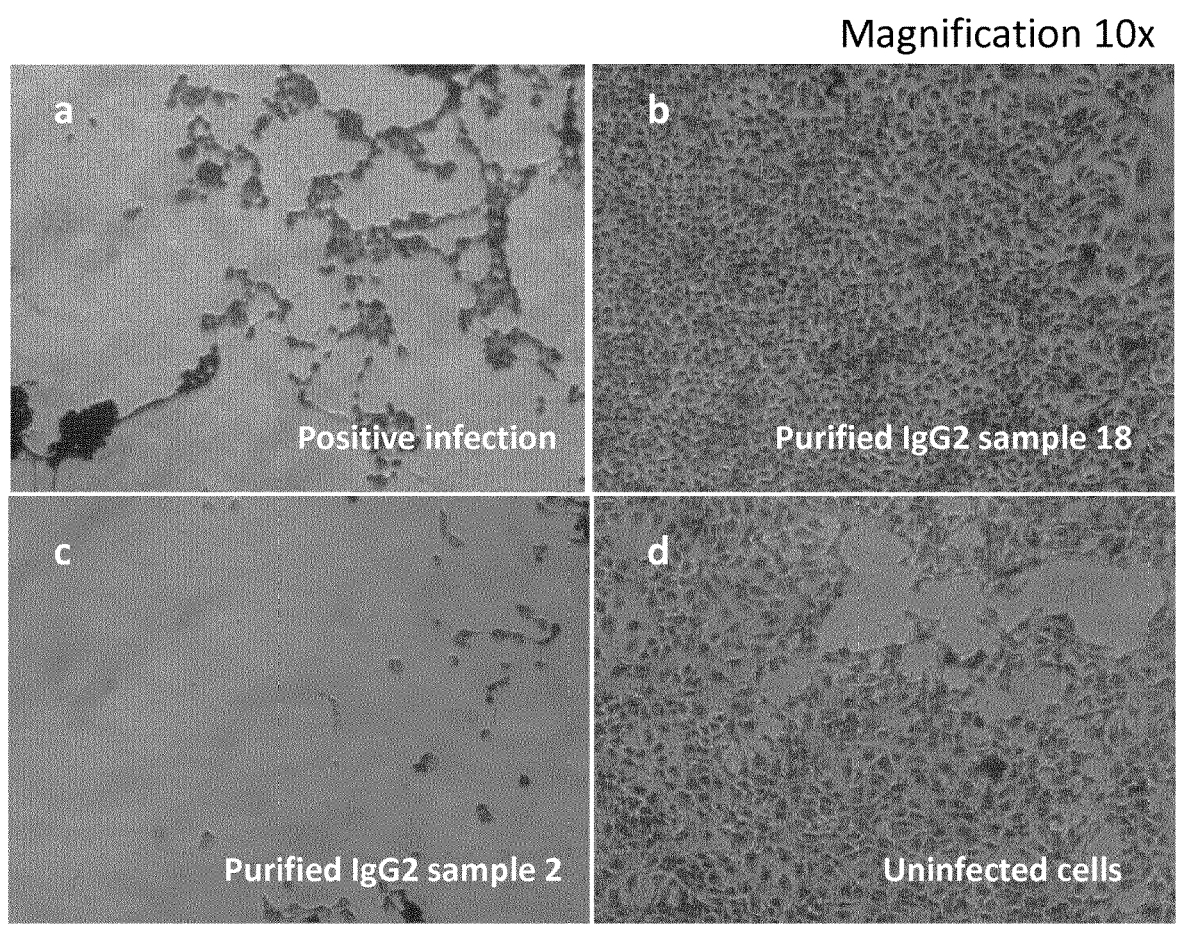
FIG. 4 is a 10 times (10×) and 40 times (40×) magnification of cells infected by HSV-2 showing syncytia formation. The evaluation was carried out through bright field phase contrast optical microscope in qualitative assays. The images show
Figure 4:
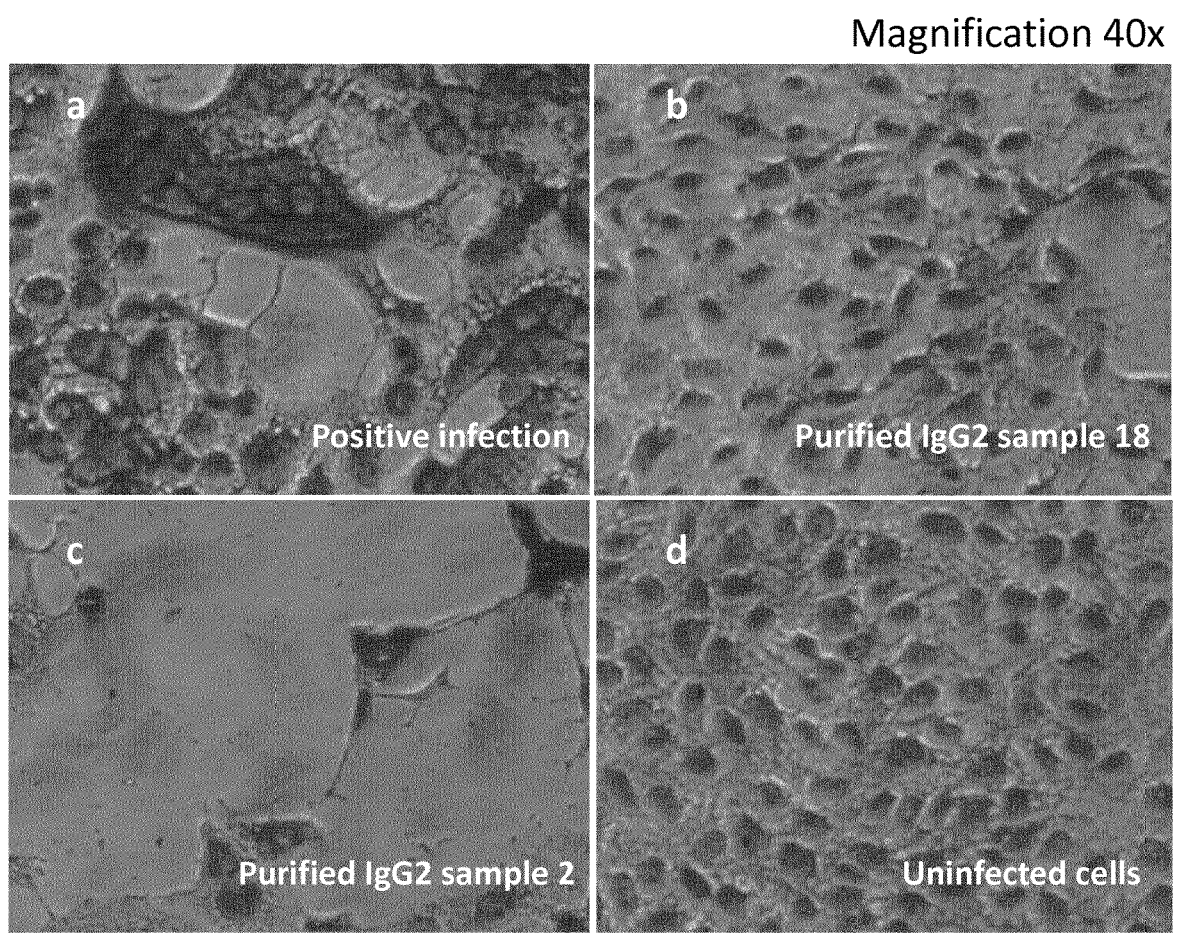

FIG. 4 shows the morphology of HSV-2 infected cells under the different experimental conditions.

In particular:
HSV-2 infected cells (positive infection control) show cell monolayer disruption and a strong presence of syncytia caused by the virus compared to uninfected cells.
Cells infected with HSV-2 pre-incubated with purified IgG2 from the control subject show an important cell monolayer disruption and the presence of syncytia caused by the virus.
Cells infected with HSV-2 pre-incubated with purified IgG2 from subject no. 18 present an almost complete cellular morphology conservation compared to control (uninfected cells). Moreover, there is a very significant reduction of syncytia formation, indicating a strong inhibition of HSV-2 infection.

Figure 5:
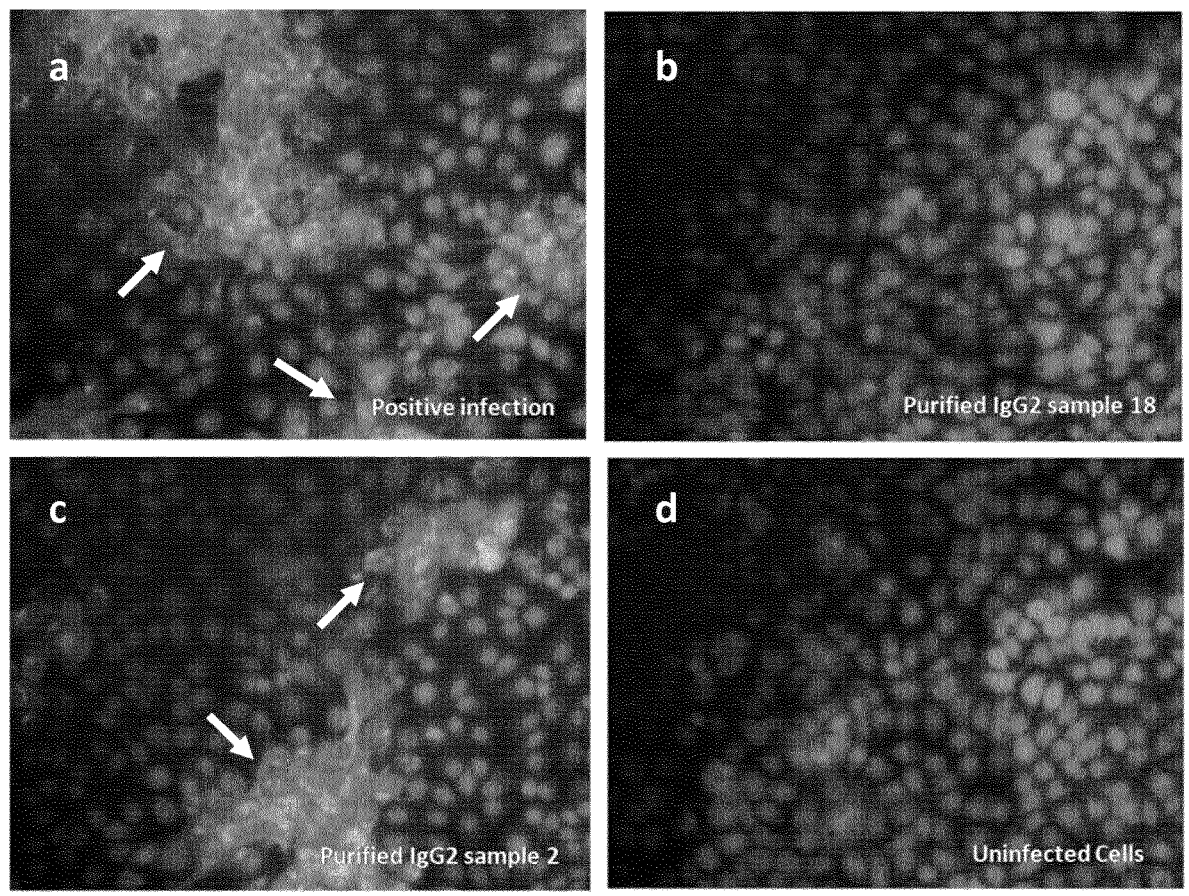
FIG. 5 shows a qualitative neutralizing activity evaluation by IIF (Indirect Immuno-Fluorescence) neutralization assay. The IgG2 neutralization capacity was tested against HSV-1. The images show
Figure 6:
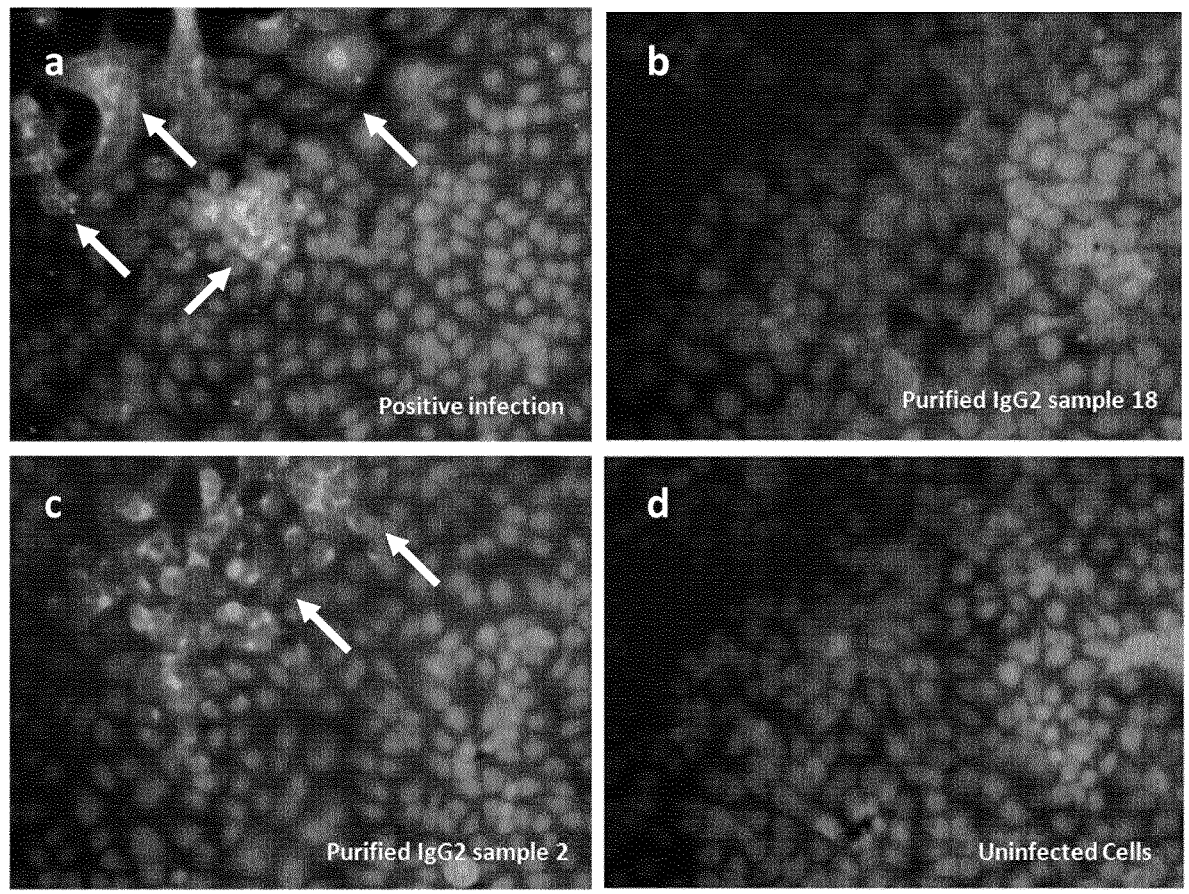
FIG. 6 shows a qualitative neutralizing activity evaluation assay by IIF. The IgG2 neutralization capacity was tested against HSV-2. The images show

FIGS. 5 and 6 show the different fluorescence patterns in the different experimental conditions.

In particular:
Positive controls show a diffused cytoplasmic fluorescence pattern typical of syncytia formed by HSV-1 and HSV-2.
Cells infected with HSV-1 or HSV-2 pre-incubated with purified IgG2 from control subject show a cytoplasmic fluorescent pattern similar to that observed in the positive infection control.
Cells infected with HSV-1 and HSV-2 pre-incubated with purified IgG2 from subject no. 18 show no immunofluorescent signal, indicating a strong inhibition of HSV-1 infection.

Selection and Generation of Anti-HSV Human Monoclonal Antibody Fab Fragments Directed Against HSV-1 and HSV-2 Antigens and Sequence Characterization a. Phagemidic IgG2 Fab Library Construction from Selected Subject The subject no. 18 was selected as a B lymphocytes source due to the high neutralizing activity against HSV-1 and HSV-2 tested isolates, and the inhibition of syncytia formation in HSV-1 and HSV-2-infected VERO-E6 cells, shown by the IgG2 fraction purified from his serum.

A new blood sample was collected from subject no. 18 in order to isolate his B lymphocytes. After extracting and retrotranscribing mRNA from these cells, IgG2 HCs (heavy chains) and LCs (light chains) were cloned into a phagemidic vector (L Solforosi, et al. "A phage display vector optimized for the generation of human antibody combinatorial libraries and the molecular cloning of monoclonal antibody fragments" (2012) New Microbiologica 35 (3), 289-294.)

A human combinatorial phage displayed antibody library was obtained as described below in the Materials and Methods section.

b. Library Biopanning Conditions: Development of Biopanning Conditions Allowing Molecular Selection and Cloning of Anti-HSV Human Monoclonal Antibodies Able to Recognize and Neutralize Both HSV-1 and HSV-2

Cloning of human Fab fragments able to cross-recognize and neutralize both HSV-1 and HSV-2 was obtained by an optimized biopanning procedure that allowed the molecular cloning of human Fabs featuring such biological properties. The screening of the selection rounds was performed by Freeze & Thawing procedure as described below in the Materials and Methods section.

From this selection strategy, five human monoclonal IgG2 Fab fragments were generated, namely:

Fab Ex2: corresponding to SEQ ID NO.1 and SEQ ID NO.2;

Fab Ex2B: corresponding to SEQ ID NO.4 and SEQ ID NO.5;

Fab Ex2C: corresponding to SEQ ID NO.7 and SEQ ID NO.8;

Fab Ex2H: corresponding to SEQ ID NO.10 and SEQ ID NO.11;

Fab Ex2I: corresponding to SEQ ID NO.4 and SEQ ID NO.13.

Figure 9:
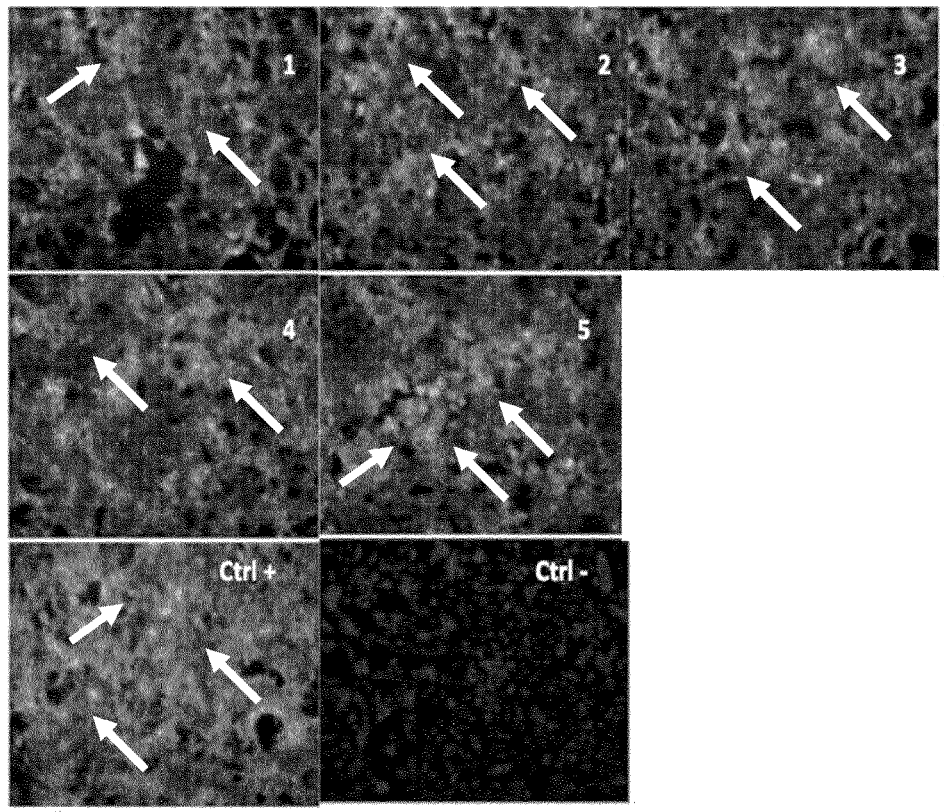
FIG. 9 shows the IIF analysis of the reactivity of Fab clones selected by bio-panning on HSV infected cells. All the Fabs selected from the constructed library specifically recognized only infected cells (FITC signal in green is indicated by arrows).
Figure 9:
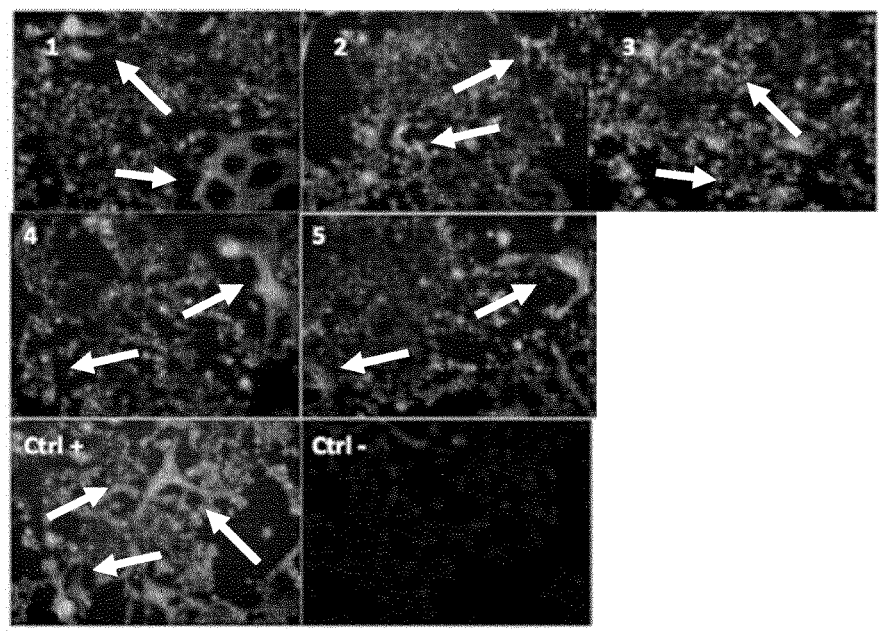

These five monoclonal IgG2 Fab fragments were selected and tested in IIF against HSV-1 and HSV-2 infected cells (FIG. 9). All the selected clones selectively recognized both HSV-1 and HSV-2 infected cells.

Production and Affinity Chromatography Purification of Selected IgG2 (G2) Fabs

The selected Fabs were produced in prokaryotic system and purified by affinity chromatography as described below in the Materials and Methods section.

Biological Activity Evaluation of Purified Selected Clones Directed Against HSV-1 and HSV-2

Figure 10:
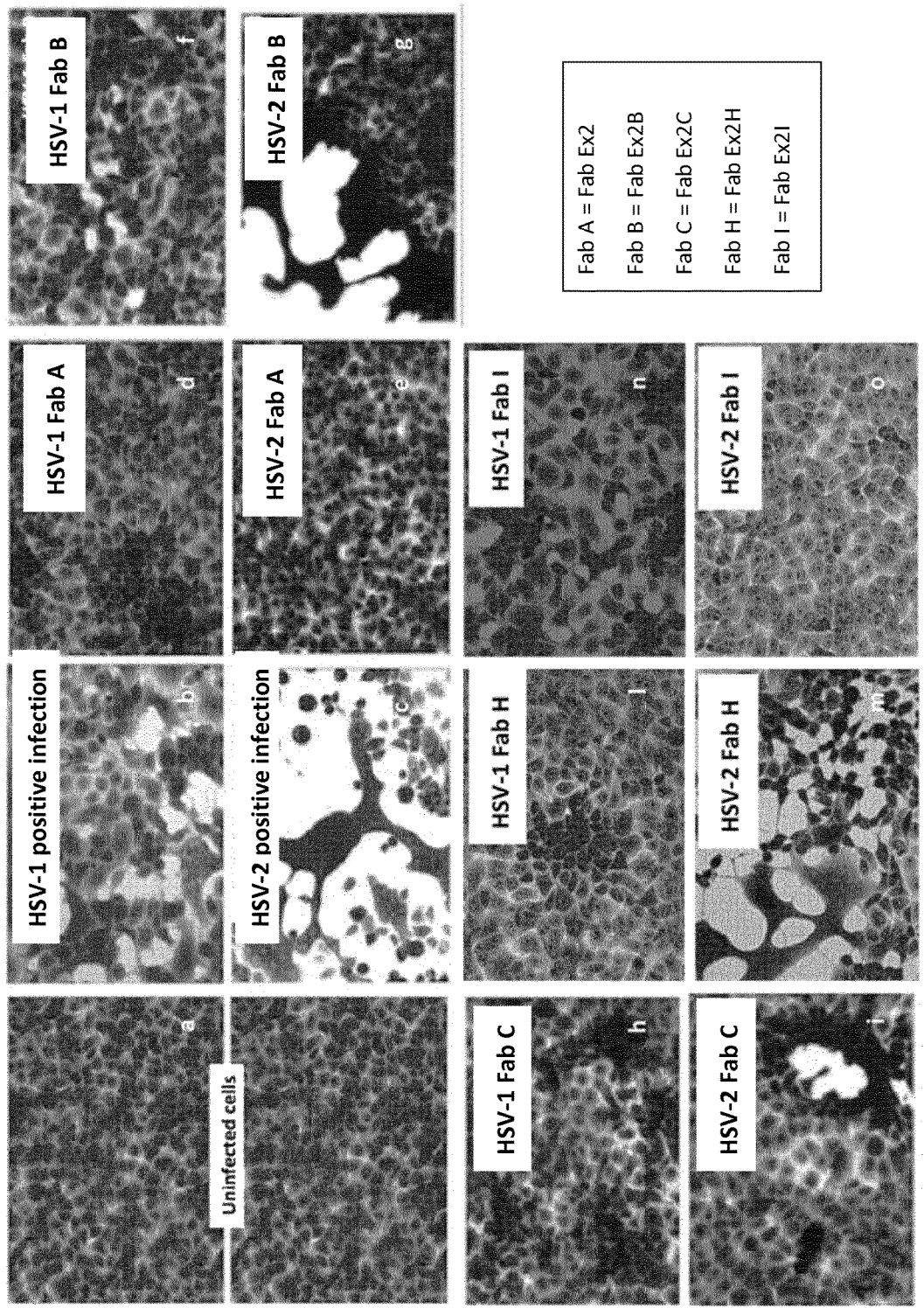
FIG. 10 shows a 40 times (40×) magnification of HSV infected cells showing syncytia formation. The evaluation was carried out through bright field phase contrast optical microscope in qualitative assays. The images show—FIG. 10a uninfected control cells.

Purified Fabs (Ex2(G2), Ex2B(G2), Ex2C(G2), Ex2H (G2) and Ex2I (G2)) were pre-incubated (10 µg/mL) with a standard amount of HSV-1 or HSV-2 isolates. Appropriate experimental controls were also included. The different "infection-mix" was used to infect Vero E6 cells (adsorption 2 hours before change of medium). After twenty hours, the cell monolayers were Fixed and Permeabilized with crystal violet containing solution allowing first a qualitative evaluation of Fabs biological activities against both HSV-1 and HSV-2 isolates (procedure described in the Materials and Methods section). The reduction of syncytia formation was assessed by bright field phase contrast optical microscopy (FIG. 10). As already stated, this assay allowed a first evaluation of Fab potencies. In particular from FIG. 10 it is possible to appreciate the high neutralization potency of Ex2(G2) against both HSV-1 and HSV-2. However, also the other four Fabs showed a good neutralization activity against both HSV-1 and 2 isolates. Only Ex2C(G2) and Ex2H(G2), showed a lower potency against HSV-2 when compared to Ex2(G2) and the other Fabs.

Conversion of the IgG2 Selected Fab Fragments Directed Against Both HSV-1 and HSV-2 (Five Fabs) into IgG1 Fab, Expression and Production In order to optimize expression rate both in prokaryotic and eukaryotic (whole IgG1) production systems, all the selected IgG2-Fabs directed against both HSV-1 and HSV-2 were successfully converted into IgG1 Fabs. The variable regions on heavy chains (HCs) belonging to selected Fabs and LCs were-successfully cloned into modified vector containing constant region (CH1) of IgG1 (procedures described in the Materials and Methods section). When not indicated, expressly or by (G2), the Fabs described in this patent are IgG2 Fabs converted to IgG1 as described.

All the procedures used to characterize the IgG2 selected Fabs were repeated to characterize the IgG1 form of selected Fabs allowing to compare the respective biological properties of IgG2 and IgG1 Fab formats.

From the biological activity assays, it was possible to demonstrate that IgG1 converted Fabs were still capable of recognizing and neutralizing both HSV-1 and 2 isolates with a high potency. Moreover, it was possible to show that the IgG1 format of Fab Ex2 neutralizes both HSV-1 and HSV-2 with an increased potency compared to its original clone format.

The biological assays performed are listed below:

Syncytia Formation Evaluation: Qualitative Assays Performed in Order to Evaluate Activity of Fab Clones of IgG1 Format Directed Against HSV-1 and HSV-2

The qualitative assays (described in the Materials and Methods section) were performed on IgG1 format of selected anti-HSV-1 and 2 Fabs (FIG. 11). These assays showed that also IgG1 formats of selected Fabs were able to neutralize both HSV-1 and HSV-2 (Table 2).

TABLE 2

Results of qualitative assays performed on IgG1 format of selected Fabs.

| Fab (IgG1) | HSV-1 | HSV-2 |
|---|---|---|
| Ex2 | ++++ | +++++ |
| Ex2B | ++ | ++ |
| Ex2C | ++ | +/− |
| Ex2H | ++ | + |
| Ex2I | + | +++ |

Quantitative Assays Performed with Anti-HSV-1 and 2 Neutralizing Fabs (IgG1 Format):

These assays were performed to quantify the potency of the selected anti-HSV Fab panel. All the Fab biological activities against HSV-1 and 2 were first assessed by IIF analysis.

The neutralizing activity of Fabs Ex2, Ex2B, Ex2C, Ex2H and Ex2I was evaluated using the InCellAnalyzer automated count system in order to calculate the $IC_{50}$s of all Fab and obtain a dose-response curve. Several dilutions of the different Fabs were used in order to obtain the dose-response curve. In all sets of neutralization experiments several Fab dilutions were performed since only using a biological compound limit dilution was possible to obtain the exact amount of Fab able to inhibit viral infection.

Moreover, the same "dose-response" curve allowed the calculation of Fab $IC_{50}$ which effectively depicts the in vitro Fab potency. The $IC_{50}$ is the Fab concentration able to reduce by 50% the cell damage due to the infection of cell monolayer with a standard amount of virus (HSV-1 and HSV-2).

In other words, a low $IC_{50}$ means that a very low amount of Fab is needed to inhibit the viral infection.

Fab Ex2 was tested in triplicate (error bars indicate mean deviation for the different triplicates) (FIG. 12).

FIG. 12 shows the dose-response curves (dilutions) of Fab Ex2 already tested in the qualitative assays previously described. From the same graphs, the $IC_{50}$ of the antibody was calculated using the GraphPad software (Prism).

The IC$_{50}$ of Fab Ex2 is summarized below:

TABLE 3

IC50 of Fab Ex2.

| Fab | HSV-1 (IC$_{50}$ µg/mL ± CI 95%) | HSV-2 (IC$_{50}$ µg/mL ± CI 95%) |
|---|---|---|
| Ex2 | 0.7 (0.44-1.21) | 0.2 (0.19-0.23) |

Exhaustive Study of IgG1 Fab Ex2 Neutralizing Activity

Fab Ex2 showed the most promising results against HSV-1 and HSV-2.

In order to further characterize and confirm its biological activity several neutralization experiments were performed following the procedures described below in the Materials and Methods section.

Qualitative Neutralizing Activity Evaluation Through Syncytia Formation Assay

This assay shows the effective potency of the Fab allowing to evaluate the presence/absence of cytopathic effects (complete disruption of cellular morphology) in the presence or absence of Fab Ex2.

In order to evaluate the potency of Fab Ex2, a qualitative assay using different dilutions was performed. Three different concentrations of Ex2 (10 µg/ml, 5 µg/ml and 2.5 µg/ml) were tested against HSV-1 and 2 through the syncytia formation assay.

As clearly depicted in FIG. 13, Fab Ex2 was able to strongly inhibit the cellular disruption and syncytia formation caused HSV-1 infection in a dose-dependent manner, and to completely inhibit HSV-2 infection at very low concentrations.

The cytopathic effect of HSV isolates on cells in the absence of Fab Ex2 is shown in FIG. 13.

When Fab Ex2 was added in different concentrations to the same infecting dose of HSV-1 or 2 prior to infection of the cell monolayer, the cellular morphology disruption was clearly inversely proportional to the Fab Ex2 concentration.

The extremely good results observed for Fab Ex2 with the inhibition of syncytia formation assays, are consistent with the quantitative evaluation of Fab A neutralization potency described below.

Quantitative Neutralizing Activity Evaluation Through Plaque Reduction Assay

Dose-response quantitative assay: the capability of Fab Ex2 to inhibit HSV infection was assessed by evaluating the presence of lysis plaques on cell monolayer due to HSV infection in the presence or in the absence of Fab Ex2. To confirm the IIF neutralization data, a plaque reduction assay was performed as quantitative evaluation. As widely described in the literature, the plaque assay is considered as the experiment of choice for the in vitro evaluation of neutralizing activity against HSV infection and is currently the gold standard for the evaluation of mAb IC$_{50}$.

As shown reported in FIG. 14, the dose-dependent quantitative evaluation of the biological activity of Fab Ex2 against HSV-1 and 2, not only endorsed the qualitative results previously described, but also showed that Fab Ex2 potency was unexpectedly high. In fact, as clearly shown in the graph, even at a very low concentration (1 µg/mL) Fab Ex2 inhibited HSV-1 plaque formation measured as PFU (plaque-forming unit). As shown in FIG. 14 (HSV-2 neutralization assay), an even greater Fab Ex2 neutralizing potency against the HSV-2 isolate was demonstrated. In addition, the HSV-1 neutralization assay showed the Fab Ex2 dose-response effect, as already evidenced by the qualitative dose-dependent assays.

Due to the very high potency of Fab Ex2, a dose-response effect could not be measured by the neutralization assay carried out with the HSV-2 isolate.

Sequence Study and Gene Usage Analysis of Selected Fab Clones

The sequences of both HCs and LCs from selected Fabs revealed that all the chains are correctly on frame and without any stop codon that can affect their expression level.

Gene usage analysis performed using a reference database of immunoglobulin sequences (IMGT—imgt.org), allowed a preliminary examination of the mutational rate of the selected clones compared to their germ-line sequences (Table 4).

All the selected Fab clones are mutated in their CDRs (Complementarity Determining Regions) when compared to the respective germ-line sequences. This means that the different clones display unique somatic mutations matured after the contact with the antigens. This usually allows more specific antigen recognition.

TABLE 4

| Fab Sequence ID | Functionality | V-GENE and allele | V-REGION identity % |
|---|---|---|---|
| HCs | | | |
| Ex2 | productive | Homsap IGHV3-30-3*01 F | 94.1 |
| Ex2B | productive | Homsap IGHV1-46*01 F, or Homsap IGHV1-46*03 F | 91.0 |
| Ex2C | productive | Homsap IGHV3-23*01 F, or Homsap IGHV3-23*04 F or Homsap IGHV3-23D*01 F | 89.9 |
| Ex2H | Productive | Homsap IGHV1-2*02 F | 89.6 |
| Ex2I | Productive | Homsap IGHV1-46*01 F, or Homsap IGHV1-46*03 F | 91.0 |
| LCs | | | |
| Ex2 | Productive | Homsap IGKV3D-7*01 F | 80.5 |
| Ex2B | Productive | Homsap IGKV3-20*01 F | 91.5 |
| Ex2C | Productive | Homsap IGKV3D-20*01 F | 93.6 |
| Ex2H | Productive | Homsap IGKV3-15*01 F | 93.2 |
| Ex2I | Productive | Homsap IGKV3D-20*01 F | 93.6 |

Conversion of the IgG1 Fab Ex2 into a Full IgG1, Identified as IgGA

Single Chain Antibody a (ScFvA) Production and Evaluation

ScFv gene of IgGA was successfully constructed and cloned into expression vector. ScFv format small scale production of IgGA was performed. The binding activity of ScFv A was evaluated by IIF assays on HSV infected cells. The ScFv A was able to recognize HSV infected cells. However, ScFv A showed high IIF background signal and low binding.

Fab Ex2: corresponds to SEQ ID NO.1 and SEQ ID NO.2

In Vitro Evaluation of the Biological Activity of IgGA

Neutralising Activity Against Clinical Isolates

The neutralising activity of FabA or IgGA was evaluated by pre-incubating (1 h at 37° C.) the IgGA with the virus and adding the IgGA/virus—mixture to cell monolayer.

Results

IgG A potently neutralises all the tested HSV-1 and 2 tested isolates. Importantly, the HSV isolates used to perform the neutralisation assays were endowed with different susceptibility to Acyclovir (ACV) anti-HSV drug. The capability of IgGA to neutralise the aforementioned HSV isolates indicates that the IgGA extraordinary biological activity is totally independent from the susceptibility to ACV showed by the different HSV tested isolates, suggesting a possible use of IgGA for the treatment of HSV infections caused by ACV resistant isolates (FIG. 15A).

Evaluation of Post Adsorption Inhibition of Infection

Post-adsorption assays have been developed in order to speculate on possible administration of IgG A for the treatment of HSV infection, after the beginning of virus active replication within the host.

The first step of experimental approaches, involving post-HSV adsorption evaluation of FabA or IgGA, is the infection of VERO E6 cells with a standard amount of HSV not previously treated with the FabA or IgGA.

FabA or IgGA is added to the infected cells only after 30 minutes from virus infection. The infection is then carried out for 48 h in order to appreciate the HSV lysis plaques on VERO E6 cells. The experimental results have been evaluated by counting the plaques for infected cells receiving (post-HSV infection) FabA or IgGA compared to virus experimental positive control.

Fabs tested in post-adsorption assays have been used at a concentration of 50 and 200 ug/mL against HSV-1 and HSV-2 tested isolates respectively*.

* mAb concentrations inferred from scientific literature

IgGs tested in post-adsorption assays have been used at a concentration of 25 and 100 ug/mL against HSV-1 and HSV-2 tested isolates respectively*.

Results

As demonstrated by post-adsorption assays, IgGA strongly inhibits both for HSV-1 and HSV-2 new infection events and also inhibits the number of infectious foci resulting in plaques compared to virus controls. IgGA inhibition strength was higher than those observed with FabA (FIG. 15B).

Cell-to-Cell Infection Mechanism Inhibition

Among the HSV infection strategies, an important one is the so called "cell-to-cell" infection strategy.

Post post-adsorption assays have been performed in order to evaluate the contribution of IgGA in inhibiting "cell-to-cell" infection by measuring the plaque areas resulting from infected cells treated or untreated with FabA or IgGA.

Fabs tested in post-adsorption cell-to-cell infection inhibition assays have also been preliminary used at a concentration of 50 and 200 ug/mL against HSV-1 and HSV-2 tested isolates respectively*.

* mAb concentrations inferred from scientific literature

IgGs tested in post-adsorption "cell-to-cell" infection inhibition assays have also been preliminary used at a concentration of 25 and 100 ug/mL against HSV-1 and HSV-2 tested isolates respectively*.

Results

As demonstrated by post-adsorption assays, Fab A inhibits both for HSV-1 and HSV-2 the plaque areas. IgGA inhibition of plaque areas is even higher than Fab A inhibition activity. These data clearly demonstrated how IgGA post-infection administration can potently inhibit also "cell-to-cell" HSV infection (FIG. 15B).

Evaluation of the Emergence of Escape Mutants Under Selective Pressure of mAbA

In order to evaluate the presence of escape virus mutants generated under selective pressure of IgGA, HSV-1 infected VERO-E6 cells have been treated with increasing concentrations of Fab A. More in details, VERO cells have been cultured in T25 flasks in the experimental conditions extensively described in the previous reports ("virus propagation techniques"). Cell monolayers have been then infected by HSV-1 HF strain using 50 pfu/mL of cell free virus. After virus complete adsorption, the infected cells have been treated for three days with 0.2 ug/mL and 1 ug/mL of IgGA. Experimental controls, unrelated IgG (at concentration of 0.2 ug/mL and 1 ug/mL) and virus "alone" have been also included in the experiments. After three days the infected cell media have been collected and centrifuged in order to use medium centrifuged supernatants for new cell infection rounds. These new infection rounds have been carried out in the presence of 0.2 ug/mL and 1 ug/mL of IgGA and experimental controls. Five sequential identical infection rounds have been performed in the presence of the two concentrations of IgGA and control IgG above described. The cell supernatants of the last infection round have been then centrifuged and used to perform five new round of infection in the presence of increased concentrations of IgGA (5 ug/mL and 10 ug/mL). In order to test the capability of virus cultured in the constant presence of IgGA to escape from IgGA inhibitory activity the cell free supernatants belonging to the final infections in the presence of IgGA have been incubated 1 h at 37° C. in the presence of high IgGA concentration. After pre-incubation the neutralization mix has been used to infect new VERO-E6 cells.

Results

The IgGA pre-incubated with HSV has been still able to neutralize the virus isolate indicating that no "escape mutants" have been generated under the IgGA selective pressure at 5 and 10 ug/mL.

This indicates that: HF HSV-1 isolates tested in these experiments very hardly undergo amino acid mutations in the region recognized by our antibody allowing its escape from the antiviral activity of IgG A (in the presence of the two concentration of IgGA used to perform the assays).

Conclusions

No "escape mutants" were generated under the IgGA selective pressure. Possible explanations of this result can be summarized as follows: HF HSV-1 isolates tested in these experiments do not easily undergo amino acid mutations allowing its escape from the antiviral activity of IgGA (in the presence of the two concentrations of IgGA used to perform the assays).

In Vivo Evaluation of Antiviral Activity of IgGA:

Overall, the biological effects of IgGA in the different cohorts of mice HSV vaginally challenged were assessed by evaluating (i) the survival rates and (ii) clinical scores. The clinical scores used to define the clinical status of the different cohorts of mice are: 0=no sign, 1-1.5=slight genital erythema ad edema, 2-2.5: moderate genital inflammation, non purulent genital lesions, 3-3.5=purulent genital lesions and/or hind-limb paralysis, 4=death.

HSV Vaginal Challenge: Systemic IgGA 24 h Before Virus Challenge (Prophylaxis)

In prophylaxis experiments, systemic IgGA has been systemically administrated via lateral tail vein injection.

The IgGA has been i.v. administered at two different concentrations for different cohorts of mice receiving 5 and 15 mg/kg of IgG A respectively, as a single dose 24 h before a vaginal challenge with 107 TCID50 of MS-HSV-2 virus approximatively corresponding to 1 Lethal Dose 50—$LD_{50}$—of virus ($LD_{50}$ is the virus dose able to kill 50% of mice infected). Experimental controls consisting in mice cohort receiving only the virus challenge and a cohort receiving unrelated human IgG negative control (15 mg/Kg) have been included as well. The experiments have been carried out for 8 days post HSV-2 challenge in order to avoid unnecessary and illegal mice suffering.

Results

Figure 16C:
Figure 16C:
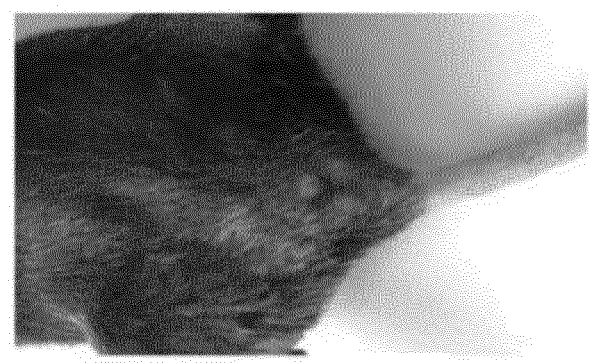
Figure 16C:
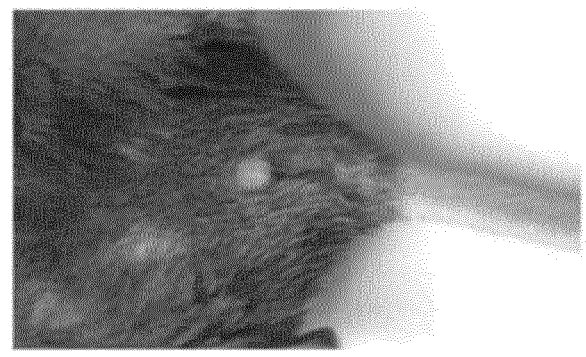

Both doses of IgGA showed protection of C57BL/6 mice against HSV-2 infection (FIG. 16A). Both antibody concentrations of 5 mg/kg and 15 mg/kg did significantly inhibit both mortality and clinical signs of HSV-2 infection (FIGS. 16B and 16C).

All the mice treated with IgGA at 5 mg/kg and 15 mg/kg survived (100% survival rate). On the contrary, mortality rates detected in mice cohorts receiving both unrelated human IgG at 15 mg/Kg and those receiving only the virus challenge have been completely coherent with HSV-2 LDs challenges.

HSV Vaginal Challenge: Systemic IgGA 30 Min and 24 h Post-Virus Challenge (Therapy)

In order to further study the protective activity of the human antibody IgGA, HSV-2-infected C57BL/6 mice received therapeutic systemic IgG A at 30 minutes and 24 h post-HSV-2 challenge (IgG A administrated via lateral tail vein injection). The IgGA has been i.v. administered at two different concentrations for two different cohorts of mice receiving 5 and 15 mg/kg of IgGA respectively 30 minutes and 24 h after the vaginal challenge with $10^7$ TCID$_{50}$ of MS-HSV-2 virus approximatively corresponding to 1 LD$_{50}$. Experimental controls consisting in mice cohort receiving only the virus challenge and a cohort receiving unrelated human IgG negative control (15 mg/Kg) and mice receiving ACV standard therapy (intraperitoneal injection of 50 mg/Kg 2× die) have been included as well. In these cohorts the experiments have been carried out for 12 days post HSV-2 challenge in order to avoid unnecessary and illegal mice suffering.

Results

Both doses of IgGA showed protection of C57BL/6 mice against HSV-2 infection (FIG. 17A). Both antibody concentrations of 5 mg/kg and 15 mg/kg did significantly inhibit both mortality and clinical signs of HSV-2 infection (FIGS. 17B and 17C). Also in this case all mice treated with IgGA at 5 mg/kg and 15 mg/kg survived (100% survival rate). On the contrary mortality rates detected in mice cohorts receiving both unrelated human IgG at 15 mg/Kg and those receiving only the virus challenge have been completely coherent with HSV-2 LDs challenges.

HSV Vaginal Challenge: Systemic IgGA 30 Min Post-Virus Challenge (Therapy)

To study the protective activity of the human antibody IgGA, HSV-2-infected C57BL/6 mice received therapeutic systemic IgGA at 30 minutes post-HSV-2 challenge (IgGA administred via lateral tail vein injection).

The IgGA has been i.v. administered at two different concentrations for different cohorts of mice receiving 5 and 15 mg/kg of IgGA respectively, as a single boost 30 minutes after the vaginal challenge with $10^7$ TCID50 of MS-HSV-2 virus approximatively corresponding to 1 LD$_{50}$. Experimental controls consisting in mice cohort receiving only the virus challenge and a cohort receiving unrelated human IgG negative control (15 mg/Kg). The experiments have been carried out for 8 days post HSV-2 challenge in order to avoid unnecessary and illegal mice suffering.

Results

Both doses of IgGA showed protection of C57BL/6 mice against HSV-2 infection (FIG. 18A). Both antibody concentrations of 5 mg/kg and 15 mg/kg did significantly inhibit both mortality and clinical signs of HSV-2 infection (FIGS. 18B and 18C). Also in this case all mice treated with IgGA at 5 mg/kg and 15 mg/kg survived (100% survival rate). On the contrary mortality rates detected in mice cohorts receiving both unrelated human IgG at 15 mg/Kg and those receiving only the virus challenge have been completely coherent with HSV-2 LDs challenges HSV Ocular Challenge: Evaluation of Biological Activity of IgGA Administered Systemically (Intravenous (i.v.) Injection)

Systemic protection conferred by intra-venous administration of IgGA after lethal-HSV-2 or HSV-1 ocular challenge was evaluated, by in vivo testing two HSV types.

HSV-2 or HSV-1 infected C57BL/6 mice (ocular infection after corneal scarification) received single boost therapeutic systemic IgGA at 30 minutes post-HSV challenge (IgGA administrated via lateral tail vein injection).

The IgGA was administered i.v. at 15 mg/kg 30 minutes after the ocular virus challenge with $10^7$ TCID$_{50}$ of MS-HSV-2 (approximatively corresponding to 1 LD$_{50}$) or $10^8$ TCID$_{50}$ of LV-HSV-1 (approximatively corresponding to 1 LD$_{50}$). Experimental controls consisting in mice cohort receiving only the virus challenge and a cohort receiving unrelated human IgG negative control (15 mg/Kg) have been included as well. The biological effects of IgGA in the different cohorts of mice were assessed by evaluating (i) the survival rates and (ii) clinical scores explained in the below "Clinical scores Table" (Berdugo M. Antimicrob Agents Chemother. 2012 March). All the mice were observed daily for the clinical signs of HSV infection.

| Clinical symptoms | Characteristic(s) with clinical disease score of: | | | | |
|---|---|---|---|---|---|
| | 0 | 1+ | 2+ | 3+ | 4+ |
| Blepharitis | None | Noticeably puffy eyelids with moderate crusting | Puffy eyelids with moderate crusting | Eye 50% swollen shue with moderate crusting | Eye completely swollen shut with severe crusting |
| Corneal neovascularization | None | <25% of the cornea involved | 25-50% involved | >50% of the cornea involved | |
| Stromal keratitis | None | Cloudiness, some iris detail visible | Iris detail obscured | Cornea totally opaque | Cornea perforated |
| Epithelial keratitis | None, corneal scratch (CS) only | <25% of epithelium outside of CS stained | 50% of epithelium outside of CS stained | 50-75% of epithelium outside of CS stained | 50-100% of epithelium outside of CS stained |

CS: corneal scarification

In these cohorts the experiments have been carried out for 8 days post HSV challenge in order to avoid unnecessary and illegal mice suffering.

Results

Systemic administration of IgGA efficiently protects C57BL/6 mice against HSV-2 and HSV-1 lethal ocular infections.

In particular, FIG. 19A shows how IgGA single-boost systemic administration fully protects (100% survival rate) mice previously infected via corneal scarification with HSV-2 virus.

Moreover, FIGS. 19B and 19C clearly depict how the systemic administration of IgGA can significantly reduce severe clinical signs deriving from HSV-1 and HSV-2 ocular infection.

Conclusions

The capability of IgGA to protect from lethal virus ocular challenge was evaluated through the administration of IgGA via systemic route. The systemic protection of IgGA from ocular HSV infection was evaluated both for HSV-1 and HSV-2. In this set of experiments IgGA fully protected mice infected with type 1 or type 2 virus from death (100% protection). This indicates the almost complete inhibition of disseminated virus replication performed by systemic mAb A. Moreover as suggested by the observation of neurological clinical signs shown by infected mice receiving unrelated control mAb or only virus challenge, the mice cohorts receiving systemic IgGA completely abrogated the onset of neurological signs. Importantly, IgGA also potently inhibits the clinical signs of infection both for HSV-1 and 2 (clinical scoring).

Materials and Methods Section

Eukaryotic Cells and Viruses

VERO-E6 cell line were-used to perform all the experimental procedures on eukaryotic cells HSV-1 isolate cultured on VERO-E6 cells: HF strain (VR-260 ATCC)

HSV-2 isolate cultured on VERO-E6 cells: MS strain (VR-540 ATCC)

ELISA for IgG2 Fraction Detection Protocol:
 Microtiter 96-wells flat bottom ELISA plates (COSTAR) were coated (overnight at 4° C.) with the collected sera PBS diluted including a negative control.
 Nonspecific sites were blocked by incubating the plate (37° C. for an hour) with 1% PBS/BSA solution.
 After washing (PBS solution containing 0.2% (v/v) Tween20 (Sigma-Aldrich)), the commercially available mouse anti-Human IgG2 specific monoclonal antibody was added following the manufacturer instructions protocol (1 hour at 37° C.)
 Washing with PBS solution containing 0.2% (v/v) Tween20
 Peroxidase-conjugated anti-mouse IgG (Sigma-Aldrich) was added (45' at 37° C.)
 After washing with PBS solution containing 0.2% (v/v) Tween20, TMB substrate kit (Thermo Scientific) was added and the plate incubated at 37° C. for 5'
 1N sulphuric acid was then added to stop the reaction.
 The signal was detected at 450 nm wavelength.

Western Blot for IgG2 Fraction Detection Protocol:
 The collected sera were analysed on 8% Tris-glycine gels (Bio-Rad) at two different dilutions (1:10 and 1:100 respectively).
 Proteins were transferred to PVDF membrane (PerkinElmer) for 15 hours at 30V at 4° C.
 Nonspecific sites were blocked by incubating the membrane over night at 4° C. in a PBS solution containing 0.2% (v/v) Tween20 (Sigma-Aldrich) and 5% (w/v) non fat dried milk.
 The commercially available mouse mAb specific for human IgG2 was used as a primary reagent for 1 hour incubation at room temperature.
 Washing with a PBS solution containing 0.1% (v/v) Tween20.
 The blot was probed with peroxidase-conjugated anti-mouse IgG (Sigma-Aldrich) (45' at room temperature).
 The peroxidase-conjugated Ab was detected using the Super Signal West Pico Chemiluminescent Substrate (Thermo Scientific).

ELISA Assay Against HSV-1 and HSV-2 Coated Inactivated Viruses
 Microtiter 96-wells flat bottom ELISA plates (COSTAR) were coated (overnight at 4° C.) with heat-inactivated HSV-1 and HSV-2 ECB diluted (1:10) including a negative control.
 Nonspecific sites were blocked by incubating the plate (37° C. for an hour) with 1% PBS/BSA solution.
 After washing (PBS solution containing 0.2% (v/v) Tween20 (Sigma-Aldrich)), the collected sera PBS/BSA diluted (1:200) was added (1 hour at 37° C.)
 Washing with PBS solution containing 0.2% (v/v) Tween20
 Peroxidase-conjugated anti-human IgG (Sigma-Aldrich) was added (45' at 37° C.)
 After washing with PBS solution containing 0.2% (v/v) Tween20, TMB substrate kit (Thermo Scientific) was added and the plate incubated at 37° C. for 5'
 1N sulphuric acid was then added to stop the reaction.
 The signal was detected at 450 nm wavelength.

IgG2 Purification and Quantitation Protocol:

In order to purify and analyze the IgG2 fraction, the selected sera were purified using two different steps. Firstly, the total amount of IgG was purified with an affinity column. Secondly, the eluted total IgG content was further purified with an affinity column specific for IgG2 fraction.

a) Preparation of Total IgG Affinity Purification Column: Column 1 Preparation Protocol
 1 mL of gammabind Sepharose resin (stored at 4° C. in PBS1×-ethanol 20%) was washed 3 times with 30-40 mL PBS1× to eliminate the ethanol excess (centrifuge 5 min at 2500 rpm at room temperature and 2-3 acceleration and deceleration).
 Anti-human IgG (Cf=4 mg/mL) was added to the resin and gently stirred 90 min at room temperature.
 The resin was washed 3 times with 10 volumes (1 volume=1 mL of resin) of sodium borate 0.2M pH 9. Centrifuge 15 min at 2500 rpm.
 After the first centrifuge, the supernatant was recovered for further analysis.
 The resin was resuspended in 10 volumes of sodium borate 0.2 M pH 9 and shacked.
 A small amount of beads was removed for pre cross-linking checking.
 DMP (dimethyl-pimelimidate) was added up to 20 mM (final concentration). In this step takes place the cross-linking between IgGs and protein G of the resin. Stir gently 30 min at room temperature.
 A small amount of beads was removed for post cross-linking checking.
 After 15 min centrifuge (2500 rpm), the supernatant was removed and the resin was washed with 20 volumes of ethanolamine 0.2M pH 8.
 This step was repeated 3 times. This step allows the stabilization of new covalent links.
 The resin was then washed with 20 volumes of ethanolamine (0.2M pH 8) and stirred gently for 120 min at room temperature.
 After 15 min centrifuge (2500 rpm), the supernatant was removed and the resin was washed 3 times with 30 mL PBS1×.
 After 15 min centrifuge (2500 rpm), the supernatant was removed and 20 mL of PBS1× supplemented with NaN3 (final concentration 0.05%) were added.
 The resin was finally loaded on the chromatography column and then stored at 4° C.

b) Preparation of IgG2 Fraction Affinity Purification Column: Column 2 Preparation Protocol The protocol for the preparation of total IgGs-affinity purification column above described was used to prepare a new column allowing the purification of the IgG2 fraction. A single modification was performed in the protocol (second step of the Column 1 preparation protocol above described).

In particular:

A commercially available mouse anti-Human IgG2 Fc monoclonal antibody (*Acris* Antibodies) was added to the resin at the final concentration of 3 mg/mL and gently stirred for 90 min at room temperature.

c) Affinity Purification Procedure: Column 1/Column 2 Steps

The collected sera were firstly purified in the "Column no. 1" (total IgG purification column). Briefly, after incubating the different sera at room temperature, the column was washed with PBS1× allowing the elution of nonspecific serum proteins. The IgG fraction was then eluted by changing the pH of the column (pH 2.2).

After elution the total IgG containing solution was neutralized (pH 7.0) and loaded again into the "Column no. 2" (IgG2 fraction purification column). As described for Column 1 purification, the Column 2 eluted samples, were neutralized and stored at 4° C. to be further analysed.

d) Evaluation of the Purified IgG2

The affinity columns above described allowed the purification of IgG2 from human sera. In order to evaluate the quality of the samples purified, SDS-PAGE assays, followed by Coomassie staining were-performed:

The samples were analysed on 4-15% Tris-glycine pre-casted-gels (Bio-Rad).

Electrophoresis run was performed for 1 hour at 200V.

The electrophoresis gels were stained for 20 min with a Coomassie-blue solution.

The Coomassie-stained gels were washed in Destainer-containing solution for 2 hours and then washed with tap clean water.

Syncytia Formation Evaluation Through Bright Field Phase Contrast Optical Microscope Protocol:

$10^4$ Vero cells/well were grown till a 100% confluence in a 96-well plate in complete DMEM+10% FCS.

HSV-1 and HSV-2 viral stocks dilutions (−3 and −2 respectively) were pre-incubated with purified Fab of interest at different concentrations (10, 5 and 2.5 µg/mL) in a final volume of 100 µL of complete DMEM, for 1 h at 37° C. and 5% $CO_2$.

Experimental controls were-added as well.

After washing the cells with a PBS 1× solution, viral solutions were added to the monolayers and incubated for 2 h at 37° C. and 5% $CO_2$ for adsorption.

Each well was washed once in PBS 1×, then complete DMEM supplemented with 2% FCS were added to each well and incubated for 22 h at 37° C. and 5% $CO_2$.

Cells monolayer were fixed and stained with 1 mL of a water-based solution of 70% methanol and 1% crystal violet. The fixing/staining solution was removed after 5' incubation, and then the cells monolayer was washed once in $H_2O$ and dried.

The reduction of syncytia formation was assessed by bright field phase contrast optical microscope. In particular, the cell morphology observed in the cell monolayer infected with Fab or IgG1 Fab-treated viruses was compared with the virus control (same virus amount without purified IgG2) infected cells morphology.

Qualitative Immunofluorescence (IIF) Assay Protocol:

$10^4$ Vero cells/well were grown till a 100% confluency in a 96-well plate in complete DMEM+10% FCS.

Cells were infected with the same HSV-1 and HSV-2 viral stocks dilution used in neutralization assay, then adsorption and incubation were performed as previously described for viral titration.

Medium was removed, the cells monolayer was washed once in PBS 1× and fixed with 200 µL/well of a 1:1=acetone:methanol ice-cold solution. Fixing solution was removed. The plate was stored at −20° C.

The IIF staining was performed by adding anti-HSV-1 and HSV-2 gD2 protein mAbs commercially available (1 h 37° C. in dark humid chamber)

The plate was washed twice (5' in PBS1×)

A FITC-conjugated secondary mAb was added to the primary staining (1 h 37° C. in dark humid chamber)

The plate was washed twice (5' in PBS1×)

The nuclear staining was performed by adding Hoechst solution (15 min 37° C. in dark humid chamber)

The plate was washed twice (5' in PBS1×)

The infection foci were analysed through InCellAnalyzer system.

Quantitative Neutralizing Activity Evaluation Through Plaque Reduction Assay Protocol:

$7 \times 10^5$ Vero cells/well were seeded in a 6-wells plate and grown in the appropriate complete medium supplemented with 10% FCS. Experiment was performed with cells at 100% confluence.

HSV-1 and HSV-2 viral stocks dilution (−5 and −4 respectively) were pre-incubated with purified Fab of interest at different concentrations (5, 2.5 and 1 µg/mL) in a final volume of 800 µL of complete DMEM, for 1 h at 37° C. and 5% $CO_2$.

Experimental controls were added as well.

After washing the cells with a PBS 1× solution, viral solutions were added to the monolayers and incubated for 2 h at 37° C. and 5% $CO_2$ for adsorption.

Each well was washed once in PBS 1×, then 2 mL of complete DMEM supplemented with 2% FCS and 1% agarose were added to each well and incubated for 46 h at 37° C. and 5% $CO_2$.

Agarose layer was removed and cells monolayer fixed and stained with 1 mL of a water-based solution of 70% methanol and 1% crystal violet. Fixing/staining solution was removed after a 5' incubation, then the cells monolayer was washed once in PBS 1× and dried.

Neutralization activity was then assessed by counting the plaque forming units (PFU). In particular, the number of PFU in the cell monolayer infected with Fab-treated viruses was compared with the PFU counted for the virus control (same virus amount).

Quantitative Neutralizing Activity Evaluation Through Indirect Immunofluorescence (IIF) Assay Protocol:

$10^4$ Vero cells/well were grown till a 100% confluence in a 96-well plate in complete DMEM+10% FCS.

HSV-1 and HSV-2 viral stocks dilution (−4 and −2 respectively) were pre-incubated with purified Fab of interest at different concentrations in a final volume of 100 µL of complete DMEM, for 1 h at 37° C. and 5% $CO_2$.

Experimental controls were added as well.

After washing the cells with a PBS 1× solution, viral solutions were added to the monolayers and incubated for 2 h at 37° C. and 5% $CO_2$ for adsorption.

Each well was washed once in PBS 1×, then complete DMEM supplemented with 2% FCS were added to each well and incubated for 22 h at 37° C. and 5% $CO_2$.

Medium was removed, the cells monolayer was washed once in PBS 1× and fixed with 200 µL/well of a 1:1=acetone:methanol ice-cold solution. Fixing solution was removed. The plate was stored at −20° C.

The IIF staining was performed by adding anti-HSV-1 and HSV-2 mAbs commercially available (1 h 37° C. in dark humid chamber)

The plate was washed twice (5' in PBS1×)

A FITC-conjugated secondary mAb was added to the primary staining (1 h 37° C. in dark humid chamber)

The plate was washed twice (5' in PBS1×)

The nuclear staining was performed by adding Hoechst solution (15 min 37° C. in dark humid chamber)

The plate was washed twice (5' in PBS1×)

Neutralization activity was then assessed by counting the immunofluorescence infection foci through InCellAnalyzer system.

The number of infection foci in the cell monolayer infected with viruses treated with the different Fab preparations was compared with the foci counted for the virus control (same virus amount)

The percentage of neutralization was then evaluated and a standard deviation from the mean was calculated as well (the experiment was performed in triplicate)

Human Combinatorial Phage Displayed Antibody Library Construction Protocol:

PBMCs (peripheral blood mononuclear cells) were separated from a blood sample using Histopaque 1077 (Sigma), a Ficoll gradient solution designed for blood cell separation.

RNA was extracted from the isolated lymphocytes using Rneasy Mini Kit (Qiagen), and was retrotranscribed to cDNA using the Transcriptor 1st Strand cDNA Synthesis Kit for RT-PCR AMV (Roche), following the product manual instructions.

Previously obtained cDNA was-used as PCR template. In particular, using a specific set of primers described by Solforosi et al. (2012) "A phage display vector optimized for the generation of human antibody combinatorial libraries and the molecular cloning of monoclonal antibody fragments" New Microbiologica 35 (3), 289-294, the amplification of light (LC) and heavy chains (HC) of immunoglobulins belonging to IgG2 subclass was performed (see Supplementary 1 section for primer sequences).

All the amplified HC and LC were-purified after electrophoresis agarose gel "run" using QIAquick Gel extraction Kit, (Qiagen). After the purification step both chains were-also quantified (NanoDrop 8000, Higher throughput, full-spectrum microvolume UV-Vis measurements, ThermoScientific) and digested with selected restriction enzymes (as highlighted by the next two tables explaining the enzymatic digestion reaction mix) to clone them into the pCM vector (Solforosi et al. (2012) "A phage display vector optimized for the generation of human antibody combinatorial libraries and the molecular cloning of monoclonal antibody fragments" New Microbiologica 35 (3), 289-294, following the protocol already described.

More in detail, LCs and pCM were-digested with SacI and XbaI restriction enzymes (NEB) following the protocol shown in Table 5:

TABLE 5

| LC digestion | |
|---|---|
| LCs | Vector |
| LCs 5 µg | pCM vector 10 µg |
| SacI 35 U/µg | SacI 5 U/µg |
| XbaI 70 U/µg | XbaI 9 U/µg |
| Buffer 10X | Buffer 10X |
| BSA | BSA |

The digestions were-carried out for 45 min (vector) and 3 hours (LCs) respectively at 37° C. and the digested products were then checked through Sybr Safe staining. Digested pCM and LC DNA showing the correct molecular weight (3500 and 670 bps respectively) were extracted from agarose gel, purified (QIAquick Gel extraction Kit, Qiagen), and subsequently ligated (2 hours at room temperature) using T4 DNA ligase (NEB). The ligation product was-then used to transform electrocompetent cells (E. coli XL-1 Blue electrocompetent cells, Stratagene).

pCM containing LCs (pCMLc) was then purified (Qiagen Plasmid Midi Kit, Qiagen) from the transformed cells.

pCMLc vector and the previously amplified HCs were also digested, as explained in the next table showing the digestion conditions.

XhoI and SpeI restriction enzymes (NEB) were used, as follows in Table 6:

TABLE 6

| HC digestion | |
|---|---|
| HCs | pCMLc |
| HCs 5 µg | Vector 10 µg |
| XhoI 70 U/µg | XhoI 9 U/µg |
| SpeI 17 U/µg | SpeI 3 U/µg |
| Buffer 10X | Buffer 10X |
| BSA | BSA |

The digestions were carried out for 45 min (vector) and 3 hours (HCs) respectively at 37° C. and the digested products were then checked through Sybr Safe staining (FIG. 10).

Digested pCMLc and HC DNA showing the correct molecular weight (4000 and 730 bps respectively) were extracted from agarose gel, purified (QIAquick Gel extraction Kit, Qiagen), and subsequently ligated (2 hours at room temperature) using T4 DNA ligase (NEB). The ligation product was then used to transform "homemade" XL-1 Blue electrocompetent cells.

pCM containing LCs and HCs (pCMLcHc) was-then purified (Qiagen Plasmid Midi Kit, Qiagen) from the transformed cells.

Biopanning Protocol:

Day 1

Transform an aliquot of XL1-Blue electrocompetent cells with library DNA

After a recovery of 60' at 37° C. with agitation in 2 mL SOC medium (2% Tryptone, 0.5% Yeast extract, 10 mM NaCl, 2.5 mM KCl, 10 mM MgCl2, 10 mM MgSO$_4$, and 20 mM Glucose), add it to 10 mL SB medium (3.2% Tryptone, 2% Yeast extract, 0.5% Sodium chloride—pH: 7.0±0.2) with 10 µg/mL Tetracycline and 20 µg/mL Ampicillin ("Low Amp")

Library Titration: plate on Tet-Amp agar plates serial dilutions starting from $10^{-2}$ to $10^{-5}$ Incubate Low Amp for 60' at 37° C. with agitation Add 50 mL SB medium with 100 µg/mL Ampicillin ("High Amp") and incubate for 60' at 37° C. with agitation Add $10^{12}$ PFU (Plaque forming units: a measure of the number of particles capable of forming plaques per unit volume) of helper phage (homemade produced and titrated) and incubate for 60' at 37° C. with agitation Add 70 µg/mL Kanamycin and incubate overnight (ON) at 30° C.

Plate preparation for affinity selection of phages:

Vero E6 cells were seeded in a Costar™ 96-Well EIA/RIA Plate, $4 \times 10^4$ cells/well in DMEM+10% FBS, 4 wells for each infection, and incubated ON at 37° C., 5% $CO_2$. The following day HSV-1 (HF strain) stock was $10^{-2}$ diluted in DMEM without FBS and seeded on cells for 2 hours absorption. Then, the medium containing medium was replaced with DMEM+2% FBS and the plate was incubated for 20 hours at 37° C., 5% CO2. The infected cells were fixed using 40 uL/well of paraformaldehyde solution (Invitrogen IC Fixation Buffer—FB001) for 15' at room temperature. After the incubation time, the solution was replaced with 100 μL/well of PBS.

Day 2

Calculate the phage titre of day 1 using the following formula: $10^4 \times$ (dilution factor)×(number of colonies)/μL on the plate Inoculate an XL1-Blue colony in SB with 10 μg/mL Tetracycline (4 mL for each antigen, 2 mL for infection with Output phages and 2 mL for infection with Input phages) and incubate at 37° C. with agitation until reaching an optical density (OD) of 0.5 at 550 nm wavelength Phage Preparation:

After centrifugation (40' at 4° C., RCF: 1540×g) of the ON bacterial culture growth, pour the supernatant into sterile 50 mL tubes with 8 mL of PEG/NaCl solution and incubate for 30' on ice allowing the phages precipitation.

After centrifugation (25' at 4° C., RCF: 12130×g), discard the supernatant and gently resuspend the pellet with 1 mL of PBS/BSA 1% solution.

After centrifugation (5' at room temperature, RCF: 21380×g), collect the supernatant ("Unpanned phage")

Deselection Process:

a suspension of Vero E6 cells obtained from a 100% confluent T75 flask was fixed using 500 μL of paraformaldehyde solution (Invitrogen IC Fixation Buffer—FB001) for 15' at room temperature. After the incubation time, the cells were washed in PBS solution. Before adding the resuspended phage to the plate containing the treated HSV infected cells (selection step), the phage solution was pre-incubated with $1.5 \times 10^6$ cells/well for 60' at 37° C. with agitation (deselection step). After centrifugation (2' at room temperature, RCF: 21380×g), the supernatant was then collected and added to the plate with the fixed and permeabilized HSV infected cells.

Panning:

Incubate 70 μL/well of unpanned phage for 120' at 37° C.

Collect the supernatant from the 4 wells of each antigen as "Input" and store on ice Wash every well 10 times with 100 μL/well of PBS/Tween 0.5% solution at 37° C., pipetting 10 times each Add 50 μL/well of Elution Buffer (0.1 M Glycine-HCl, pH 2.2), incubate 1' and scrape off the bottom of the wells Collect the eluted phages with Neutralizing Buffer (2 M Tris, pH 8.0) as "Output" and store on ice Usually five selection rounds (six days) are needed in order to obtain a high affinity selection of clones with a significant antigen-binding activity from the phage population obtained from a DNA library of Fabs.

Importantly, a cross-selection of phage antibody library on HSV-1 and HSV-2 infected cells on the first panning selection round was performed.

Screening Protocol Using Freeze & Thawing Procedure:

Day 1:

Extract DNA obtained from High Amp of rounds 4 and 5 and double digest with SpeI and NheI restriction enzymes (NEB) for 60' at 37° C.

Separate the DNA of interest (the plasmid containing both HCs and LCs) from the phage protein (cpIII) previously fused to the Fabs, performing an agarose 1% gel electrophoresis run (85V for 3 hours) and extract with the QIAquick Gel Extraction Kit (QIAgen)

Ligate the extracted DNA using T4 ligase (NEB) and transform an aliquot of XL1-Blue elettrocompetent cells After recovery in SOC medium, plate on LB agar Day 2:

Inoculate colonies obtained on day 1 in 3 mL SB medium with 10 μg/mL

Tetracycline and 100 μg/mL Ampicillin for each one. Add a colony of not transformed XL1-Blue elettrocompetent cells in 3 mL SB medium with only 10 μg/mL tetracycline as negative control. Incubate the inoculates at 37° C. with agitation until reaching an optical density (OD) of 0.5 at 550 nm wavelength Induce the production of Fabs adding IPTG (Isopropyl β-D-1-thiogalactopyranoside—Sigma 16758) at the recommended dilution of 1:1000 and incubate ON at 30° C. with agitation Day 3:

After centrifugation (20' at 4° C., RCF: 1540×g) of the ON bacterial cultures growth, discard supernatant and resuspend the pellet with 1 mL of PBS.

Add a protease inhibitor and follow the Freeze&thaw procedure for three times:

Incubate on dry ice until complete freezing

Incubate at 37° C. with agitation until complete thawing

After centrifugation (10' at room temperature, RCF: 21380×g), use the supernatant for protein (Fab) expression screening and the pellet for DNA extraction and analysis.

Purification of Fab Clones Selected During Biopanning Procedures Protocol:

Day 1

Inoculate a fresh plate colony in 10 mL SB (Super Broth) containing 10 μL ampicillin (Cf=50 μg/mL, C. stock=100 mg/mL) and 20 μL tetracycline (Cf=100 μg/mL, C. stock=5 mg/mL) and incubate overnight at 37° C. in a rotatory shaker (180 rpm)

Day 2

Sub-inoculate 5 mL of the inoculum into 500 mL SB (Super Broth) containing 500 μL ampicillin (Cf=50 μg/mL, C. stock=100 mg/mL) and 1 mL tetracycline (Cf=100 μg/mL, C.stock=5 mg/mL) and incubate at 37° C. for 6-8 hours in a orbital shaker (180 rpm)

When the culture OD reach 0.8-1 (exponential growth) add IPTG (isopropyl-b-D-thiogalactopyranoside) at a final concentration of 1 mmol/L Incubate overnight at 30° C. in a orbital shaker (180 rpm)

Day 3

Transfer the bacterial culture in clean 250 mL bottles.

Centrifuge (20-30' at 3500-4500 rpm) at 4° C. or room temperature.

Resuspend cellular pellet in a final volume of 25 mL of PBS1× into falcon 50 mL, add protease inhibitors and place the falcon at 4° C.

Maintaining the falcon on ice, sonicate cellular suspension 90", pause 60". Repeat this 3-4 times.

Transfer the bacterial lysate in bottle (30 mL). Eliminate cell debris by centrifugation for 30' at 15.000 rpm at 4° C.

Filter the supernatant using syringe 50 ml and filters Millipore PVDF from 0.45 um and then from 0.2 um. Collect the filtrate into falcon 50 mL.

Store at 4° C.

Purify the Fab by Immunoaffinity Chromatography:

Wash the column with 20 mL PBS1×. Repeat twice

Elution with 10 mL Elution Buffer pH 2.2

Rebalance the pH of the column with PBS1×, check the pH

Close column cap. Load on the column sample, 2-4 mL at a time. Wait few minutes and reopen the column Wash the column with 50 mL PBS1×

Close column cap. Load on the column 10 mL Elution Buffer pH 2.2, 2-4 mL at a time. Wait few minutes and reopen the column.

Collect the eluate in falcon containing Neutralising Buffer pH 11

Check the pH and neutralise the solution (pH 7-8) using Neutralising Buffer pH 11

Rebalance the pH of the column with PBS1×

Elution with 10 mL Elution Buffer pH 2.2

Rebalance the pH of the column with PBS1×, check the pH

Add 20 mL PBS1×+200 µL NaN3100× and store the column at 4° C.

Wash Centricon with PBS1×: centrifuge 10-15' at 4000 rpm. Then, concentrate Fab with centrifugation for 10-15' at 4000 rpm.

Take the Fab purified retained by the filter and store at 4° C.

The correct expression and the concentration of purified Fabs were calculated respectively by SDS-PAGE/coomassie staining (as already described in IgG2 Purification and quantitation protocol).

Conversion of IgG2 Fab Fragments into IgG1 Fab Protocol

This cloning procedure was performed using the pCM vector (Solforosi et al. (2012) "A phage display vector optimized for the generation of human antibody combinatorial libraries and the molecular cloning of monoclonal antibody fragments" New Microbiologica 35 (3), 289-294) already containing HC and LC sequences of an IgG1 antibody. A Nhel restriction site was introduced between the VH and CH1 sequences of the aforementioned IgG1-Fab allowing the molecular cloning of only the VH fragment of the HC.

The VH sequences of selected anti-HSV Fabs were cloned in frame with IgG1-CH1. More in details, a Nhel restriction site was added at 3' end of selected Fab VH sequences by PCR amplification using specific designed primers containing the restriction site.

All the amplified VH were purified using QIAquick PCR Purification Kit, (Qiagen). After the purification step VH chains were also quantified (NanoDrop 8000, Higher throughput, full-spectrum microvolume UV-Vis measurements, ThermoScientific) and digested with selected restriction enzymes to clone them into the expression vector, following the protocol already described.

More in detail, both amplified VHs and vector were digested with XhoI and Nhel restriction enzymes (NEB) following the protocol of Table 7:

TABLE 7

| VHs | IgG1 Ab Vector |
|---|---|
| VH 0.5 µg | Vector 5 µg |
| XhoI 10 U/µg | XhoI 10 U/µg |
| Nhel 10 U/µg | Nhel 10 U/µg |
| Buffer cutsmart 10X | Buffer cutsmart 10X |

The digestions were carried out for 1 hour at 37° C. and the digested products were then checked through Sybr Safe staining.

Digested products showing the correct molecular weight (4474 bp for VH-digested vector and 426 bps for VHs) were extracted from agarose gel, purified (QIAquick Gel extraction Kit, Qiagen), and subsequently ligated (10 minutes at room temperature) using T4 DNA ligase (NEB). The ligation product was then used to transform electrocompetent cells (E. coli XL-1 Blue electrocompetent cells, Stratagene).

Plasmids containing VHs ligated in frame with IgG1-CH1 (pVH-CH1-IgG1) were then purified (Qiagen Plasmid Midi Kit, Qiagen) from the transformed cells and the correct insertion was analysed sequencing the portion of interest with a specific subset of primers.

pVH-CH1-IgG1 constructs and the LCs belonging to HSV Fab panel were also digested as explained in Table 8 showing the digestion conditions.

TABLE 8

| LCs | pVH-CH1-IgG1 |
|---|---|
| LC 0.5 µg | Vector 2 µg |
| SacI 10 U/µg | SacI 10 U/µg |
| XbaI 10 U/µg | XbaI 10 U/µg |
| Buffer cutsmart 10X | Buffer cutsmart 10X |

The digestions were carried out for 1 hour at 37° C. and the digested products were then checked through Sybr Safe staining.

Digested pVH-CH1-IgG1 and LC DNAs showing the correct molecular weight (4230 and 670 bps respectively) were extracted from agarose gel, purified (QIAquick Gel extraction Kit, Qiagen), and subsequently ligated (10 minutes at room temperature) using T4 DNA ligase (NEB). The ligation product was then used to transform XL-1 Blue electrocompetent cells (Stratagene). Plasmids containing LCs and HCs of the different anti-HSV clones (pVH-CH1_LC-IgG1Fab) were then purified (Qiagen Plasmid Midi Kit, Qiagen) from the transformed cells and the correct insertion was analysed sequencing the portion of interest with a specific subset of primers.

As described in the cloning protocol paragraph, all the new IgG1 Fab clones were sequenced in order to check the correct insertion of VH-HCs and LCs.

ScFvA Construction

In order to extensively characterise mAb A (or Ex2) features in its different formats, the mAb has been also expressed as a single chain antibody A (ScFvA). Variable light chain (VL) and variable heavy chain (VH) of Fab A have been amplified and used for the construction of a single chain (ScFv).

The ScFv gene cassette is composed by:
a) DNA encoding for Fab A VL and VH
b) DNA encoding for a linker region [(Gly×3Ser)×3]
c) DNA encoding protein tag (Poly-Histidine)

The ScFv Fab A (Fab Ex2) gene cassette has been constructed as follows:

a) DNA Encoding for Fab a VL and VH

As stated above, the Fab A variable regions for the Light and Heavy chains (VL and VH respectively) have been successfully amplified by PCR (polymerase chain reaction) from the DNA template encoding for mAb A light and heavy variable regions. The primers used to amplify mAb A LC and HC from DNA template contained:

At 5' VL end the restriction site SacI (New England Biolabs, NEB) to be used for the insertion of the whole ScFv gene cassette into vector.

At 3' VL end the part of the DNA sequence encoding for the linker region (linker overlap region)

At 5' VH part of the DNA sequence encoding for the linker region (linker overlap region)

At 3' VH the DNA sequence coding for the His Tag and the restriction site SpeI (NEB) to be used for the insertion of the whole ScFv gene cassette into expression vector. All the gene fragments amplified as above described have been used to perform overlap PCRs in order to construct the full length ScFv gene cassette b) DNA Encoding for a Linker Region [(Glyx$_3$Ser)x$_3$]

The linker region (in between LC and HC) main function is structural, in particular a linker region composed by [(Gly)$_3$Ser]$_3$ is characterised by high flexibility allowing a proper ScFv folding after expression. The linker region has been added in between the VL and VH by PCR overlap techniques.

c) DNA Encoding Protein Tag (Poly-Histidine)

Poly-Histidine Tag region (His-Tag) is fundamental for the ScFv purification by affinity chromatography. In particular, this region is selectively bound by Ni2+ NiNta resin (commercially available, QIAGEN) routinely used to purify His-Tag containing proteins. His-Tag DNA sequence has been added to ScFv gene cassette introducing Poly-His DNA coding sequence into 3'VH primer already containing the Spe I restriction site.

The gene cassette has been then cloned vector and ScFvA has been produced, using the following protocol:

1. Transformation of bacteria (XL-1 Blue, Stratagene) with ScFv containing vector XL-1 Blue bacteria have been transformed (by elettroporation) with vector containing the ScFv A gene cassette.

2. Selective culturing of bacteria containing the ScFv vector

XL1 Blue bacteria correctly transformed with ScFv vector have been cultured and selected with antibiotic (ampicillin) thanks to the ampr (ampicillin resistance gene) resistance marker carried by the vector.

3. ScFv expression induction

The expression of ScFv A has been induced by adding the so called "inductor" (IPTG) to the culture broth containing ScFv transformed bacteria 4. Cultured bacteria sonication In order to collect the ScFv produced by bacteria after the induction step, ScFvA expressing bacteria have been sonicated to disrupt bacterial wall and release ScFvA produced by bacteria.

5. Centrifugation of cell free supernatant to pellet cellular debris. Sonicated bacteria product, has been extensively centrifuged in order to pellet bacterial cell debris.

6. Ni$^{2+}$ affinity chromatography purification

Supernatants resulting from step 5, have been collected and loaded into Ni2+ affinity chromatography column in order to purify the ScFv thanks to His-Tag.

7. ScFv collection

Purified ScFv has been then collected and stored at −20° C.

The invention claimed is:

1. A non-naturally occurring HSV-1 and HSV-2 binding monoclonal antibody or fragment thereof not structurally identical to naturally occurring antibodies or fragments thereof comprising a heavy chain (VH) variable region of SEQ ID NO: 1 and a light chain (VL) variable region of SEQ ID NO: 2.

2. The non-naturally occurring HSV-1 and HSV-2 binding monoclonal antibody or fragment thereof, according to claim 1, wherein said antibody is a humanized antibody.

3. The non-naturally occurring HSV-1 and HSV-2 binding monoclonal antibody or fragment thereof, according to claim 1, wherein said antibody has IgG1 heavy chain constant regions.

4. The non-naturally occurring HSV-1 and HSV-2 binding monoclonal antibody or fragment thereof, according to claim 1, wherein said antibody has IgG2 heavy chain constant regions.

5. A pharmaceutical composition comprising the non-naturally occurring HSV-1 and HSV-2 binding monoclonal antibody or fragment thereof according to claim 1 and a pharmaceutically acceptable carrier.

6. The pharmaceutical composition according to claim 5, for oral, topical, ophthalmic, intramuscular, intravenous infusion, subcutaneous, or inhalation administration routes.

7. The pharmaceutical composition according to claim 5, used in combination with at least one antiviral agent.

8. A method of treating HSV-1 and/or HSV-2 associated diseases comprising administering to a patient in need thereof a non-naturally occurring HSV-1 and HSV-2 binding monoclonal antibody or fragment thereof according to claim 1.

9. The method according to claim 8, wherein said treatment is of patients who are resistant or intolerant to previous treatment with at least one antiviral agent or wherein the treatment with an antiviral agent should be avoided, or wherein said patients are immunodepressed or immunosuppressed.

10. The method according to claim 8, wherein said treatment is prophylactic or therapeutic.

11. The method according to claim 8, wherein said HSV-1 and/or HSV-2-associated diseases are acute or chronic and wherein HSV-1 and HSV-2 infections are primary infections, non-primary infections or recurrences.

12. The method according to claim 11, wherein said HSV-1 and/or HSV-2 associated diseases are chosen from the group consisting of oral herpes, herpes keratitis, herpes whitlow, herpes gladiatorum, eczema herpeticum, neonatal herpes, genital herpes, atypical genital herpes, herpetic cervicitis, herpetic proctitis, herpetic encephalitis, herpetic meningitis, herpetic meningoencephalitis, and disseminated herpes simplex infection.

13. A method of decreasing viral shedding and preventing transmission comprising administering to a patient in need thereof a non-naturally occurring HSV-1 and HSV-2 binding monoclonal antibody or fragment thereof according to claim 1.

* * * * *

UNITED STATES PATENT AND TRADEMARK OFFICE
CERTIFICATE OF CORRECTION

PATENT NO. : 10,626,167 B2
APPLICATION NO. : 15/546422
DATED : April 21, 2020
INVENTOR(S) : Roberto Burioni et al.

Page 1 of 1

It is certified that error appears in the above-identified patent and that said Letters Patent is hereby corrected as shown below:

On the Title Page

Item (30), under "Foreign Application Priority Data," "15152909" should read --15152909.6--.

Signed and Sealed this
Seventh Day of July, 2020

Andrei Iancu
*Director of the United States Patent and Trademark Office*